US007456027B2

(12) United States Patent
Wang et al.

(10) Patent No.: US 7,456,027 B2

(45) Date of Patent: Nov. 25, 2008

(54) PROTEOLYTIC BIOMARKERS FOR TRAUMATIC INJURY TO THE NERVOUS SYSTEM

(75) Inventors: Kevin Ka-Wang Wang, Gainesville, FL (US); Ronald Hayes, Gainesville, FL (US); Ming Chen Liu, Gainesville, FL (US); Monika Oli, Gainesville, FL (US)

(73) Assignees: University of Florida Research Foundation, Inc., Gainesville, FL (US); Banyan Biomarkers, Inc., Alachua, FL (US)

( * ) Notice: Subject to any disclaimer, the term of this patent is extended or adjusted under 35 U.S.C. 154(b) by 188 days.

(21) Appl. No.: 11/106,932

(22) Filed: Apr. 15, 2005

(65) Prior Publication Data

US 2005/0260697 A1 Nov. 24, 2005

Related U.S. Application Data

(60) Provisional application No. 60/562,819, filed on Apr. 15, 2004.

(51) Int. Cl.
*G01N 33/567* (2006.01)
*G01N 33/48* (2006.01)

(52) U.S. Cl. ........................................ 436/503; 436/53

(58) Field of Classification Search ........................ None
See application file for complete search history.

(56) References Cited

U.S. PATENT DOCUMENTS

| | | | | |
|---|---|---|---|---|
| 5,118,606 | A | 6/1992 | Lynch et al. | |
| 6,048,703 | A | 4/2000 | Siman et al. | |
| 6,589,746 | B1 | 7/2003 | Zelman | |
| 2003/0040660 | A1 | 2/2003 | Jackowski et al. | |
| 2004/0241762 | A1* | 12/2004 | Shaw et al. | 435/7.2 |
| 2005/0202508 | A1* | 9/2005 | Pasinetti | 435/7.1 |
| 2005/0260654 | A1 | 11/2005 | Hayes et al. | |
| 2006/0246489 | A1 | 11/2006 | Svetlov et al. | |
| 2007/0003982 | A1 | 1/2007 | Hayes et al. | |

FOREIGN PATENT DOCUMENTS

WO WO 95/26506 10/1995

OTHER PUBLICATIONS

Estrov et al. Caspase 2 and Caspase 3 Protein Levels as Predictors of Survival in Acute Myelogenous Leukemia; Blood, vol. 92, No. 9 (1998) pp. 3090-3097.*

Woolf et al. Hippocampal Microtubule-Associated Protein-2 Alterations With Contextual Memory; Brain Research, vol. 821 (1999) pp. 241-249.*

Li et al. Neuronal Damage and Plasticity Identified by Microtubule-Associated Protein 2, Growth-Associated Protein 43, and Cyclin D1 Immunoreactivity After Focal Cerebral Ishemia in Rats; Stroke, vol. 29 (1998) pp. 1972-1981.*

Malmendal et al. Nascent Structure in the Kinase Anchoring Domain of Microtubule-Associated Protein 2; Biochemical and Biophysical Research Communications, vol. 301 (2003) pp. 136-142.*

Posmantur et al. Neurofilament 68 and Neurofilament 200 Protein Levels Decrease After Traumatic Brain Injury; Journal of Neurotrauma, vol. 11, No. 5 (1994) pp. 533-545.□□.*

Nam et al. Nanoparticle-Based Bio-Bar Codes for the Ultrasensitive Detection of Proteins; Science, vol. 301 (2003) pp. 1884-1886.*

Liu et al. Extensive Myelin Basic Protein Degradation in the Rat Brain After Traumatic Brain Injury; Journal of Neurochemistry, vol. 87, Supplement 1 (2003) pp. 146.*

Blasko et al. Experimental Traumatic Brain Injury in Rats Stimulates the Expression, Production and Activity of Alzheimer's Disease Beta-Secretase (BACE-1); Journal of Neural Transmission, vol. 111 (2004) pp. 523-536.*

Zemlan et al. C-Tau Biomarker of Neuronal Damage in Severe Brain Injured Patients: Association With Elevated Intracranial Pressure and Clinical Outcome; Brain Research, vol. 947 (2002) pp. 131-139.*

Borghi, R. et al. "Full length alpha-synuclein is present in cerebrospinal fluid from Parkinson's disease and normal subjects", 2000, Neuroscience Letters, 287:65-67.

Dambinova, S. et al. "The presence of autoantibodies to N-terminus domain of GluR1 subunit of AMPA receptor in the blood serum of patients with epilepsy", 1997, Journal of Neurological Sciences, 152:93-97.

Dambinova, S. et al. "Blood Test Detecting Autoantibodies to N-Methyl-D-aspartate Neuroreceptors for Evaluation of Patients with Transient Ischemic Attack and Stroke", 2003, Clinical Chemistry, 49(10):1752-1762.

Jakowec, M. et al. "The native form of alpha-synuclein is not found in the cerebrospinal fluid of patients with Parkinson's disease or normal controls", 1998, Neuroscience Letters, 253:13-16.

Posmantur, R. et al. "A calpain inhibitor attenuates cortical cytoskeletal protein loss after experimental traumatic brain injury in the rat", 1997, Neuroscience, 77(3):875-888.

Pike, B. et al. "Accumulation of non-erythroid alpha II-spectrin and calpain-cleaved alpha II-spectrin breakdown products in cerebrospinal fluid after traumatic brain injury in rats", 2001, Journal of Neurochemistry, 78:1297-1306.

Rosengren, L. et al. "Patients with Amyotrophic Lateral Sclerosis and Other Neurodegenerative Diseases Have Increased Levels of Neurofilament Protein in CSF", 1996, Journal of Neurochemistry, 67(5):2013-2018.

Zemlan, F. et al. "Quantification of Axonal Damage in Traumatic Brain Injury: Affinity Purification and Characterization of Cerebrospinal Fluid Tau Proteins", 1999, Jounal of Neurochemistry, 72(2):741-750.

(Continued)

*Primary Examiner*—Jon P Weber
*Assistant Examiner*—Paul C. Martin
(74) *Attorney, Agent, or Firm*—Saliwanchik, Lloyd & Saliwanchik

(57) ABSTRACT

The present invention identifies biomarkers that are diagnostic of nerve cell injury, organ injury, and/or neuronal disorders. Detection of different biomarkers of the invention are also diagnostic of the degree of severity of nerve injury, the cell(s) involved in the injury, and the subcellular localization of the injury.

15 Claims, 7 Drawing Sheets

OTHER PUBLICATIONS

Sjogren, M. et al. "Neurofilament Protein in Cerebrospinal Fluid: A Marker of White Matter Changes", 2001, Journal of Neuroscience Research, 66:510-516.
Shea, T. et al. "Calcium Influx into Human Neuroblastoma Cells Induces ALZ-50 Immunoreactivity: Involvement of Calpain-Mediated Hydrolysis of Protein Kinase C", 1996, Journal of Neurochemistry, 66(4):1539-1549.
Denning, M. et al. "Protein Kinase C delta is Activated by Capase-dependent Proteolysis during Ultraviolet Radiation-induced Apoptosis of Human Keratinocytes", 1998, The Journal of Biological Chemistry, 273(45)29995-30002.
Koriyama, H. et al. "Proteolytic Activation of Protein Kinase C delta and epsilon by Capase-3 in U937 Cells During Chemotherapeutic Agent-Induced Apoptosis", 1999, Cell Signal, 11(11):831-838.
Schwab, BL et al. "Cleavage of plasma membrane calcium pumps by caspases: a link between apoptosis and necrosis", 2002, Cell Death and Differentiation, 9:818-831.
Hajimohammadreza, I. et al. "A Specific Inhibitor of Calcium-Calmodulin-Dependent Protein Kinase-II Provides Neuroprotection Against NMDA- and Hypoxia/Hypoglycemia-Induced Cell Death", 1995, The Journal of Neuroscience, 15(5)4093-4101.
Hajimohammadreza, I.et al. "Neuronal Nitric Oxide Synthase and Calmodulin-Dependent Protein Kinase II alpha Undergo Neurotoxin-Induced Proteolysis", 1997, Journal of Neuorchemistry, 69(3):1006-1013.
Toyota, H. et al. "Calpain-induced Bax-clevage product is a more potent inducer of cell death than wild-type Bax", 2003, Cancer Letters, 189:221-230.
McGinnist, K. et al. "Calcium/Calmodulin-dependent Protein Kinase IV Is Cleaved by Caspase-3 and Calpain in SH-SY5Y Human Neuroblastoma Cells Undergoing Apoptosis", 1998, The Journal of Biological Chemistry, 273(32):19993-20000.
Cao, X. et al. "Cleavage of Bax to p18 Bax accelerates stress-induced apoptosis, and a cathespin-like protease may rapidly degrade p18 Bax", 2003, Blood, 102(7):2605-2614.
Shigeta K. et al. "Fragmentation of a 70000-dalton calpastatin molecule upon its complex formation with calpain", 1984, Biochem. Int., 9(3):327-33.
Mukerjee, N. et al. "Caspase-Mediated Calcineurin Activation Contributes to IL-2 Release during T Cell Activation", 2001, Biochemical and Biophysical Research Communications, 285(5):1192-1199.
Estrov, et al, "Caspase 2 and Caspase 3 Protein Levels as Predictors of Survival in Acute Myelogenous Leukemia", *Blood*, Nov. 1, 1998, pp. 3090-3097, vol. 92, No. 9.
Pettigrew, L. Creed, et al., "Microtubular Proteolysis in Focal Cerebral Ischemia", *Journal of Cerebral Blood Flow & Metabolism*, 1996, pp. 1189-1202, vol. 16.

* cited by examiner

PROTEOLYTIC BIOMARKERS FOR TRAUMATIC INJURY TO THE NERVOUS SYSTEM

CROSS-REFERENCE TO RELATED APPLICATIONS

The present application claims the priority of U.S. Provisional Patent application No. 60/562,819 filed Apr. 15, 2004; and entitled "PROTEOLYTIC MARKERS AS DIAGNOSTIC BIOMARKERS FOR CANCER, ORGAN INJURY AND MUSCLE REHABILITATION/EXERCISE OVERTRAINING" which is incorporated herein by reference in its entirety.

The subject invention was made with government support under a research project supported by National Institutes of Health Grant #R01 NS39091, National Institutes of Health Grant #R01 NS40182, U.S. Army Grant #DAMD 17-99-1-9565, and U.S. Army Grant #DAMD 17-01-1-0765.

FIELD OF THE INVENTION

The invention provides for the reliable detection and identification of biomarkers that are uniquely produced in brain injury and/or stress, neuronal disorders, organ injury and/or stress, cancer and cancer treatment, and muscle rehabilitation/exercise overtraining and that are important for the diagnosis and prognosis and the monitoring of damage of the same organ/tissue system of interest. The profile of proteolytic products or fragments of organ-enriched or specific proteins/peptides in patients with damage to organ or tissue and cells within them are distinguished from normal controls using inexpensive techniques. These techniques provide simple yet sensitive approaches to diagnosing damage or stress to the central and peripheral nervous system, to other organs or to multiple organs, various cancers, cancer treatment, muscle rehabilitation/exercise overtraining and other human pathological or stressed conditions where major organ(s) is compromised or altered using biological fluids.

BACKGROUND OF THE INVENTION

The incidence of traumatic brain injury (TBI) in the United States is conservatively estimated to be more than 2 million persons annually with approximately 500,000 hospitalizations. Of these, about 70,000 to 90,000 head injury survivors are permanently disabled. The annual economic cost to society for care of head-injured patients is estimated at $25 billion. These figures are for the civilian population only and the incidence is much greater when combat casualties are included. In modern warfare (1993-2000), TBI is the leading cause of death (53%) among wounded who have reached medical care facilities.

Assessment of pathology and neurological impairment immediately after TBI is crucial for determination of appropriate clinical management and for predicting long-term outcome. The outcome measures most often used in head injuries are the Glasgow Coma Scale (GCS), the Glasgow Outcome Scale (GOS), computed tomography, and magnetic resonance imaging (MRI) to detect intracranial pathology. However, despite dramatically improved emergency triage systems based on these outcome measures, most TBI suffer long term impairment and a large number of TBI survivors are severely affected despite predictions of "good recovery" on the GOS. In addition, CT and MRI are expensive and cannot be rapidly employed in an emergency room environment. Moreover, in austere medical environments associated with combat, accurate diagnosis of TBI would be an essential prerequisite for appropriate triage of casualties.

Accordingly, the neural pathways of a mammal are particularly at risk if neurons are subjected to mechanical or chemical trauma or to neuropathic degeneration sufficient to put the neurons that define the pathway at risk of dying. A host of neuropathies, some of which affect only a subpopulation or a system of neurons in the peripheral or central nervous systems have been identified to date. The neuropathies, which may affect the neurons themselves or the associated glial cells, may result from cellular metabolic dysfunction, infection, exposure to toxic agents, autoimmunity dysfunction, malnutrition or ischemia. In some cases the cellular dysfunction is thought to induce cell death directly. In other cases, the neuropathy may induce sufficient tissue necrosis to stimulate the body's immune/inflammatory system and the mechanisms of the body's immune response to the initial neural injury then destroys the neurons and the pathway defined by these neurons.

Another common injury to the CNS is stroke, the destruction of brain tissue as a result of intracerebral hemorrhage or infarction. Stroke is a leading cause of death in the developed world. It may be caused by reduced blood flow or ischemia that results in deficient blood supply and death of tissues in one area of the brain (infarction). Causes of ischemic strokes include blood clots that form in the blood vessels in the brain (thrombus) and blood clots or pieces of atherosclerotic plaque or other material that travel to the brain from another location (emboli). Bleeding (hemorrhage) within the brain may also cause symptoms that mimic stroke. The ability to detect such injury is lacking in the prior art.

Mammalian neural pathways also are at risk due to damage caused by neoplastic lesions. Neoplasias of both the neurons and glial cells have been identified. Transformed cells of neural origin generally lose their ability to behave as normal differentiated cells and can destroy neural pathways by loss of function. In addition, the proliferating tumors may induce lesions by distorting normal nerve tissue structure, inhibiting pathways by compressing nerves, inhibiting cerebrospinal fluid or blood supply flow, and/or by stimulating the body's immune response. Metastatic tumors, which are a significant cause of neoplastic lesions in the brain and spinal cord, also similarly may damage neural pathways and induce neuronal cell death.

Identification and development of proteolytic products as biomarkers and/or diagnostic markers has been primarily focused within the confines of the CNS. Damage to peripheral nerves, such as occurred with diabetic neuropathies or administration of chemo-therapeutic agents such as those used to treat cancer, can also involve proteolytic damage similar to that seen in the CNS. Moreover, since protease activation is a major theme during cell injury in other organ injury (such as liver, kidney, lung, gut, heart etc.), or skeletal muscle overtraining and cancer cell proliferation or chemotherapy-induced tumor cell death and tumor shrinkage, this invention has a board-based application in diagnostics and monitoring of various organ injuries, multiple organ injury, CABG, sepsis, hyperventilation induced lung injury, muscle overtraining, cancer and the like.

There is thus, a need in the art for appropriate, specific, inexpensive and simple diagnostic clinical assessments of individual or multiple organ injury or stress, various organ-specific cancers and muscle training or overtraining, their severity and therapeutic treatment monitoring and efficacy assessment. Thus identification of proteolytic products of proteins or peptides that are specific to or predominantly found in a specific organ would prove immensely beneficial for both prediction of outcome and for guidance of targeted therapeutic delivery or muscle training and rehabilitation monitoring.

SUMMARY

The invention provides for the reliable detection and identification of biomarkers that are uniquely produced in brain injury and/or stress, neuronal disorders, organ injury and/or stress, cancer and cancer treatment, and muscle rehabilitation/exercise overtraining and that are important for the diagnosis and prognosis and the monitoring of damage of the same organ/tissue system of interest. The profile of proteolytic products or fragments of organ-enriched or specific proteins/peptides in patients with damage to organ or tissue and cells within them are distinguished from normal controls using inexpensive techniques. These techniques provide simple yet sensitive approaches to diagnosing damage or stress to the nervous system, to other organs or to multiple organs, various cancers, cancer treatment, muscle rehabilitation/exercise over-training and other human pathological or stressed conditions where major organ(s) is compromised or altered using biological fluids.

In a preferred embodiment, the invention provides biomarkers that are indicative of traumatic brain injury, neuronal damage, neural disorders, brain damage, neural damage due to drug or alcohol addiction, and diseases associated with the brain or nervous system, such as the central and peripheral nervous systems (CNS, PNS). Preferably, the biomarkers are proteolytic enzymes which are activated as a result of damage to organs such as for example: heart, brain, liver, kidneys, lung, gut; neurons, central nervous system, peripheral nervous system, as well as skeletal muscles. Preferably the proteolytic enzymes are activated and cleave target proteins, peptides and fragments thereof due to neural and organ injury. Target proteins include, but are not limited to proteins, peptides or fragments thereof associated with neuronal cells, brain cells or any cell that is present in the brain and central nervous systems, organs such as heart, liver, kidneys and the like. Non-limiting examples of proteolytic enzymes that are detected upon neural and/or organ injury include: Achromopeptidase, Aminopeptidase, Ancrod, Angiotensin Converting Enzyme, Bromelain, Calpain, Calpain I, Calpain II, Carboxypeptidase A, Carboxypeptidase B, Carboxypeptidase G, Carboxypeptidase P, Carboxypeptidase W, Carboxypeptidase Y, Caspase, Caspase 1, Caspase 2, Caspase 3, Caspase 4, Caspase 5, Caspase 6, Caspase 7, Caspase 8, Caspase 9, Caspase 10, Caspase 13, Cathepsin B, Cathepsin C, Cathepsin D, Cathepsin G, Cathepsin H, Cathepsin L, Chymopapain, Chymase, Chymotrypsin, α-Clostripain, Collagenase, Complement C1r, Complement C1s, Complement Factor D, Complement factor I, Cucumisin, Dipeptidyl peptidase IV, Elastase, leukocyte, Elastase, pancreatic, Endoproteinase Arg-C, Endoproteinase Asp-N, Endoproteinase Glu-C, Endoproteinase Lys-C, Enterokinase, Factor Xa, Ficin, Furin, Granzyme A, Granzyme B, HIV Protease, Igase, Kallikrein tissue, Kinase, Leucine Aminopeptidase (General), Leucine aminopeptidase, cytosol, Leucine aminopeptidase, microsomal, Matrix metalloprotease, Methionine Aminopeptidase, Neutrase, Papain, Pepsin, Plasmin, Prolidase, Pronase E, Prostate Specific Antigen, Protease, Protease S, Proteasomes, Proteinase, Proteinase 3, Proteinase A, Proteinase K, Protein C, Pyroglutamate aminopeptidase, Renin, Rennin, Thrombin, Tissue Plasminogen Activator, Troponins, Trypsin, Tryptase, Urokinase. Preferably, any one of SEQ ID NO's.: 1-148 are also detected.

In another preferred embodiment, the proteolytic enzyme biomarkers have a specific activity for the protein substrates, for example the non limiting examples listed in Table 1, of about 1 μg to about 500 μg per 1 mg of substrate protein per being proteolyzed in injured or stressed organs within minutes to days after or, as shown in vitro using purified protease-substrate protein/protein mixture ratio of 1/10,000 to 1/20 at a time point within minutes to hours.

In a preferred embodiment the biomarkers are activated upon injury of, for example, an organ, or neuronal cells, and result in the proteolysis of proteins, peptides associated with the organ or neuronal cells. Examples of preferred proteins include but are not limited to: troponins such as cardiac or muscle troponins, such as, for example, troponin I, troponin-T, troponin-C; neural peptides, including, but not limited to peptides of axonal proteins, amyloid precursor protein, dendritic proteins, somal proteins, presynaptic proteins, post-synaptic proteins fragments and derivatives thereof.

In another preferred embodiment, peptides identified as targets for proteolytic enzyme biomarkers for diagnosis and detection of brain and/or CNS/PNS injury or neural disorders are identified by SEQ ID NO's:1-149.

In another preferred embodiment, peptides identified as targets for proteolytic enzyme biomarkers for diagnosis and detection of brain and/or CNS injury or neural disorders are about 50% homologous to peptides identified by SEQ ID NO's: 1-149. Preferably the peptides identified as targets for proteolytic enzyme biomarkers for diagnosis and detection of brain and/or CNS injury or neural disorders are about 70% homologous to peptides identified by SEQ ID NO's: 1-149. Preferably the peptides identified as targets for proteolytic enzyme biomarkers for diagnosis and detection of brain and/or CNS injury or neural disorders are about 80% homologous to peptides identified by SEQ ID NO's: 1-149, preferably the peptides identified as targets for proteolytic enzyme biomarkers for diagnosis and detection of brain and/or CNS injury or neural disorders are about 90%, 95%, 96%, 97%, 95%, 99% or 99.9% homologous to peptides identified by SEQ ID NO's: 1-149.

In another preferred embodiment, peptides identified as targets for proteolytic enzyme biomarkers for diagnosis and detection of brain and/or CNS injury or neural disorders are at least about 10 amino acids longer either at the N-Terminal and/or C-Terminal of the peptides identified by SEQ ID NO's: 1-149. Preferably the peptides identified as targets for proteolytic enzyme biomarkers for diagnosis and detection of brain and/or CNS injury or neural disorders are at least about 20 amino acids longer either at the N-Terminal and/or C-Terminal of the peptides identified by SEQ ID NO's: 1-149. Preferably the peptides identified as targets for proteolytic enzyme biomarkers for diagnosis and detection of brain and/or CNS injury or neural disorders are at least about 50 amino acids longer either at the N-Terminal and/or C-Terminal of the peptides identified by SEQ ID NO's: 1-149. Preferably the peptides identified as targets for proteolytic enzyme biomarkers for diagnosis and detection of brain and/or CNS injury or neural disorders are at least about 80 amino acids longer either at the N-Terminal and/or C-Terminal of the peptides identified by SEQ ID NO's: 1-149. Preferably the peptides identified as targets for proteolytic enzyme biomarkers for diagnosis and detection of brain and/or CNS injury or neural disorders are at least about 100 amino acids longer either at the N-Terminal and/or C-Terminal of the peptides identified by SEQ ID NO's: 1-149. Preferably the peptides identified as targets for proteolytic enzyme biomarkers for diagnosis and detection of brain and/or CNS injury or neural disorders are at least about 200 amino acids longer either at the N-Terminal and/or C-Terminal of the peptides identified by SEQ ID NO's: 1-149. Preferably the peptides identified as targets for proteolytic enzyme biomarkers for diagnosis and detection of brain and/or CNS injury or neural disorders are up to about 400 amino acids longer either at the N-Terminal and/or C-Terminal of the peptides identified by SEQ ID NO's: 1-149. Examples of longer amino acids are found in Table 1, along with their accession numbers. The desired amino acids to be included at either the N- or C-terminal of each biomarker identified by SEQ ID NO's.: 1-149 are thus readily determined.

In a preferred embodiment, peptides identified as targets for proteolytic enzyme biomarkers for diagnosis and detection of brain and/or CNS/PNS injury or neural disorders, preferably are derived from axonal proteins such as for example, NF-200 (NF-H), NF-160 (NF-M), NF-68 (NF-L), peptides, fragments or derivatives thereof.

In another preferred embodiment, peptides identified as targets for proteolytic enzyme biomarkers for diagnosis and detection of brain and/or CNS injury or neural disorders, preferably are peptides of amyloid precursor protein fragments and derivatives thereof.

In another preferred embodiment, peptides identified as targets for proteolytic enzyme biomarkers for diagnosis and detection of brain and/or CNS injury or neural disorders, preferably are dendritic peptides, such as for example: peptides of alpha-tubulin (P02551), beta-tubulin (P0 4691), MAP-2A/B, MAP-2C, Tau, Dynamin-1 (P21575), Dynactin (Q13561), P24.

In another preferred embodiment, peptides identified as targets for proteolytic enzyme biomarkers for diagnosis and detection of brain and/or CNS/PNS injury or neural disorders, preferably are somal peptides, for example: peptides, of UCH-L1 (Q00981), PEBP (P31044), NSE (P07323), Thy 1.1, Prion, Huntington fragments and derivatives thereof.

In another preferred embodiment, peptides identified as targets for proteolytic enzyme biomarkers for diagnosis and detection of brain and/or CNS/PNS injury or neural disorders, preferably are presynaptic peptides of synapsin-1, synapsin-2, alpha-synuclein (P37377), beta-synuclein (Q63754), GAP43, synaptophysin, synaptotagmin (P21707), syntaxin fragments and derivatives thereof.

In another preferred embodiment, peptides identified as targets for proteolytic enzyme biomarkers for diagnosis and detection of brain and/or CNS/PNS injury or neural disorders, preferably are post-synaptic peptides derived from PSD95, PSD93, NMDA-receptor (including all subtypes).

In another preferred embodiment, peptides identified as targets for proteolytic enzyme biomarkers for diagnosis and detection of brain and/or CNS/PNS injury or neural disorders, preferably are demyelination peptides, such as for example, peptides of myelin basic protein (MBP), myelin proteolipid protein, fragments and derivatives thereof.

In another preferred embodiment, peptides identified as targets for proteolytic enzyme biomarkers for diagnosis and detection of brain and/or CNS/PNS injury or neural disorders, preferably are glial peptides, for example, peptides of GFAP (P47819), protein disulfide isomerase (PDI-P04785), fragments and derivatives thereof.

In another preferred embodiment, peptides identified as targets for proteolytic enzyme biomarkers for diagnosis and detection of brain and/or CNS/PNS injury or neural disorders, preferably are cholinergic peptides, such as for example, peptides of acetylcholine esterase, choline acetyltransferase, fragments and derivatives thereof.

In another preferred embodiment, peptides identified as targets for proteolytic enzyme biomarkers for diagnosis and detection of brain and/or CNS/PNS injury or neural disorders, preferably are dopaminergic peptides, such as for example, peptides of tyrosine hydroxylase (TH), phospho-TH, DARPP32, fragments and derivatives thereof.

In another preferred embodiment, peptides identified as targets for proteolytic enzyme biomarkers for diagnosis and detection of brain and/or CNS/PNS injury or neural disorders, preferably are noradrenergic peptides, such as for example, peptides of dopamine beta-hydroxylase (DbH), fragments and derivatives thereof.

In another preferred embodiment, peptides identified as targets for proteolytic enzyme biomarkers for diagnosis and detection of brain and/or CNS/PNS injury or neural disorders, preferably are serotonergic peptides, such as for example, peptides of tryptophan hydroxylase (TrH) fragments and derivatives thereof.

In another preferred embodiment, peptides identified as targets for proteolytic enzyme biomarkers for diagnosis and detection of brain and/or CNS/PNS injury or neural disorders, preferably are glutamatergic peptides, such as for example, peptides of glutaminase, glutamine synthetase, fragments and derivatives thereof.

In another preferred embodiment, peptides identified as targets for proteolytic enzyme biomarkers for diagnosis and detection of brain and/or CNS/PNS injury or neural disorders, preferably are GABAergic peptides, such as for example, peptides of GABA transaminase (4-aminobutyrate-2-ketoglutarate transaminase [GABAT]), glutamic acid decarboxylase (GAD25, 44, 65, 67), fragments and derivatives thereof.

In another preferred embodiment, peptides identified as targets for proteolytic enzyme biomarkers for diagnosis and detection of brain and/or CNS/PNS injury or neural disorders, preferably are neurotransmitter peptide receptors, such as for example, peptides of beta-adrenoreceptor subtypes, (e.g. beta (2)), alpha-adrenoreceptor subtypes, (e.g. (alpha (2c)), GABA receptors (e.g. GABA(B)), metabotropic glutamate receptor (e.g. mGluR3), NMDA receptor subunits (e.g. NR1A2B), Glutamate receptor subunits (e.g. GluR4), 5-HT serotonin receptors (e.g. 5-HT(3)), dopamine receptors (e.g. D4), muscarinic Ach receptors (e.g. M1), nicotinic acetylcholine receptor (e.g. alpha-7), fragments or derivatives thereof.

In another preferred embodiment, peptides identified as targets for proteolytic enzyme biomarkers for diagnosis and detection of brain and/or CNS/PNS injury or neural disorders, preferably are neurotransmitter transporter peptides, such as for example, peptides of norepinephrine transporter (NET), dopamine transporter (DAT), serotonin transporter (SERT), vesicular transporter proteins (VMAT1 and VMAT2), GABA transporter vesicular inhibitory amino acid transporter (VIAAT/VGAT), glutamate transporter (e.g. GLT1), vesicular acetylcholine transporter, choline transporter (e.g. CHT1), fragments, or derivatives thereof.

In another preferred embodiment, peptides identified as targets for proteolytic enzyme biomarkers for diagnosis and detection of brain and/or CNS/PNS injury or neural disorders, include, but are not limited to, vimentin (P31000), CK-BB (P07335), 14-3-3-epsilon (P42655), MMP2, MMP9, fragments or derivatives thereof.

In another preferred embodiment, peptides identified as targets for proteolytic enzyme biomarkers for diagnosis and detection of cardiac injury are for example troponins, such as troponin-I, troponin-T and troponin-C.

In another preferred embodiment, proteolytic enzyme biomarkers are detected from samples of a patient who is susceptible to or suffering from cancer, neuronal injury, and/or organ injury.

The markers are characterized by molecular weight, enzyme digested fingerprints and by their known protein identities. The markers can be resolved from other peptides in a sample by using a variety of fractionation techniques, e.g., chromatographic separation coupled with mass spectrometry, or by traditional immunoassays. In preferred embodiments, the method of resolution involves Surface-Enhanced Laser Desorption/Ionization ("SELDI") mass spectrometry, in which the surface of the mass spectrometry probe comprises adsorbents that bind the markers.

In another preferred embodiment, the presence of certain proteolytic enzyme biomarkers is indicative of the extent of CNS/PNS and/or brain injury. For example, detection of one or more dendritic damage markers, soma injury markers, demyelination markers, or axonal injury markers would be indicative of CNS injury and the presence of one or more would be indicative of the extent of nerve injury.

In another preferred embodiment, the presence of certain degraded neural proteins is indicative of proteolytic enzyme activity and is indicative of a neurological disorder, i.e. dendritic damage markers, soma injury markers, demyelination markers, axonal injury markers, synaptic terminal markers, and post-synaptic markers.

Preferred methods for detection and diagnosis of CNS/PNS and/or brain injury comprise detecting at least one or more proteolytic enzyme biomarkers in a subject sample, and; correlating the detection of one or more proteolytic enzyme biomarkers with a diagnosis of CNS and/or brain injury, wherein the correlation takes into account the detection of one or more proteolytic enzyme biomarker in each diagnosis, as compared to normal subjects. Preferably, the proteolytic enzyme biomarkers are specific; for example, neuronal proteins, tumor antigens, wherein the one or more proteolytic enzyme biomarkers degrade proteins selected from: neural proteins, such as for example, axonal proteins—NF-200 (NF-H), NF-160 (NF-M), NF-68 (NF-L); amyloid precursor protein; dendritic proteins—alpha-tubulin (P02551), beta-tubulin (P0 4691), MAP-2A/B, MAP-2C, Tau, Dynamin-1 (P21575), Dynactin (Q13561), P24; somal proteins—UCH-L1 (Q00981), PEBP (P31044), NSE (P07323), Thy 1.1, Prion, Huntington; presynaptic proteins—synapsin-1, synapsin-2, alpha-synuclein (p37377), beta-synuclein (Q63754), GAP43, synaptophysin, synaptotagmin (P21707), syntaxin; post-synaptic proteins—PSD95, PSD93, NMDA-receptor (including all subtypes); demyelination biomarkers—myelin basic protein (MBP), myelin proteolipid protein; glial proteins—GFAP (P47819), protein disulfide isomerase (PDI-P04785); neurotransmitter biomarkers—cholinergic biomarkers: acetylcholine esterase, choline acetyltransferase; dopaminergic biomarkers—tyrosine hydroxylase (TH), phospho-TH, DARPP32; noradrenergic biomarkers—dopamine beta-hydroxylase (DbH); serotonergic biomarkers—tryptophan hydroxylase (TrH); glutamatergic biomarkers—glutaminase, glutamine synthetase; GABAergic biomarkers—GABA transaminase (4-aminobutyrate-2-ketoglutarate transaminase [GABAT]), glutamic acid decarboxylase (GAD25, 44, 65, 67); neurotransmitter receptors—beta-adrenoreceptor subtypes, (e.g. beta (2)), alpha-adrenoreceptor subtypes, (e.g. (alpha (2c)), GABA receptors (e.g. GABA(B)), metabotropic glutamate receptor (e.g. mGluR3), NMDA receptor subunits (e.g. NR1A2B), Glutamate receptor subunits (e.g. GluR4), 5-HT serotonin receptors (e.g. 5-HT(3)), dopamine receptors (e.g. D4), muscarinic Ach receptors (e.g. M1), nicotinic acetylcholine receptor (e.g. alpha-7); neurotransmitter transporters—norepinephrine transporter (NET), dopamine transporter (DAT), serotonin transporter (SERT), vesicular transporter proteins (VMAT1 and VMAT2), GABA transporter vesicular inhibitory amino acid transporter (VIAAT/VGAT), glutamate transporter (e.g. GLT1), vesicular acetylcholine transporter, choline transporter (e.g. CHT1); other protein biomarkers include, but not limited to vimentin (P31000), CK-BB (P07335), 14-3-3-epsilon (P42655), MMP2, MMP9.

In another preferred embodiment, antibodies specific for the proteolytic products of enzyme biomarkers bind to epitopes as identified by SEQ ID NO's: 1-149.

In another preferred embodiment, antibodies specific for the proteolytic products of enzyme biomarkers bind to epitopes that are about 50% homologous to sequences identified by SEQ ID NO's: 1-149; more preferably antibodies specific for the proteolytic products of enzyme biomarkers bind to epitopes that are about 70% homologous to sequences identified by SEQ ID NO's: 1-149; more preferably antibodies specific for the proteolytic products of enzyme biomarkers bind to epitopes that are about 80% homologous to sequences identified by SEQ ID NO's: 1-149; more preferably antibodies specific for the proteolytic products of enzyme biomarkers bind to epitopes that are about 90%, 95%, 96%, 97%, 95%, 99% or 99.9% homologous to sequences identified by SEQ ID NO's: 1-149.

In another preferred embodiment, antibodies specific for the proteolytic products of enzyme biomarkers bind to epitopes at least about 10 amino acids longer at either the N-terminal and/or C-terminal of the epitopes as identified by SEQ ID NO's: 1-149; more preferably, antibodies specific for the proteolytic products of enzyme biomarkers bind to epitopes at least about 20 amino acids longer at either the N-terminal and/or C-terminal of the epitopes as identified by SEQ ID NO's: 1-149; more preferably, antibodies specific for the proteolytic products of enzyme biomarkers bind to epitopes at least about 50 amino acids longer at either the N-terminal and/or C-terminal of the epitopes as identified by SEQ ID NO's: 1-149; more preferably, antibodies specific for the proteolytic products of enzyme biomarkers bind to epitopes at least about 100 amino acids longer at either the N-terminal and/or C-terminal of the epitopes as identified by SEQ ID NO's: 1-149; more preferably, antibodies specific for the proteolytic products of enzyme biomarkers bind to epitopes at least about 200 amino acids longer at either the N-terminal and/or C-terminal of the epitopes as identified by SEQ ID NO's: 1-149; more preferably, antibodies specific for the proteolytic products of enzyme biomarkers bind to epitopes up to at least about 500 amino acids longer at either the N-terminal and/or C-terminal of the epitopes as identified by SEQ ID NO's: 1-149. Examples of longer amino acids are found in Table 1, along with their accession numbers. The desired amino acids to be included at either the N- or C-terminal of each biomarker identified by SEQ ID NO's.: 1-149 are thus readily determined and antibodies can be produced.

In another preferred embodiment, the invention provides a kit for analyzing cell damage in a subject. The kit, preferably includes: (a) a composition or panel of biomarkers as identified by anyone of SEQ ID NO's.: 1-49 (b) a substrate for holding a biological sample isolated from a human subject suspected of having a damaged nerve cell; (c) an agent that specifically binds at least one or more of the proteolytic enzymes; and (d) printed instructions for reacting the agent with the biological sample or a portion of the biological sample to detect the presence or amount of at least one marker in the biological sample.

Preferably, the biological sample is a fluid in communication with the nervous system of the subject prior to being isolated from the subject; for example, CSF or blood, and the agent can be an antibody, aptamer, or other molecule that specifically binds at least one or more of the proteolytic enzymes. The kit can also include a detectable label such as one conjugated to the agent, or one conjugated to a substance that specifically binds to the agent (e.g., a secondary antibody).

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

In FIG. 4A, anti-total MBP antibody detects intact MBP-21 kDa and MBP-18 kDa in naïve brain and the 12 kDa and 10 kDa fragments (BDP-12 kDa, BDP-10 kDa) in the TBI brain. In FIGS. 4B and 4C, only BDP-12 kDa and BDP-10 kDa were detected; no intact MBP's (18 kDa and 21 kDa) were detected with these antibodies, demonstrating their high selectivity for the in vivo generated MBP fragments.

DETAILED DESCRIPTION

Figure 1:
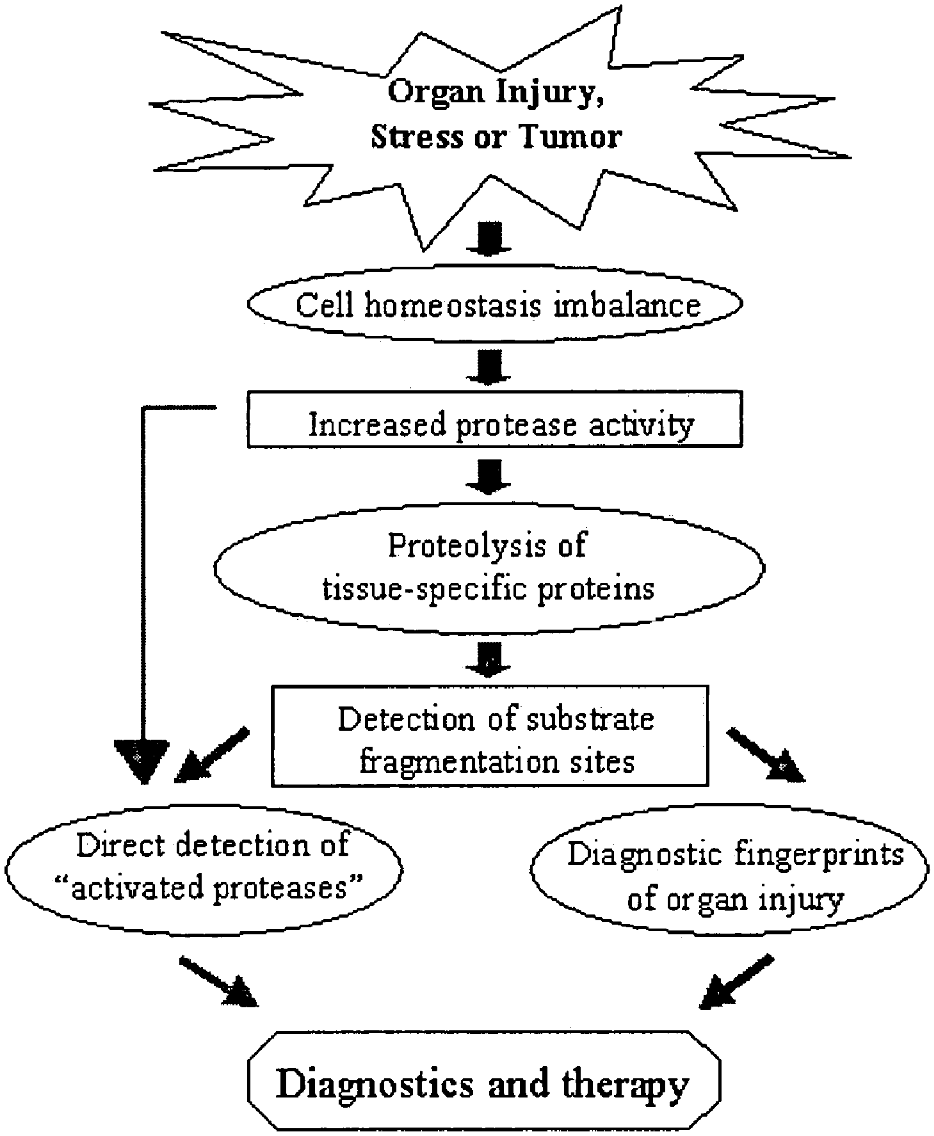
FIG. 1 is a diagrammatic illustration showing an example of a method relating to diagnostics and therapy following organ stress or injury. Organ stress or injury and tumor formation or treatment induce increased proteolytic activities which result in unique tissue protein fragments of diagnostic values.

The present invention identifies biomarkers that are diagnostic of CNS, muscle or other organ cell injury and/or stress and/or neuronal disorders. Detection of different biomarkers of the invention are also diagnostic of the degree of severity of nerve injury, the cell(s) involved in the injury, and the subcellular localization of the injury. In particular, the invention employs a step of correlating the presence or amount of one or more proteolytic enzymes which are activated by the presence of peptide(s) from neural cells and/or organs due to injury. The presence of proteolytic enzymes is correlated with the severity and/or type of nerve cell injury and/or organ. The activity of a proteolytic enzyme and the generation of tissue protein breakdown products directly relate to severity of nerve tissue and/or organ injury as a more severe injury damages a greater number of cells which in turn causes a larger amount of neural or cellular peptide(s) to accumulate in the biological sample (e.g., CSF), thereby activating the proteolytic enzymes.

DEFINITIONS

Prior to setting forth the invention, it may be helpful to an understanding thereof to set forth definitions of certain terms that will be used hereinafter.

"Marker" in the context of the present invention refers to a polypeptide (of a particular apparent molecular weight) which is differentially present in a sample taken from patients having neural injury and/or neuronal disorders as compared to a comparable sample taken from control subjects (e.g., a person with a negative diagnosis, normal or healthy subject).

"Activity" of an enzyme is the amount of product produced per unit time at a fixed temperature and pH.

"Specific activity" of an enzyme is the amount of product produced per unit time per mg protein.

"Substrate" is the target protein that the enzyme catalyzes. The International Union of Biochemistry (I.U.B.) initiated standards of enzyme nomenclature which recommend that enzyme names indicate both the substrate acted upon and the type of reaction catalyzed. For example, under this system, the enzyme uricase is called urate: $O_2$ oxidoreductase, while the enzyme glutamic oxaloacetic transaminase (GOT) is called L-aspartate: 2-oxoglutarate aminotransferase.

"Complementary" in the context of the present invention refers to detection of at least two biomarkers, which when detected together provides increased sensitivity and specificity as compared to detection of one biomarker alone.

The phrase "differentially present" refers to differences in the quantity and/or the frequency of a marker present in a sample taken from patients having for example, neural injury as compared to a control subject. For example, a marker can be a polypeptide which is present at an elevated level or at a decreased level in samples of patients with neural injury compared to samples of control subjects. Alternatively, a marker can be a polypeptide which is detected at a higher frequency or at a lower frequency in samples of patients compared to samples of control subjects. A marker can be differentially present in terms of quantity, frequency or both.

A polypeptide is differentially present between the two samples if the amount of the polypeptide in one sample is statistically significantly different from the amount of the polypeptide in the other sample. For example, a polypeptide is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polypeptide is differentially present between the two sets of samples if the frequency of detecting the polypeptide in samples patients suffering from neural injury and/or neuronal disorders, is statistically significantly higher or lower than in the control samples. For example, a polypeptide is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

"Diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "test amount" of a marker refers to an amount of a marker present in a sample being tested. A test amount can be either in absolute amount (e.g., μg/ml) or a relative amount (e.g., relative intensity of signals).

A "diagnostic amount" of a marker refers to an amount of a marker in a subject's sample that is consistent with a diagnosis of neural injury and/or neuronal disorder. A diagnostic amount can be either in absolute amount (e.g., μg/ml) or a relative amount (e.g., relative intensity of signals).

A "control amount" of a marker can be any amount or a range of amount which is to be compared against a test amount of a marker. For example, a control amount of a marker can be the amount of a marker in a person without neural injury and/or neuronal disorder. A control amount can be either in absolute amount (e.g., μg/ml) or a relative amount (e.g., relative intensity of signals).

"Probe" refers to a device that is removably insertable into a gas phase ion spectrometer and comprises a substrate having a surface for presenting a marker for detection. A probe can comprise a single substrate or a plurality of substrates.

"Substrate" or "probe substrate" refers to a solid phase onto which an adsorbent can be provided (e.g., by attachment, deposition, etc.).

"Adsorbent" refers to any material capable of adsorbing a marker. The term "adsorbent" is used herein to refer both to a single material ("monoplex adsorbent") (e.g., a compound or functional group) to which the marker is exposed, and to a plurality of different materials ("multiplex adsorbent") to which the marker is exposed. The adsorbent materials in a multiplex adsorbent are referred to as "adsorbent species." For example, an addressable location on a probe substrate can comprise a multiplex adsorbent characterized by many different adsorbent species (e.g., anion exchange materials, metal chelators, or antibodies), having different binding characteristics. Substrate material itself can also contribute to adsorbing a marker and may be considered part of an "adsorbent."

"Adsorption" or "retention" refers to the detectable binding between an adsorbant and a marker either before or after washing with an eluant (selectivity threshold modifier) or a washing solution.

"Eluant" or "washing solution" refers to an agent that can be used to mediate adsorption of a marker to an adsorbent. Eluants and washing solutions are also referred to as "selectivity threshold modifiers." Eluants and washing solutions can be used to wash and remove unbound materials from the probe substrate surface.

"Resolve," "resolution," or "resolution of marker" refers to the detection of at least one marker in a sample. Resolution includes the detection of a plurality of markers in a sample by separation and subsequent differential detection. Resolution does not require the complete separation of one or more markers from all other biomolecules in a mixture. Rather, any separation that allows the distinction between at least one marker and other biomolecules suffices.

"Gas phase ion spectrometer" refers to an apparatus that measures a parameter which can be translated into mass-to-charge ratios of ions formed when a sample is volatilized and ionized. Generally ions of interest bear a single charge, and mass-to-charge ratios are often simply referred to as mass. Gas phase ion spectrometers include, for example, mass spectrometers, ion mobility spectrometers, and total ion current measuring devices.

"Mass spectrometer" refers to a gas phase ion spectrometer that includes an inlet system, an ionization source, an ion optic assembly, a mass analyzer, and a detector.

"Laser desorption mass spectrometer" refers to a mass spectrometer which uses laser as means to desorb, volatilize, and ionize an analyte.

"Detect" refers to identifying the presence, absence or amount of the object to be detected.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, or flow cytometry.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and $F(ab)'_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

"Immunoassay" is an assay that uses an antibody to specifically bind an antigen (e.g., a marker). The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker NF-200 from specific species such as rat, mouse, or human can be selected to obtain only those polyclonal antibodies that are specifically immunoreactive with marker NF-200 and not with other proteins, except for polymorphic variants and alleles of marker NF-200. This selection may be achieved by subtracting out antibodies that cross-react with marker NF-200 molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

"Energy absorbing molecule" or "EAM" refers to a molecule that absorbs energy from an ionization source in a mass spectrometer thereby aiding desorption of analyte, such as a marker, from a probe surface. Depending on the size and nature of the analyte, the energy absorbing molecule can be optionally used. Energy absorbing molecules used in MALDI are frequently referred to as "matrix." Cinnamic acid derivatives, sinapinic acid ("SPA"), cyano hydroxy cinnamic acid ("CHCA") and dihydroxybenzoic acid are frequently used as energy absorbing molecules in laser desorption of bioorganic molecules.

"Sample" is used herein in its broadest sense. A sample comprising polynucleotides, polypeptides, peptides, antibodies fragments and derivatives thereof may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; fragments and derivatives thereof.

"Substantially purified" refers to nucleic acid molecules or proteins that are removed from their natural environment and are isolated or separated, and are at least about 60% free, preferably about 75% free, and most preferably about 90% free, from other components with which they are naturally associated.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

As used herein, the term "fragment or segment", as applied to a nucleic acid sequence, gene or polypeptide, will ordinarily be at least about 5 contiguous nucleic acid bases (for nucleic acid sequence or gene) or amino acids (for polypeptides), typically at least about 10 contiguous nucleic acid bases or amino acids, more typically at least about 20 contiguous nucleic acid bases or amino acids, usually at least about 30 contiguous nucleic acid bases or amino acids, preferably at least about 40 contiguous nucleic acid bases or amino acids, more preferably at least about 50 contiguous nucleic acid bases or amino acids, and even more preferably at least about 60 to 80 or more contiguous nucleic acid bases or amino acids in length. "Overlapping fragments" as used herein, refer to contiguous nucleic acid or peptide fragments which begin at the amino terminal end of a nucleic acid or protein and end at the carboxy terminal end of the nucleic acid or protein. Each nucleic acid or peptide fragment has at least about one contiguous nucleic acid or amino acid position in common with the next nucleic acid or peptide fragment, more preferably at least about three contiguous nucleic acid bases or amino acid positions in common, most preferably at least about ten contiguous nucleic acid bases or amino acid positions in common.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides.

As used herein, the terms "polypeptide" or "peptide" encompass amino acid chains of any length, including full length proteins recited herein.

As used herein, "peptides or epitopes with longer amino sequences" encompasses amino acid chains of any length, including full length proteins recited herein. Preferably, the antibodies produced bind epitopes that comprise at least about 3 amino acids long. In other preferred embodiments, the term "the proteolytic products of enzyme biomarkers bind to epitopes at least about 10 amino acids longer than the epitopes as identified by SEQ ID NO's: 1-149" includes an amino acid chain of 10 amino acids at the amino-terminal and/or the carboxy terminal of a desired peptide. Examples of longer amino acids are found in Table 1, along with their accession numbers. The desired amino acids to be included at either the N- or C-terminal of each biomarker identified by SEQ ID NO's.: 1-149 are thus, readily determined.

As used herein, "variant" or "derivative" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base.

"Stringency" is meant the combination of conditions to which nucleic acids are subject that cause the duplex to dissociate, such as temperature, ionic strength, and concentration of additives such as formamide. Conditions that are more likely to cause the duplex to dissociate are called "higher stringency", e.g. higher temperature, lower ionic strength and higher concentration of formamide.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C.

For certain applications, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

The phrase "hybridizing conditions" and its grammatical equivalents, when used with a maintenance time period, indicates subjecting the hybridization reaction admixture, in context of the concentration of the reactants and accompanying reagents in the admixture, to time, temperature, pH conditions sufficient to allow the polynucleotide probe to anneal with the target sequence, typically to form the nucleic acid duplex. Such time, temperature and pH conditions required to accomplish the hybridization depend, as is well known in the art, on the length of the polynucleotide probe to be hybridized, the degree of complementarity between the polynucleotide probe and the target, the guanidine and cytosine content of the polynucleotide, the stringency of the hybridization desired, and the presence of salts or additional reagents in the hybridization reaction admixture as may affect the kinetics of hybridization. Methods for optimizing hybridization conditions for a given hybridization reaction admixture are well known in the art.

As used herein, the term "injury or neural injury" is intended to include a damage which directly or indirectly affects the normal functioning of the CNS or PNS. For example, the injury can be damage to retinal ganglion cells; a traumatic brain injury; a stroke related injury; a cerebral aneurism related injury; demyelinating diseases such as multiple sclerosis; a spinal cord injury, including monoplegia, diplegia, paraplegia, hemiplegia and quadriplegia; a neuroproliferative disorder or neuropathic pain syndrome. Examples of CNS injuries or disease include TBI, stroke, concussion (including post-concussion syndrome), cerebral ischemia, neurodegenerative diseases of the brain such as Parkinson's disease, Dementia Pugilistica, Huntington's disease and Alzheimer's disease, brain injuries secondary to seizures which are induced by radiation, exposure to ionizing or iron plasma, nerve agents, cyanide, toxic concentrations of oxygen, neurotoxicity due to CNS malaria or treatment with anti-malaria agents, malaria pathogens, injury due to trypanosomes, and other CNS traumas. Examples of PNS injuries or diseases include neuropathies induced either by toxins (e.g. cancer chemotherapeutic agents) diabetes, peripheral trauma or any process that produced pathological destruction of peripheral nerves and/or their myelin sheaths.

As used herein, the term "stroke" is art recognized and is intended to include sudden diminution or loss of consciousness, sensation, and voluntary motion caused by rapture rupture or obstruction (e.g. by a blood clot) of an artery of the brain.

As used herein, the term "Traumatic Brain Injury" is art recognized and is intended to include the condition in which, a traumatic blow to the head causes damage to the brain, often without penetrating the skull. Usually, the initial trauma can result in expanding hematoma, subarachnoid hemorrhage, cerebral edema, raised intracranial pressure (ICP), and cerebral hypoxia, which can, in turn, lead to severe secondary events due to low cerebral blood flow (CBF).

"Neural cells" as defined herein, are cells that reside in the brain, central and peripheral nerve systems, including, but not limited to, nerve cells, glial cell, oligodendrocyte, microglia cells or neural stem cells.

"Neuronal specific or neuronally enriched proteins" are defined herein, as proteins that are present in neural cells and not in non-neuronal cells, such as, for example, cardiomyocytes, myocytes, in skeletal muscles, hepatocytes, kidney cells and cells in testis. Non-limiting examples of neural proteins from which peptides can be derived via, for example, enzyme degradation, are shown in Table 1 below.

"Neural (neuronal) defects, disorders or diseases" as used herein refers to any neurological disorder, including but not limited to neurodegenerative disorders (Parkinson's; Alzheimer's) or autoimmune disorders (multiple sclerosis) of the central nervous system; memory loss; long term and short term memory disorders; learning disorders; autism, depression, benign forgetfulness, childhood learning disorders, close head injury, and attention deficit disorder; autoimmune disorders of the brain, neuronal reaction to viral infection; brain damage; depression; psychiatric disorders such as bipolarism, schizophrenia; narcolepsy/sleep disorders (including circadian rhythm disorders, insomnia and narcolepsy); severance of nerves or nerve damage; severance of the cerebrospinal nerve cord (CNS) and any damage to brain or nerve cells; neurological deficits associated with AIDS; tics (e.g. Giles de la Tourette's syndrome); Huntington's chorea, schizophrenia, traumatic brain injury, tinnitus, neuralgia, especially trigeminal neuralgia, neuropathic pain, inappropriate neuronal activity resulting in neurodysthesias in diseases such as diabetes, MS and motor neuron disease, ataxias, muscular rigidity (spasticity) and temporomandibular joint dysfunction; Reward Deficiency Syndrome (RDS) behaviors in a subject.

As used herein, "RDS" behaviors are those behaviors that manifest as one or more behavioral disorders related to an individual's feeling of well-being with anxiety, anger or a craving for a substance. RDS behaviors include, alcoholism, SUD, smoking, BMI or obesity, pathological gambling, carbohydrate bingeing, axis 11 diagnosis, SAB, ADD/ADHD, CD, TS, family history of SUD, and Obesity. All these behaviors, and others described herein as associated with RDS behaviors or genes involved in the neurological pathways related to RDS, are included as RDS behaviors as part of this invention. Additionally, many of the clinical terms used herein for many specific disorders that are RDS disorders are found in the Quick Reference to the Diagnostic Criteria From DSM-IV™, The American Psychiatric Association, Washington, D.C., 1994.

Affective disorders, including major depression, and the bipolar, manic-depressive illness, are characterized by changes in mood as the primary clinical manifestation. Major depression is the most common of the significant mental illnesses, and it must be distinguished clinically from periods of normal grief, sadness and disappointment, and the related dysphoria or demoralization frequently associated with medical illness. Depression is characterized by feelings of intense sadness, and despair, mental slowing and loss of concentration, pessimistic worry, agitation, and self-deprecation. Physical changes can also occur, including insomnia, anorexia, and weight loss, decreased energy and libido, and disruption of hormonal circadian rhythms.

Mania, as well as depression, is characterized by changes in mood as the primary symptom. Either of these two extremes of mood may be accompanied by psychosis with disordered thought and delusional perceptions. Psychosis may have, as a secondary symptom, a change in mood, and it is this overlap with depression that causes much confusion in diagnosis. Severe mood changes without psychosis frequently occur in depression and are often accompanied by anxiety.

Parkinson's disease, independent of a specific etiology, is a chronic, progressive central nervous system disorder which usually appears insidiously in the latter decades of life. The disease produces a slowly increasing disability in purposeful movement. It is characterized by four major clinical features of tremor, bradykinesia, rigidity and a disturbance of posture. Often patients have an accompanying dementia. In idiopathic Parkinsonism, there is usually a loss of cells in the substantia nigra, locus ceruleus, and other pigmented neurons of the brain, and a decrease of dopamine content in nerve axon terminals of cells projecting from the substantia nigra. The understanding that Parkinsonism is a syndrome of dopamine deficiency and the discovery of levodopa as an important drug for the treatment of the disease were the logical culmination of a series of related basic and clinical observations, which serves as the rationale for drug treatment.

The term "Alzheimer's Disease" refers to a progressive mental deterioration manifested by memory loss, confusion and disorientation beginning in late middle life and typically resulting in death in five to ten years. Pathologically, Alzheimer's Disease can be characterized by thickening, conglutination, and distortion of the intracellular neurofibrils, neurofibrillary tangles and senile plaques composed of granular or filamentous argentophilic masses with an amyloid core. Diagnosing Alzheimer's Disease: the National Institute of Neurological and Communicative Disorders and Stroke-Alzheimer's Disease and the Alzheimer's Disease and Related Disorders Association (NINCDS-ADRDA) criteria can be used to diagnose Alzheimer's Disease (McKhann et al., 1984, Neurology 34:939-944). The patient's cognitive function can be assessed by the Alzheimer's Disease Assessment Scale-cognitive subscale (ADAS-cog; Rosen et al., 1984, Am. J. Psychiatry 141:1356-1364).

As used herein, the term "autism" refers to a state of mental introversion characterized by morbid self-absorption, social failure, language delay, and stereotyped behavior.

As used herein, the term "depression" refers to a clinical syndrome that includes a persistent sad mood or loss of interest in activities, which lasts for at least two weeks in the absence of treatment.

The term "benign forgetfulness," as used herein, refers to a mild tendency to be unable to retrieve or recall information that was once registered, learned, and stored in memory (e.g., an inability to remember where one placed one's keys or parked one's car). Benign forgetfulness typically affects individuals after 40 years of age and can be recognized by standard assessment instruments such as the Wechsler Memory Scale (Russell, 1975, *J. Consult Clin. Psychol.* 43:800-809).

As used herein, the term "childhood learning disorders" refers to an impaired ability to learn, as experienced by certain children.

The term "close head injury," as used herein, refers to a clinical condition after head injury or trauma which condition can be characterized by cognitive and memory impairment.

The term "attention deficit disorder," as used herein, refers to a disorder that is most commonly exhibited by children and which can be characterized by increased motor activity and a decreased attention span. Attention-deficit disorder ("ADD") is a common behavioral learning disorder in children which adversely affects school performance and family relationships. Symptoms and signs include hyperactivity (e.g., ADDH and AD/HD, DSM-IV), impulsivity, emotional lability, motor incoordination and some perceptual difficulties. Treatment has included psychostimulants, which while effective are controversial, and may cause troubling side effects such as dysphoria, headache and growth retardation. Other drugs, including the tricyclic antidepressants, appear to improve attention, but may be less effective than the psychostimulants.

As used herein, "subcellular localization" refers to defined subcellular structures within a single nerve cell. These subcellularly defined structures are matched with unique neural proteins derived from, for example, dendritic, axonal, myelin sheath, presynaptic terminal and postsynaptic locations. By monitoring the release of peptides unique to each of these regions, one can therefore monitor and define subcellular damage after brain injury. Furthermore, mature neurons are differentiated into dedicated subtype fusing a primary neural transmitter such as cholinergic (nicotinic and mucarinic), glutamatergic, gabaergic, serotonergic, dopaminergic. Each of this neuronal subtype express unique neural proteins such as those dedicated for the synthesis, metabolism and transporter and receptor of each unique neurotransmitter system (Table 1 below).

As used herein, a "pharmaceutically acceptable" component is one that is suitable for use with humans and/or animals without undue adverse side effects (such as toxicity, irritation, and allergic response) commensurate with a reasonable benefit/risk ratio.

The terms "patient" or "individual" are used interchangeably herein, and is meant a mammalian subject to be treated, with human patients being preferred. In some cases, the methods of the invention find use in experimental animals, in veterinary application, and in the development of vertebrate models for disease, including, but not limited to, rodents including mice, rats, and hamsters; birds, fish, reptiles, and primates.

As used herein, "ameliorated" or "treatment" refers to a symptom which is approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests. For example, amelioration or treatment of depression includes, for example, relief from the symptoms of depression which include, but are not limited to, changes in mood, feelings of intense sadness and despair, mental slowing, loss of concentration, pessimistic worry, agitation, and self-deprecation. Physical changes may also be relieved, including insomnia, anorexia and weight loss, decreased energy and libido, and the return of normal hormonal circadian rhythms. Another example, when using the terms "treating Parkinson's disease" or "ameliorating" as used herein means relief from the symptoms of Parkinson's disease which include, but are not limited to, tremor, bradykinesia, rigidity, and a disturbance of posture.

Proteolytic Markers

This disclosure describes the novel and highly practical use of proteolytic markers that can be detected in tissues, blood, cerebral spinal fluid (CSF) and other biological fluids (sweat, urine, saliva) for purposes of diagnosis and treatment following organ injury or tumor. Proteases are uniquely activated when cells are injured, stressed or chemically challenged. The over-activation of these proteases often contributes to cell death phenotypes, including apoptosis and oncosis (or oncotic necrosis) (see for example, FIG. 1). For instance, following traumatic brain injury (TBI), stroke and renal ischemia, calpains I and II become activated and, as a result, contribute to oncotic and apoptotic cell death. As well, activated caspases 3, 8 and 9 promote apoptosis in these same disease conditions. In fact, there are many proteases that are activated following organ injury, some of which include cathepsin B, L, and D, MMP2, 9, and 13, UCH-L1, ubiquitin binding proteases (UBP'S), chymase, tryptase and proteasome subunits (See Table 1). Table 1 shows non-limiting examples of potential proteolytic enzymes and protease-sensitive tissue protein markers. Each tissue protein marker in Table 1 can produce a proteolytic biomarker when cleaved by enzymes. Table 2 below shows non-limiting examples of unobvious and unique tissue protein cleavage sites produced by protease attack. For example, in a preferred embodiment, the invention provides biomarkers that are indicative of traumatic brain injury, neuronal damage, neural disorders, brain damage, neural damage due to drug or alcohol addiction, diseases associated with the brain or nervous system, such as the central and peripheral nervous systems (CNS, PNS). Preferably, the biomarkers are proteolytic enzymes which are activated as a result of damage to organs such as for example: heart, brain, liver, kidneys, lung, gut; neurons, central nervous system, peripheral nervous system, as well as skeletal muscles. Preferably the proteolytic enzymes are activated and cleave target proteins, peptides and fragments thereof due to neural and organ injury. Target proteins include, but are not limited to proteins, peptides or fragments thereof associated with neuronal cells, brain cells or any cell that is present in the brain and central nervous systems, organs such as heart, liver, kidneys and the like. Non-limiting examples of proteolytic enzymes that are detected upon neural and/or organ injury include (in alphabetical order): Achromopeptidase, Aminopeptidase, Ancrod, Angiotensin Converting Enzyme, Bromelain, Calpain, Calpain I, Calpain II, Carboxypeptidase A, Carboxypeptidase B, Carboxypeptidase G, Carboxypeptidase P, Carboxypeptidase W, Carboxypeptidase Y, Caspase, Caspase 1, Caspase 2, Caspase 3, Caspase 4, Caspase 5, Caspase 6, Caspase 7, Caspase 8, Caspase 9, Caspase 10, Caspase 13, Cathepsin B, Cathepsin C, Cathepsin D, Cathepsin G, Cathepsin H, Cathepsin L, Chymopapain, Chymase, Chymotrypsin, α-Clostripain, Collagenase, Complement C1r, Complement C1s, Complement Factor D, Complement factor 1, Cucumisin, Dipeptidyl peptidase IV, Elastase, leukocyte, Elastase, pancreatic, Endoproteinase Arg-C, Endoproteinase Asp-N, Endoproteinase Glu-C, Endoproteinase Lys-C, Enterokinase, Factor Xa, Ficin, Furin, Granzyme A, Granzyme B, HIV Protease, Igase, Kallikrein tissue, Kinase, Leucine Aminopeptidase (General), Leucine aminopeptidase, cytosol, Leucine aminopeptidase, microsomal, Matrix metalloprotease, Methionine Aminopeptidase, Neutrase, Papain, Pepsin, Plasmin, Prolidase, Pronase E, Prostate Specific Antigen, Protease, Protease S, Proteasomes, Proteinase, Proteinase 3, Proteinase A, Proteinase K, Protein C, Pyroglutamate aminopeptidase, Renin, Rennin, Thrombin, Tissue Plasminogen Activator, Troponins, Trypsin, Tryptase, Urokinase. Preferably, any one of SEQ ID NO's.: 1-148 are also detected.

By tracking the over-activation of these, and other proteases, one could diagnose and aid in the therapeutic treatment of organ diseases including, but not limited to, stroke or brain injury, renal failure, lung disease, heart attack and cataract formation. In case of cancerous tumors, there is likely to be increased cell death inside an active tumor, due to its rapid growth. Cell death is also significantly elevated during cancer treatment (e.g. chemotherapy) where the objective is to induce apoptosis of tumor cells. Thus, measuring protease activation (as a cell death index) would be a useful tool in tracking the progress of tumor growth and success of certain therapeutic treatments in treating cancer.

Two approaches to measure disease or medically induced protease activation will be used. The first is to track the activation of proteolytic enzymes directly. Because most proteases undergo proteolytic processing before becoming fully activated, truncation sites can be identified. With this knowledge, one could build specific tools to detect their activation; for example, we have already employed this type of technology with the use of an anti-activated calpain I antibody. This tool is particularly powerful if a protease is specifically or highly expressed in a distinct organ of interest. The second technological approach is to examine substrates that are cleaved by activated proteases (see Table 1). For instance, activated calpains cleave several proteins, including αII-spectrin, β1-spectrin, MAP2A/2B, synaptotagmin, tau, neurofilament H, M, and L and myelin basic protein. Armed with the knowledge of exact substrate cleavage sites, fragment-specific antibodies can be developed. Again, the power of this technique is particularly notable when a known tissue-specific substrate is cleaved, because this cleavage product can serve as a biomarker for that tissue type.

The advantages to measuring proteolytic markers in disease conditions are three-fold. I) The concept of excessive protease activation is a common theme in cancer and in many tissue and organ injuries, including, but not limited to, the brain, liver kidney, and heart. II) Many proteolytic products of activated proteases are released into biological fluids such blood, CSF, urine, sweat and saliva. Although their concentrations would be lower than the levels found directly within the originating injured tissue, they could still be detected (using antibodies or other capture agents), quantified and correlated with other outcome measures. III) The ability to use relatively non-invasive procedures to diagnose, treat and track patients is another powerful utility to using proteolytic markers in disease conditions.

In a preferred embodiment, detection of proteolytic enzymes that degrade one or more cleavage products is diagnostic of neural damage and/or neuronal disease. Examples of substrates of detected proteolytic enzymes include but are not limited to neural peptides, such as for example, axonal peptides—NF-200 (NF-H), NF-160 (NF-M), NF-68 (NF-L); amyloid precursor peptides; dendritic peptides—alpha-tubulin (P02551), beta-tubulin (P0 4691), MAP-2A/B, MAP-2C, Tau, Dynamin-1 (P21575), Dynactin (Q13561), P24; somal peptides—UCH-L1 (Q00981), PEBP (P31044), NSE (P07323), Thy 1.1, Prion, Huntington; presynaptic peptides—synapsin-1, synapsin-2, alpha-synuclein (p37377), beta-synuclein (Q63754), GAP43, synaptophysin, synaptotagmin (P21707), syntaxin; post-synaptic peptides—PSD95, PSD93, NMDA-receptor (including all subtypes); demyelination biomarkers—myelin basic peptides (MBP), myelin proteolipid peptides, glial peptides—GFAP (P47819), protein disulfide isomerase peptides (PDI-P04785); neurotransmitter biomarkers—cholinergic biomarkers: acetylcholine esterase peptides, choline acetyltransferase peptides; dopaminergic biomarkers—tyrosine hydroxylase peptides (TH), phospho-TH peptides, DARPP32 peptides; noradrenergic biomarkers—dopamine beta-hydroxylase peptides (DbH); serotonergic biomarkers—tryptophan hydroxylase peptides (TrH); glutamatergic biomarkers—glutaminase peptides, glutamine synthetase peptides; GABAergic biomarkers—GABA transaminase peptides (4-aminobutyrate-2-ketoglutarate transaminase [GABAT]), glutamic acid decarboxylase peptides (GAD25, 44, 65, 67); neurotransmitter receptors—beta-adrenoreceptor subtype peptides, (e.g. beta (2)), alpha-adrenoreceptor subtype peptides, (e.g. (alpha (2c)), peptides of GABA receptors (e.g. GABA(B)), peptides of metabotropic glutamate receptor (e.g. mGluR3), NMDA receptor subunit peptides (e.g. NR1A2B), Glutamate receptor subunit peptides (e.g. GluR4), peptides of 5-HT serotonin receptors (e.g. 5-HT(3)), peptides of dopamine receptors (e.g. D4), peptides of muscarinic Ach receptors (e.g. M1), peptides of nicotinic acetylcholine receptor (e.g. alpha-7); neurotransmitter transporters—peptides of norepinephrine transporter (NET), peptides of dopamine transporter (DAT), peptides of serotonin transporter (SERT), vesicular transporter peptides (VMAT1 and VMAT2), peptides of GABA transporter vesicular inhibitory amino acid transporter (VIAAT/VGAT), peptides of glutamate transporter (e.g. GLT1), peptides of vesicular acetylcholine transporter, peptides of choline transporter (e.g. CHT1); other peptide biomarkers include, but not limited to vimentin peptides (P31000), CK-BB peptides (P07335), 14-3-3-epsilon (P42655) peptides, MMP2 peptides, MMP9 peptides.

In another preferred embodiment, the proteolytic enzyme biomarkers have a specific activity for the neural proteins; for example, the non limiting examples listed in Table 1, about 1 μg to about 500 μg per 1 mg of substrate protein.

It has been shown experimentally that if the amount of the enzyme is kept constant and the substrate concentration is then gradually increased, the reaction velocity will increase until it reaches a maximum. After this point, increases in substrate concentration will not increase the velocity (delta A/delta T). It is theorized that when this maximum velocity had been reached, all of the available enzyme has been converted to ES, the enzyme substrate complex. This point is designated $V_{max}$. Using this maximum velocity and equation (7), Michaelis developed a set of mathematical expressions to calculate enzyme activity in terms of reaction speed from measurable laboratory data.

$$E + S \underset{K_{-1}}{\overset{K_{+1}}{\rightleftharpoons}} ES \underset{K_{-2}}{\overset{K_{+2}}{\rightleftharpoons}} P + E \qquad [7]$$

The Michaelis constant Km is defined as the substrate concentration at ½ the maximum velocity. Using this constant and the fact that Km can also be defined as:

$$Km = \frac{K^{+1} + K^{+2}}{K - 1} = [S]_{V\max/2}$$

$K_{+1}$, $K_{-1}$ and $K_{+2}$ being the rate constants from equation (7). Michaelis developed the following $$V_t = \frac{V_{\max}[S]}{K_m + [S]}$$

Where $V_t$=the velocity at any time

[S]=the substrate concentration at this time $V_{max}$=the highest under this set of experimental conditions (pH, temperature, etc.)

$K_m$=the Michaelis constant for the particular enzyme being investigated

Michaelis constants have been determined for many of the commonly used enzymes. A small Km indicates that the enzyme requires only a small amount of substrate to become saturated. Hence, the maximum velocity is reached at relatively low substrate concentrations. A large Km indicates the need for high substrate concentrations to achieve maximum reaction velocity.

The substrate with the lowest Km upon which the enzyme acts as a catalyst is frequently assumed to be enzyme's natural substrate, though this is not true for all enzymes.

Without wishing to be bound by theory, upon injury, structural and functional integrity of the cell membrane and blood brain barrier are compromised. Brain-specific and brain-enriched proteins, peptides or fragments thereof, are released into the extracellular space and subsequently into the CSF and blood. Proteolytic enzymes specific for these substrates are activated and cleave the substrate. Detection of one or more of these proteolytic enzyme biomarkers is indicative of neural and/or organ injury.

In a preferred embodiment, detection of at least one proteolytic enzyme specific for neural peptides released by injured neural cells and/or organs in CSF, blood, or other biological fluids, is diagnostic of the severity of brain injury and/or the monitoring of the progression of therapy. Preferably, the proteolytic enzyme markers are detected during the early stages of injury. An increase in the amount of proteolytic enzyme biomarkers fragments or derivatives thereof, in a patient suffering from a neural injury, neuronal disorder as compared to a normal healthy individual, will be diagnostic of a neural injury and/or neuronal disorder.

In a preferred embodiment, the invention provides biomarkers that are indicative of traumatic brain injury, neuronal damage to the CNS or PNS, neural disorders, brain damage, neural damage due to drug or alcohol addiction, diseases associated with the brain or nervous system, such as the central nervous system. Preferably, the biomarkers are proteolytic enzymes which are activated as a result of damage to organs such as for example: heart, brain, liver, kidneys; neurons, central nervous system, peripheral nervous system. Preferably the proteolytic enzymes are activated and cleave target proteins, peptides and fragments thereof due to neural and organ injury. Target proteins include, but are not limited to proteins, peptides or fragments thereof associated with neuronal cells, brain cells or any cell that is present in the brain and central nervous system, organs such as heart, liver, kidneys and the like. Non-limiting examples of proteolytic enzymes that are detected upon neural and/or organ injury include (in alphabetical order): Achromopeptidase, Aminopeptidase, Ancrod, Angiotensin Converting Enzyme, Bromelain, Calpain, Calpain I, Calpain II, Carboxypeptidase A, Carboxypeptidase B, Carboxypeptidase G, Carboxypeptidase P, Carboxypeptidase W, Carboxypeptidase Y, Caspase, Caspase 1, Caspase 2, Caspase 3, Caspase 4, Caspase 5, Caspase 6, Caspase 7, Caspase 8, Caspase 9, Caspase 10, Caspase 13, Cathepsin B, Cathepsin C, Cathepsin D, Cathepsin G, Cathepsin H, Cathepsin L, Chymopapain, Chymase, Chymotrypsin, α-Clostripain, Collagenase, Complement C1r, Complement C1s, Complement Factor D, Complement factor I, Cucumisin, Dipeptidyl peptidase IV, Elastase, leukocyte, Elastase, pancreatic, Endoproteinase Arg-C, Endoproteinase Asp-N, Endoproteinase Glu-C, Endoproteinase Lys-C, Enterokinase, Factor Xa, Ficin, Furin, Granzyme A, Granzyme B, HIV Protease, Igase, Kallikrein tissue, Kinase, Leucine Aminopeptidase (General), Leucine aminopeptidase, cytosol, Leucine aminopeptidase, microsomal, Matrix metalloprotease, Methionine Aminopeptidase, Neutrase, Papain, Pepsin, Plasmin, Prolidase, Pronase E, Prostate Specific Antigen, Protease, Protease S, Proteasomes, Proteinase, Proteinase 3, Proteinase A, Proteinase K, Protein C, Pyroglutamate aminopeptidase, Renin, Rennin, Thrombin, Tissue Plasminogen Activator, Troponins, Trypsin, Tryptase, Urokinase.

In another preferred embodiment, detection of at least one proteolytic enzyme, which has a neural peptide as a substrate, in CSF, blood, or other biological fluids, is diagnostic of the severity of injury following a variety of CNS insults, such as for example, stroke, spinal cord injury, or neurotoxicity caused by alcohol or substance abuse (e.g. ecstasy, methamphetamine, etc.).

The CNS comprises many brain-specific and brain-enriched peptides, fragments and derivatives thereof that are preferable substrates for proteolytic enzyme biomarkers in the diagnosis of brain injury, neural injury, neural disorders. Non-limiting examples of substrates for proteolytic enzymes are shown in Table 1. Table 2 shows non-limiting examples of unobvious and unique tissue protein cleavage sites produced by protease attack. (For example, SEQ ID NO's.: 1-149). For example, the proteolytic enzyme biomarkers are specific for neural specific proteins and can include axonal peptides such as neurofilament-heavy (NF-200), neurofilament-medium (NF-160), neurofilament-light (NF-68), and amyloid precursor peptides; dendritic peptides such as alpha-tubulin, beta-tubulin, MAP-2A/B/C. tau, dynamin-1, dynactin; and peptides found in the soma (cell body) including ubiquitin C-terminal hydrolase L1 peptides (UCH-L1), PEBP peptides, neuronal-specific enolase peptides (NSE), NeuN peptides, Thy 1.1 peptides, Prion and Huntington peptides. There are also peptides found pre-synaptically and post-synaptically. Moreover, different types of neurons exhibit distinct neurotransmitter-specific enzyme pathway proteins from which peptides are identified. For example, acetylcholine esterase is found only in cholinergic neurons while tyrosine hydroxylase (TH) is exclusive to dopaminergic neurons. Other neurotransmitter-specific enzyme pathway peptides include dopamine beta hydroxylase peptides (DbH) in noradrenergic neurons, tryptophan hydroxylase peptides (TrH) in serotonergic neurons, peptides of glutaminase and glutamine synthetase in glutamatergic neurons, and GABA transaminase peptides and glutamic acid decarboxylase peptides in GABAergic neurons. Furthermore, peptides from proteins such as GFAP and protein disulfide isomerase (PDI) are only synthesized in glial cells of the CNS, a feature that could be exploited to further understand the extent of damage to the CNS. Therefore, detection of one or more proteolytic enzyme biomarkers is indicative of the cell injured, the severity of injury and the type of injury. For example, tumors shed antigens; activation of proteolytic enzymes specific for these antigens is diagnostic of a tumor and type of tumor.

In another preferred embodiment, the invention provides for the quantitative detection of damage to the CNS, PNS and/or brain injury at a subcellular level. Depending on the type and severity of injury, neurons can undergo damage in specific cellular regions. For example, proteolytic enzymes specific for certain polypeptides, such as for example, axonal peptides, fragments and derivatives thereof include, but which are not limited to: peptides of NF-200 (NF-H), NF-160 (NF-M), NF-68 (NF-L), fragments and derivatives thereof, differentiate between axonal versus dendritic damage. Non-limiting examples of substrates for proteolytic enzyme biomarkers, such as dendritic peptides, fragments and derivatives thereof, include, but are not limited to: alpha-tubulin (P02551), beta-tubulin (P0 4691), MAP-2A/B, MAP-2C, Tau, Dynamin-1 (P21575), Dynactin (Q13561), P24. Furthermore, detection of different biomarkers not only differentiates between, for example, axonal or dendritic damage, but allows for the assessment of synaptic pathology, specific injury to elements of the pre-synaptic terminal and post-synaptic density.

In another preferred embodiment, detection of certain proteolytic enzyme biomarkers is diagnostic of the specific cell type affected following injury since neurons and glia possess distinct proteins. For example, proteolytic enzymes specific for glial proteins, peptides, fragments and derivatives thereof is diagnostic of glial cell damage. Examples of glial peptides, include, but are not limited to: peptides of GFAP (P47819), protein disulfide isomerase peptides (PDI-P04785).

The ability to detect and monitor levels of these proteolytic enzyme biomarkers after CNS injury provides enhanced diagnostic capability by allowing clinicians (1) to determine the level of injury severity in patients with various CNS injuries, (2) to monitor patients for signs of secondary CNS injuries that may elicit these cellular changes and (3) to monitor the effects of therapy by examination of these peptides in CSF or blood. Unlike other organ-based diseases where rapid diagnostics for surrogate biomarkers prove invaluable to the course of action taken to treat the disease, no such rapid, definitive diagnostic tests exist for traumatic or ischemic brain injury that might provide physicians with quantifiable neurochemical markers to help determine the seriousness of the injury, the anatomical and cellular pathology of the injury, and the implementation of appropriate medical management and treatment.

In comparison to currently existing products, the invention provides several superior advantages and benefits. First, the identification of neuronal biomarkers provides more rapid and less expensive diagnosis of injury severity than existing diagnostic devices such as computed tomography (CT) and magnetic resonance imaging (MRI). The invention also allows quantitative detection and high content assessment of damage to the CNS at a subcellular level (i.e. axonal versus dendritic). The invention also allows identification of the specific cell type affected (for example, neurons versus glia). In addition, levels of these brain-specific and brain-enriched peptides provides more accurate information regarding the level of injury severity than what is on the market.

In another preferred embodiment, nerve cell damage in a subject is analyzed by (a) providing a biological sample isolated from a subject suspected of having a damaged nerve cell; (b) detecting in the sample the presence or amount of at least one marker selected from one or more neural proteins; and (c) correlating the presence or amount of the marker with the presence or type of nerve cell damage in the subject.

Detection and identification of proteolytic enzyme biomarkers are detectable by various methods known in the art. For example, fluorogenic assays or colorimetric assays. Assays for detection of different enzymes are commercially available. An example is the fluorogenic assay from Proteus BioSciences Inc. (San Diego, Calif.), Sigma (St. Louis, Mo.). An example for fluorescent detection of active caspase-1 Protein is AFC (7-amino-4-trifluoromethylcoumarin), a synthetic fluorogenic compound that is hydrolyzed by the enzyme and yields a product that can be measured using a fluorimeter or spectrophotometer. The plate can be read at $A_{380}$ for chromogenic or $Em_{510-540}$ (Excitation at 390-400 nm) for fluorogenic detection Any animal that expresses proteolytic enzymes is preferred. Preferably, the subject is a mammal, such as for example, a human, dog, cat, horse, cow, pig, sheep, goat, primate, rat, or mouse; vertebrates such as birds, fish and reptiles. More preferably, the subject is a human. Particularly preferred are subjects suspected of having or at risk for developing traumatic or non-traumatic nervous system injuries, such as victims of brain injury caused by traumatic insults (e.g. gunshots wounds, automobile accidents, sports accidents, shaken baby syndrome), ischemic events (e.g. stroke, cerebral hemorrhage, cardiac arrest), neurodegenerative disorders (such as Alzheimer's, Huntington's, and Parkinson's diseases; Prion-related disease; other forms of dementia), epilepsy, substance abuse (e.g., from amphetamines, Ecstasy/MDMA, or ethanol), and peripheral nervous system pathologies such as diabetic neuropathy, chemotherapy-induced neuropathy and neuropathic pain.

TABLE 1

Examples of novel tissue proteins vulnerable to proteolytic attack

| Truncated forms of biomarkers (based on Powerblot data) | Human accession number | Rat (mouse) accession number |
|---|---|---|
| a/b-SNAP | P54920, Q9H115 | P54921 |
| Adaptin | P17426 | |
| AKAP220 | Q9UKA4 | Q62924 |
| Alpha and beta-tubulins | P02551, P04691 | Q68FR8, P24636 |
| Alpha synuclein | P37840 | P37377 |
| Amphiphysin | P49418 | O08838 |
| Arp3 | P61158 | Q99J72(mouse) |
| ASAP1 (ARF GTPase-activating protein) | Q9ULH1 | Q9QWY8(mouse) |
| ATP Synthase a | P15999 | |
| Bad | Q92934 | O35147 |
| Bax (tBax) | Q07812, Q07814 | Q63690 |
| Bcl2 (tBcl2) | P10415 | P49950 |
| BetaIII-spectrin | O15020 | NP_062040 |
| BetaII-Spectrin | Q01082 | |
| BRaf | P15056 | |
| BRMP2 | O08539 | |
| cAIP's | AAN23755 | |
| CalgranulinB | B31848 | |
| Calmodulin dependent kinase | CAI13791, Q5SQZ3, Q13554 | P11275 |
| Calpastatin | NP_001741 | NP_445747 |
| CaMPKII | CAI13791, Q13554 | P11275, NP_037052 |
| CaMPKIV | NP_001735 | NP_036859 |
| Catenin/pp120 | P30999 | |
| βCatenin | P35222 | Q9WU82 |
| Cathepsin L | CAI16307 | |
| cCbl | Q16773 | Q08415 |
| Clathrin Heavy Chain | P11442 | |
| Cofilin | P23528 | P45592 |
| collagen, type IV, alpha 6 | AAP35892 | |
| CtBP1 | Q13363 | Q9Z2F5 |
| DRBP76 | Q12906 | |
| Dynactin | Q14203, Q13561, O00399 | P28023, Q6AYH5 |
| Dynamin | Q05193, P50570, Q9UQ16 | P21575, P39052, Q08877 |
| Endopeptidase | P42676 | |
| Fibronectin, | O088871 | |
| GABABR2 | O75899 | O88871 |
| Glutamate (AMPA/Kainate) receptors | NP_000818 | NP_113796 |
| GlycogenphosphorylaseBB | P11216 | P53534 |
| GSPT2 | Q8IYD1 | NP_032205mouse |
| hPrp17 | O60508 | Q8BJF8mouse |
| Huntingtin | P42858 | |
| Integrin beta3 | P05106 | |
| Ki67 | P46013 | |
| Lamin A, B, C | P02545; | |
| Laminin | | |
| MCalherin | | |
| MEF2D | Q14814 | Q66HL8 |
| Metabotropic glutamate recpetors | NP_000829, NP_000832 | NP_058707, NP_073157 |
| mGluR1 | Q13255 | P23385 |
| Munc18 | Q02410, Q99767, O96018 | |
| Myelin basic protein (tMBP) | MBHUB | P02686 |

TABLE 1-continued

Examples of novel tissue proteins vulnerable to proteolytic attack

| Truncated forms of biomarkers (based on Powerblot data) | Human accession number | Rat (mouse) accession number |
|---|---|---|
| Myelin Oligodendrocyte specific protein(MOSP) | AAC25187 | |
| Myosin light chain | O14950 | P02600 |
| MYPT1 | O14974 | Q10728 |
| NCK | P16333, O43639 | |
| Nek2 | P51955 | Q91XQ1 |
| Neuronal protein 22(NP22); transgelin-3 | NP_037391 | AAL66341 |
| Neuronal protein 25(NP25) | AAP97165 | NP_113864 |
| NMDAR1 (NR1) | NP_067544 | NP_058706 AAB29181; P35439\| |
| NMDAR2 (NR2A, 2B, 2C, 2D) | Q5IS45; NP_000825; NP_000826; NP_000827 | Q00959; Q00960; |
| NMDAR3, NMDAR 4 (NR3, NR4) | AAB60368 Q91ZU9 | Q9R1M7\| |
| Neuronal nitric oxide synthase (nNOS) | G01946 | NP_032738 |
| N-ethylmaleimide sensitive fusion protein (NSF) | P46459 | NP_542152 |
| Nucleoporin NSP1 | Q9Y2X4 | AAB33384 |
| P150Glued | P28023 | AAB24566 |
| Rho-GTPase-activating protein 5 (p190-B) | Q13017 | P84107 |
| P55Cdc | Q12834 | Q62623 |
| PMCA2 | Q01814 | P11506 |
| Profilin | P07737, P35080, P60673, Q8NHR9 | P62963, Q9EPC6 |
| PSD93 | — | AAC52643 |
| Rabphilin3A | Q9Y2J0 | P47709 |
| Macrophage-stimulating protein receptor precursor (RONa) | Q04912 | — |
| Wiskott-Aldrich syndrome protein family member 1 (SCAR1) | Q92558 | — |
| Transcription elongation factor S-II protein 1 (SII/TFIIS) | P23193 | Q63799 |
| Smac/Diablo | Q9NR28 | Q9JIQ3mouse |
| SNAP25 | P60880 | P60881 |
| Striatin | O43815 | P70483 |
| Synapsin I | P17600 | P09951 |
| Synapsin II | Q92777 | Q63537 |
| Synapsin III | O14994 | NP_038750 |
| Synaptojanin-I, II | Q62910, O15056; O43426 | Q62910, O55207 |
| Synaptotagmin-I | P21579 | P21707 |
| TNIK | Q9UKE5 | P83510mouse |
| αPKC- | P17252 | P05696 |
| βPkC- | P05771 | P68403 |
| ϵPKC- | P24723 | Q64617 |
| γPKC- | P05129 | P63319 |

As described above, the invention provides the step of correlating the presence or amount of one or more proteolytic enzyme biomarker(s) with the severity and/or type of nerve cell injury. In a preferred embodiment, detection of a proteolytic enzyme biomarker can be correlated with the presence of substrate protein for which the biomarker exhibits a specific activity preferably from about 1 μg to about 500 μg per 1 mg of substrate protein per being proteolyzed in injured or stressed organs (in vivo) within minutes to days after or in vitro using purified protease-substrate protein/protein mixture ratio of 1/10,000 to 1/20 at a time point within minutes to hours. For example, the amount of neural peptides directly relates to severity of nerve tissue injury as more severe injury damages a greater number of nerve cells which in turn causes a larger amount of neural peptide(s) to accumulate in the biological sample (e.g., CSF). Whether a nerve cell injury triggers an apoptotic, oncotic (necrotic) or type 2 (autophagic) cell death, can be determined by examining the unique proteolytic enzyme biomarkers which have a high specific activity for peptides released into the biofluid in response to different cell death phenotype. The peptides can also be detected from the many cell types that comprise the nervous system. For example, astroglia, oligodendrocytes, microglia cells, Schwann cells, fibroblast, neuroblast, neural stem cells and mature neurons. Furthermore, mature neurons are differentiated into dedicated subtype fusing a primary neural transmitter such as cholinergic (nicotinic and mucarinic), glutamatergic, gabaergic, serotonergic, dopaminergic. Each of these neural subtypes expresses unique neural proteins such as those dedicated for the synthesis, metabolism and transporter and receptor of each unique neurotransmitter system (Table 1). Lastly, within a single nerve cell, there are subcellularly defined structures matched with unique neural proteins (dendritic, axonal, myelin sheath, presynaptic terminal and postsynaptic density). By monitoring the release of peptides unique to each of these regions, subcellular damage can be monitored and defined and correlated with the detection of proteolytic enzyme biomarkers after brain injury.

The biomarkers of the invention can be detected in a sample by any means. For example, immunoassays include but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, and fluorescent immunoassays. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

In another preferred embodiment, cardiac injury is determined by an increase in cardiac Troponins such as for example, troponin I. During cardiac cell damage and death, cellular contents are released into the blood stream such as cardiac troponin I.

U.S. Pat. No. 5,795,725 entitled "Methods for the Assay of Troponin I and T and Selection of Autoantibodies for use in Immunoassays" discloses assays and antibodies for detection and quantitation of cardiac specific Troponin I and Troponin T in body fluids as an indicator of myocardial infarction.

Identification of New Markers

In a preferred embodiment, a biological sample is obtained from a patient with neural injury. Biological samples comprising biomarkers from other patients and control subjects (i.e. normal healthy individuals of similar age, sex, physical condition) are used as comparisons. Biological samples are extracted as discussed above. Preferably, the sample is prepared prior to detection of biomarkers. Typically, preparation involves fractionation of the sample and collection of fractions determined to contain the biomarkers. Methods of pre-fractionation include, for example, size exclusion chromatography, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis.

In one embodiment, a sample can be pre-fractionated according to size of proteins in a sample using size exclusion chromatography. For a biological sample wherein the amount of sample available is small, preferably a size selection spin column is used. In general, the first fraction that is eluted from the column ("fraction 1") has the highest percentage of high molecular weight proteins; fraction 2 has a lower percentage of high molecular weight proteins; fraction 3 has even a lower percentage of high molecular weight proteins; fraction 4 has the lowest amount of large proteins; and so on. Each fraction can then be analyzed by immunoassays, gas phase ion spectrometry, fragments and derivatives thereof, for the detection of markers.

In another embodiment, a sample can be pre-fractionated by anion exchange chromatography. Anion exchange chromatography allows pre-fractionation of the proteins in a sample roughly according to their charge characteristics. For example, a Q anion-exchange resin can be used (e.g., Q HyperD F, BIOSEPRA, and a sample can be sequentially eluted with eluants having different pH's. Anion exchange chromatography allows separation of biomarkers in a sample that are more negatively charged from other types of biomarkers. Proteins that are eluted with an eluant having a high pH is are likely to be weakly negatively charged, and a fraction that is eluted with an eluant having a low pH is likely to be strongly negatively charged. Thus, in addition to reducing complexity of a sample, anion exchange chromatography separates proteins according to their binding characteristics.

In yet another embodiment, a sample can be pre-fractionated by heparin chromatography. Heparin chromatography allows pre-fractionation of the markers in a sample also on the basis of affinity interaction with heparin and charge characteristics. Heparin, a sulfated mucopolysaccharide, will bind markers with positively charged moieties and a sample can be sequentially eluted with eluants having different pH's or salt concentrations. Markers eluted with an eluant having a low pH are more likely to be weakly positively charged. Markers eluted with an eluant having a high pH are more likely to be strongly positively charged. Thus, heparin chromatography also reduces the complexity of a sample and separates markers according to their binding characteristics.

In yet another embodiment, a sample can be pre-fractionated by isolating proteins that have a specific characteristic, e.g. are glycosylated. For example, a CSF sample can be fractionated by passing the sample over a lectin chromatography column (which has a high affinity for sugars). Glycosylated proteins will bind to the lectin column and non-glycosylated proteins will pass through the flow through. Glycosylated proteins are then eluted from the lectin column with an eluant containing a sugar, e.g., N-acetyl-glucosamine and are available for further analysis.

Thus there are many ways to reduce the complexity of a sample based on the binding properties of the proteins in the sample, or the characteristics of the proteins in the sample.

In yet another embodiment, a sample can be fractionated using a sequential extraction protocol. In sequential extraction, a sample is exposed to a series of adsorbents to extract different types of biomarkers from a sample. For example, a sample is applied to a first adsorbent to extract certain proteins, and an eluant containing non-adsorbent proteins (i.e., proteins that did not bind to the first adsorbent) is collected. Then, the fraction is exposed to a second adsorbent. This further extracts various proteins from the fraction. This second fraction is then exposed to a third adsorbent, and so on.

Any suitable materials and methods can be used to perform sequential extraction of a sample. For example, a series of spin columns comprising different adsorbents can be used. In another example, a multi-well comprising different adsorbents at its bottom can be used. In another example, sequential extraction can be performed on a probe adapted for use in a gas phase ion spectrometer, wherein the probe surface comprises adsorbents for binding biomarkers. In this embodiment, the sample is applied to a first adsorbent on the probe, which is subsequently washed with an eluant. Markers that do not bind to the first adsorbent are removed with an eluant. The markers that are in the fraction can be applied to a second adsorbent on the probe, and so forth. The advantage of performing sequential extraction on a gas phase ion spectrometer probe is that markers that bind to various adsorbents at every stage of the sequential extraction protocol can be analyzed directly using a gas phase ion spectrometer.

In yet another embodiment, biomarkers in a sample can be separated by high-resolution electrophoresis, e.g., one or two-dimensional gel electrophoresis. A fraction containing a marker can be isolated and further analyzed by gas phase ion spectrometry. Preferably, two-dimensional gel electrophoresis is used to generate two-dimensional array of spots of biomarkers, including one or more markers. See, e.g., Jungblut and Thiede, *Mass Spectr. Rev.* 16:145-162 (1997).

The two-dimensional gel electrophoresis can be performed using methods known in the art. See, e.g., Deutscher ed., *Methods In Enzymology* vol. 182. Typically, biomarkers in a sample are separated by, e.g., isoelectric focusing, during which biomarkers in a sample are separated in a pH gradient until they reach a spot where their net charge is zero (i.e., isoelectric point). This first separation step results in one-dimensional array of biomarkers. The biomarkers in one dimensional array is further separated using a technique generally distinct from that used in the first separation step. For example, in the second dimension, biomarkers separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass of biomarkers. Typically, two-dimensional gel electrophoresis can separate chemically different biomarkers in the molecular mass range from 1000-200,000 Da within complex mixtures.

Biomarkers in the two-dimensional array can be detected using any suitable methods known in the art. For example, biomarkers in a gel can be labeled or stained (e.g., Coomassie Blue or silver staining). If gel electrophoresis generates spots that correspond to the molecular weight of one or more markers of the invention, the spot can be further analyzed by densitometric analysis or gas phase ion spectrometry. For example, spots can be excised from the gel and analyzed by gas phase ion spectrometry. Alternatively, the gel containing biomarkers can be transferred to an inert membrane by applying an electric field. Then a spot on the membrane that approximately corresponds to the molecular weight of a marker can be analyzed by gas phase ion spectrometry. In gas phase ion spectrometry, the spots can be analyzed using any suitable techniques, such as MALDI or SELDI.

Prior to gas phase ion spectrometry analysis, it may be desirable to cleave biomarkers in the spot into smaller fragments using cleaving reagents, such as proteases (e.g., trypsin). The digestion of biomarkers into small fragments provides a mass fingerprint of the biomarkers in the spot, which can be used to determine the identity of markers if desired.

In yet another embodiment, high performance liquid chromatography (HPLC) can be used to separate a mixture of biomarkers in a sample based on their different physical properties, such as polarity, charge and size. HPLC instruments typically consist of a reservoir of mobile phase, a pump, an injector, a separation column, and a detector. Biomarkers in a sample are separated by injecting an aliquot of the sample onto the column. Different biomarkers in the mixture pass through the column at different rates due to differences in their partitioning behavior between the mobile liquid phase and the stationary phase. A fraction that corresponds to the molecular weight and/or physical properties of one or more markers can be collected. The fraction can then be analyzed by gas phase ion spectrometry to detect markers.

Optionally, a marker can be modified before analysis to improve its resolution or to determine its identity. For example, the markers may be subject to proteolytic digestion before analysis. Any protease can be used. Proteases, such as trypsin, that are likely to cleave the markers into a discrete number of fragments are particularly useful. The fragments that result from digestion function as a fingerprint for the markers, thereby enabling their detection indirectly. This is particularly useful where there are markers with similar molecular masses that might be confused for the marker in question. Also, proteolytic fragmentation is useful for high molecular weight markers because smaller markers are more easily resolved by mass spectrometry. In another example, biomarkers can be modified to improve detection resolution. For instance, neuraminidase can be used to remove terminal sialic acid residues from glycoproteins to improve binding to an anionic adsorbent and to improve detection resolution. In another example, the markers can be modified by the attachment of a tag of particular molecular weight that specifically binds to molecular markers, further distinguishing them. Optionally, after detecting such modified markers, the identity of the markers can be further determined by matching the physical and chemical characteristics of the modified markers in a protein database (e.g., SwissProt, MASCOT).

After preparation, biomarkers in a sample are typically captured on a substrate for detection. Traditional substrates include antibody-coated 96-well plates or nitrocellulose membranes that are subsequently probed for the presence of proteins. Preferably, the biomarkers are identified using immunoassays as described above. However, preferred methods also include the use of biochips. Preferably the biochips are protein biochips for capture and detection of proteins. Many protein biochips are described in the art. These include, for example, protein biochips produced by Packard BioScience Company (Meriden Conn.), Zyomyx (Hayward, Calif.) and Phylos (Lexington, Mass.). In general, protein biochips comprise a substrate having a surface. A capture reagent or adsorbent is attached to the surface of the substrate. Frequently, the surface comprises a plurality of addressable locations, each of which location has the capture reagent bound there. The capture reagent can be a biological molecule, such as a polypeptide or a nucleic acid, which captures other biomarkers in a specific manner. Alternatively, the capture reagent can be a chromatographic material, such as an anion exchange material or a hydrophilic material. Examples of such protein biochips are described in the following patents or patent applications: U.S. Pat. No. 6,225,047 (Hutchens and Yip, "Use of retentate chromatography to generate difference maps," May 1, 2001), International publication WO 99/51773 (Kuimelis and Wagner, "Addressable protein arrays," Oct. 14, 1999), International publication WO 00/04389 (Wagner et al., "Arrays of protein-capture agents and methods of use thereof," Jul. 27, 2000), International publication WO 00/56934 (Englert et al., "Continuous porous matrix arrays," Sep. 28, 2000).

In general, a sample containing the biomarkers is placed on the active surface of a biochip for a sufficient time to allow binding. Then, unbound molecules are washed from the surface using a suitable eluant. In general, the more stringent the eluant, the more tightly the proteins must be bound to be retained after the wash. The retained protein biomarkers now can be detected by appropriate means.

Analytes captured on the surface of a protein biochip can be detected by any method known in the art. This includes, for example, mass spectrometry, fluorescence, surface plasmon resonance, ellipsometry and atomic force microscopy. Mass spectrometry, and particularly SELDI mass spectrometry, is a particularly useful method for detection of the biomarkers of this invention.

Preferably, a laser desorption time-of-flight mass spectrometer is used in embodiments of the invention. In laser desorption mass spectrometry, a substrate or a probe comprising markers is introduced into an inlet system. The markers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Matrix-assisted laser desorption/ionization mass spectrometry, or MALDI-MS, is a method of mass spectrometry that involves the use of an energy absorbing molecule, frequently called a matrix, for desorbing proteins intact from a probe surface. MALDI is described, for example, in U.S. Pat. No. 5,118,937 (Hillenkamp et al.) and U.S. Pat. No. 5,045,694 (Beavis and Chait). In MALDI-MS the sample is typically mixed with a matrix material and placed on the surface of an inert probe. Exemplary energy absorbing molecules include cinnamic acid derivatives, sinapinic acid ("SPA"), cyano hydroxy cinnamic acid ("CHCA") and dihydroxybenzoic acid. Other suitable energy absorbing molecules are known to those skilled in this art. The matrix dries, forming crystals that encapsulate the analyte molecules. Then the analyte molecules are detected by laser desorption/ionization mass spectrometry. MALDI-MS is useful for detecting the biomarkers of this invention if the complexity of a sample has been substantially reduced using the preparation methods described above.

Surface-enhanced laser desorption/ionization mass spectrometry, or SELDI-MS represents an improvement over MALDI for the fractionation and detection of biomolecules, such as proteins, in complex mixtures. SELDI is a method of mass spectrometry in which biomolecules, such as proteins, are captured on the surface of a protein biochip using capture reagents that are bound there. Typically, non-bound molecules are washed from the probe surface before interrogation. SELDI is described, for example, in: U.S. Pat. No. 5,719,060 ("Method and Apparatus for Desorption and Ionization of Analytes," Hutchens and Yip, Feb. 17, 1998,) U.S. Pat. No. 6,225,047 ("Use of Retentate Chromatography to Generate Difference Maps," Hutchens and Yip, May 1, 2001) and Weinberger et al., "Time-of-flight mass spectrometry," in Encyclopedia of Analytical Chemistry, R. A. Meyers, ed., pp 11915-11918 John Wiley & Sons Chichesher, 2000.

Markers on the substrate surface can be desorbed and ionized using gas phase ion spectrometry. Any suitable gas phase ion spectrometers can be used as long as it allows markers on the substrate to be resolved. Preferably, gas phase ion spectrometers allow quantitation of markers.

In one embodiment, a gas phase ion spectrometer is a mass spectrometer. In a typical mass spectrometer, a substrate or a probe comprising markers on its surface is introduced into an inlet system of the mass spectrometer. The markers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector. The detector then translates information of the detected ions into mass-to-charge ratios. Detection of the presence of markers or other substances will typically involve detection of signal intensity. This, in turn, can reflect the quantity and character of markers bound to the substrate. Any of the components of a mass spectrometer (e.g., a desorption source, a mass analyzer, a detector, etc.) can be combined with other suitable components described herein or others known in the art in embodiments of the invention.

In another embodiment, an immunoassay can be used to detect and analyze markers in a sample. This method comprises: (a) providing an antibody that specifically binds to a marker; (b) contacting a sample with the antibody; and (c) detecting the presence of a complex of the antibody bound to the marker in the sample.

To prepare an antibody that specifically binds to a marker, purified markers or their nucleic acid sequences can be used. Nucleic acid and amino acid sequences for markers can be obtained by further characterization of these markers. The molecular weights of digestion fragments from each marker can be used to search the databases, such as SwissProt database, for sequences that will match the molecular weights of digestion fragments generated by various enzymes. Using this method, the nucleic acid and amino acid sequences of other markers can be identified if these markers are known proteins in the databases.

Alternatively, the proteins can be sequenced using protein ladder sequencing. Protein ladders can be generated by, for example, fragmenting the molecules and subjecting fragments to enzymatic digestion or other methods that sequentially remove a single amino acid from the end of the fragment. Methods of preparing protein ladders are described, for example, in International Publication WO 93/24834 (Chait et al.) and U.S. Pat. No. 5,792,664 (Chait et al.). The ladder is then analyzed by mass spectrometry. The difference in the masses of the ladder fragments identify the amino acid removed from the end of the molecule.

If the markers are not known proteins in the databases, nucleic acid and amino acid sequences can be determined with knowledge of even a portion of the amino acid sequence of the marker. For example, degenerate probes can be made based on the N-terminal amino acid sequence of the marker. These probes can then be used to screen a genomic or cDNA library created from a sample from which a marker was initially detected. The positive clones can be identified, amplified, and their recombinant DNA sequences can be subcloned using techniques which are well known. See, e.g., *Current Protocols for Molecular Biology* (Ausubel et al., Green Publishing Assoc. and Wiley-Interscience 1989) and *Molecular Cloning: A Laboratory Manual,* 3rd Ed. (Sambrook et al., Cold Spring Harbor Laboratory, NY 2001).

Using the purified markers or their nucleic acid sequences, antibodies that specifically bind to a marker can be prepared using any suitable methods known in the art. See, e.g., Coligan, *Current Protocols in Immunology* (1991); Harlow & Lane, *Antibodies: A Laboratory Manual* (1988); Goding, *Monoclonal Antibodies: Principles and Practice* (2d ed. 1986); and Kohler & Milstein, *Nature* 256:495-497 (1975). Such techniques include, but are not limited to, antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

After the antibody is provided, a marker can be detected and/or quantified using any of suitable immunological binding assays known in the art (see, e.g., U.S. Pat. Nos. 4,366,241; 4,376,110; 4,517,288; and 4,837,168). Useful assays include, for example, an enzyme immune assay (EIA) such as enzyme-linked immunosorbent assay (ELISA), a radioimmune assay (RIA), a Western blot assay, or a slot blot assay. These methods are also described in, e.g., *Methods in Cell Biology Antibodies in Cell Biology*, volume 37 (Asai, ed. 1993); *Basic and Clinical Immunology* (Stites & Terr, eds., 7th ed. 1991); and Harlow & Lane, supra.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or protein chip array described above. The sample is preferably a biological fluid sample taken from a subject. Examples of biological fluid samples include cerebrospinal fluid, blood, serum, plasma, neuronal cells, tissues, urine, tears, saliva etc. In a preferred embodiment, the biological fluid comprises cerebrospinal fluid. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxide, alkaline phosphatase and others commonly used in an ELISA), and colorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker is incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations fragments and derivatives thereof. Usually the assays will be carried out at ambient temperature, although they can be conducted over a range of temperatures, such as 10° C. to 40° C.

Immunoassays can be used to determine presence or absence of a marker in a sample as well as the quantity of a marker in a sample. First, a test amount of a marker in a sample can be detected using the immunoassay methods described above. If a marker is present in the sample, it will form an antibody-marker complex with an antibody that specifically binds the marker under suitable incubation conditions described above. The amount of an antibody-marker complex can be determined by comparing to a standard. A standard can be, e.g., a known compound or another protein known to be present in a sample. As noted above, the test amount of marker need not be measured in absolute units, as long as the unit of measurement can be compared to a control.

The methods for detecting these markers in a sample have many applications. For example, one or more markers can be measured to aid in the diagnosis of spinal injury, brain injury, the degree of injury, neural injury due to neuronal disorders, alcohol and drug abuse, fetal injury due to alcohol and/or drug abuse by pregnant mothers, etc. In another example, the methods for detection of the markers can be used to monitor responses in a subject to treatment. In another example, the methods for detecting markers can be used to assay for and to identify compounds that modulate expression of these markers in vivo or in vitro.

Data generated by desorption and detection of markers can be analyzed using any suitable means. In one embodiment, data is analyzed with the use of a programmable digital computer. The computer program generally contains a readable medium that stores codes. Certain code can be devoted to memory that includes the location of each feature on a probe, the identity of the adsorbent at that feature and the elution conditions used to wash the adsorbent. The computer also contains code that receives as input, data on the strength of the signal at various molecular masses received from a particular addressable location on the probe. This data can indicate the number of markers detected, including the strength of the signal generated by each marker.

Data analysis can include the steps of determining signal strength (e.g., height of peaks) of a marker detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. Then the signal strength detected for each marker or other biomolecules can be displayed in the form of relative intensities in the scale desired (e.g., 100). Alternatively, a standard (e.g., a CSF protein) may be admitted with the sample so that a peak from the standard can be used as a reference to calculate relative intensities of the signals observed for each marker or other markers detected.

The computer can transform the resulting data into various formats for displaying. In one format, referred to as "spectrum view or retentate map," a standard spectral view can be displayed, wherein the view depicts the quantity of marker reaching the detector at each particular molecular weight. In another format, referred to as "peak map," only the peak height and mass information are retained from the spectrum view, yielding a cleaner image and enabling markers with nearly identical molecular weights to be more easily seen. In yet another format, referred to as "gel view," each mass from the peak view can be converted into a grayscale image based on the height of each peak, resulting in an appearance similar to bands on electrophoretic gels. In yet another format, referred to as "3-D overlays," several spectra can be overlaid to study subtle changes in relative peak heights. In yet another format, referred to as "difference map view," two or more spectra can be compared, conveniently highlighting unique markers and markers which are up- or down-regulated between samples. Marker profiles (spectra) from any two samples may be compared visually. In yet another format, Spotfire Scatter Plot can be used, wherein markers that are detected are plotted as a dot in a plot, wherein one axis of the plot represents the apparent molecular mass of the markers detected and another axis represents the signal intensity of markers detected. For each sample, markers that are detected and the amount of markers present in the sample can be saved in a computer readable medium. This data can then be compared to a control (e.g., a profile or quantity of markers detected in control, e.g., normal, healthy subjects in whom neural injury is undetectable).

Alternative Methods for Identification of Homologous Proteolytic Biomarkers

With respect to the cloning of allelic variants of the human proteolytic marker genes and homologues from other species (e.g., mouse), isolated proteolytic marker gene sequences may be labeled and used to screen a cDNA library constructed from mRNA obtained from appropriate cells or tissues (e.g., brain tissues) derived from the organism (e.g., mouse) of interest. The hybridization conditions used should be of a lower stringency when the cDNA library is derived from an organism different from the type of organism from which the labeled sequence was derived.

Alternatively, the labeled fragment may be used to screen a genomic library derived from the organism of interest, again, using appropriately stringent conditions. Low stringency conditions are well known to those of skill in the art, and will vary predictably depending on the specific organisms from which the library and the labeled sequences are derived. For guidance regarding such conditions see, for example, Sambrook, et al., 1989, Molecular Cloning, A Laboratory Manual, Second Edition, Cold Spring Harbor Press, N.Y.; and Ausubel, et al., 1989, Current Protocols in Molecular Biology, Green Publishing Associates and Wiley Interscience, N.Y.

Further, an proteolytic marker gene allelic variant may be isolated from, for example, human nucleic acid, by performing PCR using the pan specific probes. For example, the template for the reaction may be cDNA obtained by reverse transcription of mRNA prepared from, for example, human or non-human cell lines or tissue known or suspected to express a proteolytic marker gene or allelic variant thereof. Preferably, the allelic variant will be isolated from an individual who has a neuronal disorder.

PCR technology may also be utilized to isolate full length cDNA sequences. For example, RNA may be isolated, following standard procedures, from an appropriate cellular or tissue source (i.e., one known, or suspected, to express the proteolytic marker gene, such as, for example, brain tissue samples obtained through biopsy or post-mortem). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAse H, and second strand synthesis may then be primed with a poly-C primer. Thus, cDNA sequences upstream of the amplified fragment may easily be isolated. For a review of cloning strategies that may be used, see e.g., Sambrook et al., 1989, infra.

Another preferred method includes SAGE. Serial Analysis of Gene Expression (SAGE), is based on the identification of and characterization of partial, defined sequences of transcripts corresponding to gene segments. These defined transcript sequence "tags" are markers for genes which are expressed in a cell, a tissue, or an extract, for example.

SAGE is based on several principles. First, a short nucleotide sequence tag (9 to 10 bp) contains sufficient information content to uniquely identify a transcript provided it is isolated from a defined position within the transcript. For example, a sequence as short as 9 bp can distinguish about 262,144 transcripts given a random nucleotide distribution at the tag site, whereas estimates suggest that the human genome encodes about 80,000 to 200,000 transcripts (Fields, et al., *Nature Genetics,* 7:345 1994). The size of the tag can be shorter for lower eukaryotes or prokaryotes, for example, where the number of transcripts encoded by the genome is lower. For example, a tag as short as 6-7 bp may be sufficient for distinguishing transcripts in yeast.

Second, random dimerization of tags allows a procedure for reducing bias (caused by amplification and/or cloning). Third, concatenation of these short sequence tags allows the efficient analysis of transcripts in a serial manner by sequencing multiple tags within a single vector or clone. As with serial communication by computers, wherein information is transmitted as a continuous string of data, serial analysis of the sequence tags requires a means to establish the register and boundaries of each tag. The concept of deriving a defined tag from a sequence in accordance with the present invention is useful in matching tags of samples to a sequence database. In the preferred embodiment, a computer method is used to match a sample sequence with known sequences.

The tags used herein, uniquely identify genes. This is due to their length, and their specific location (3') in a gene from which they are drawn. The full length genes can be identified by matching the tag to a gene data base member, or by using the tag sequences as probes to physically isolate previously unidentified genes from cDNA libraries. The methods by which genes are isolated from libraries using DNA probes are well known in the art. See, for example, Veculescu et al., *Science* 270: 484 (1995), and Sambrook et al. (1989), MOLECULAR CLONING: A LABORATORY MANUAL, 2nd ed. (Cold Spring Harbor Press, Cold Spring Harbor, N.Y.). Once a gene or transcript has been identified, either by matching to a data base entry, or by physically hybridizing to a cDNA molecule, the position of the hybridizing or matching region in the transcript can be determined. If the tag sequence is not in the 3' end, immediately adjacent to the restriction enzyme used to generate the SAGE tags, then a spurious match may have been made. Confirmation of the identity of a SAGE tag can be made by comparing transcription levels of the tag to that of the identified gene in certain cell types. Analysis of gene expression is not limited to the above method but can include any method known in the art. All of these principles may be applied independently, in combination, or in combination with other known methods of sequence identification.

Examples of methods of gene expression analysis known in the art include DNA arrays or microarrays (Brazma and Vilo, *FEBS Lett.,* 2000, 480, 17-24; Celis, et al., *FEBS Lett.,* 2000, 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.,* 1999, 303, 258-72), TOGA (total gene expression analysis) (Sutcliffe, et al., *Proc. Natl. Acad. Sci. U.S.A.,* 2000, 97, 1976-81), protein arrays and proteomics (Celis, et al., *FEBS Lett.,* 2000, 480, 2-16; Jungblut, et al., *Electrophoresis,* 1999, 20, 2100-10), expressed sequence tag (EST) sequencing (Celis, et al., *FEBS Lett.,* 2000, 480, 2-16; Larsson, et al., *J. Biotechnol.,* 2000, 80, 143-57), subtractive RNA fingerprinting (SuRF) (Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J. Cancer,* 1999, 35, 1895-904) and mass spectrometry methods (reviewed in (To, Comb. Chem. High Throughput Screen, 2000, 3, 235-41).

In a preferred embodiment, Expressed Sequence Tags (ESTs), can also be used to identify nucleic acid molecules which are over expressed in a neuronal cell. ESTs from a variety of databases can be identified. For example, preferred databases include, for example, Online Mendelian Inheritance in Man (OMIM), the Cancer Genome Anatomy Project (CGAP), GenBank, EMBL, PIR, SWISS-PROT, and the like. OMIM, which is a database of genetic mutations associated with disease, was developed, in part, for the National Center for Biotechnology Information (NCBI). OMIM can be accessed through the world wide web of the Internet. AP is an interdisciplinary program to establish the information and technological tools required to decipher the molecular anatomy of a cancer cell. CGAP can be accessed through the world wide web of the Internet. Some of these databases may contain complete or partial nucleotide sequences. In addition, alternative transcript forms can also be selected from private genetic databases. Alternatively, nucleic acid molecules can be selected from available publications or can be determined especially for use in connection with the present invention.

Alternative transcript forms can be generated from individual ESTs which are within each of the databases by computer software which generates contiguous sequences. In another embodiment of the present invention, the nucleotide sequence of the nucleic acid molecule is determined by assembling a plurality of overlapping ESTs. The EST database (dbEST), which is known and available to those skilled in the art, comprises approximately one million different human mRNA sequences comprising from about 500 to 1000 nucleotides, and various numbers of ESTs from a number of different organisms. dbEST can be accessed through the world wide web of the Internet. These sequences are derived from a cloning strategy that uses cDNA expression clones for genome sequencing. ESTs have applications in the discovery of new genes, mapping of genomes, and identification of coding regions in genomic sequences. Another important feature of EST sequence information that is becoming rapidly available is tissue-specific gene expression data. This can be extremely useful in targeting selective gene(s) for therapeutic intervention. Since EST sequences are relatively short, they must be assembled in order to provide a complete sequence. Because every available clone is sequenced, it results in a number of overlapping regions being reported in the database. The end result is the elicitation of alternative transcript forms from, for example, immune cells and neuronal cells.

Assembly of overlapping ESTs extended along both the 5' and 3' directions results in a full-length "virtual transcript." The resultant virtual transcript may represent an already characterized nucleic acid or may be a novel nucleic acid with no known biological function. The Institute for Genomic Research (TIGR) Human Genome Index (HGI) database, which is known and available to those skilled in the art, contains a list of human transcripts. TIGR can be accessed through the world wide web of the Internet. Transcripts can be generated in this manner using TIGR-Assembler, an engine to build virtual transcripts and which is known and available to those skilled in the art. TIGR-Assembler is a tool for assembling large sets of overlapping sequence data such as ESTs, BACs, or small genomes, and can be used to assemble eukaryotic or prokaryotic sequences. TIGR-Assembler is described in, for example, Sutton, et al., *Genome Science & Tech.,* 1995, 1, 9-19, which is incorporated herein by reference in its entirety, and can be accessed through the file transfer program of the Internet, at, for example, tigr.org/pub/software/TIGR. assembler. In addition, GLAXO-MRC, which is known and available to those skilled in the art, is another protocol for constructing virtual transcripts. PHRAP is used for sequence assembly within Find Neighbors and Assemble EST Blast. PHRAP can be accessed through the world wide web of the Internet. Identification of ESTs and generation of contiguous ESTs to form full length RNA molecules is described in detail in U.S. application Ser. No. 09/076,440, which is incorporated herein by reference in its entirety.

As mentioned above, the proteolytic marker gene sequences may be used to isolate mutant proteolytic marker gene alleles, preferably from a human subject. Such mutant alleles may be isolated from individuals either known or proposed to have a genotype that contributes to the symptoms of a neuronal disorder such as Alzheimer's or Parkinson's disease.

A cDNA of a mutant allelic variant of the proteolytic marker gene may be isolated, for example, by using PCR, a technique that is well known to those of skill in the art. In this case, the first cDNA strand may be synthesized by hybridizing an oligo-dT oligonucleotide to mRNA isolated from tissue known or suspected to be expressed in an individual putatively carrying the mutant proteolytic marker allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant proteolytic marker allele to that of the normal proteolytic marker allele, the mutation(s) responsible for the loss or alteration of function of the mutant proteolytic marker gene product can be ascertained.

Genomic DNA isolated from lymphocytes or other immune cells of normal and affected individuals can also be used as PCR template. PCR products from normal and affected individuals are compared, either by single strand conformational polymorphism (SSCP) mutation detection techniques and/or by sequencing.

In another embodiment of the invention, the above nucleic acid sequences encoding proteolytic markers may be used to generate hybridization probes useful in mapping the naturally-occurring genomic sequence, as well as to detect in an individual, or group of individuals, allelic variants of genes that are present in individuals suffering from or susceptible to neural defects or diseases. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries (see, e.g., Harrington et al., 1997, *Nat. Genet.* 15: 345-355; Price, 1993, *Blood Rev.* 7: 127-134; and Trask, 1991, *Trends Genet.* 7: 149-154).

Fluorescent in situ hybridization (FISH) may be correlated with other physical chromosome mapping techniques and genetic map data (see, e.g., Heinz-Ulrich et al., 1995, in Meyers, supra, pp. 965-968). Examples of genetic map data can be found in various scientific journals or at the Online Mendelian Inheritance in Man (OMIM) site. The nucleotide sequences of the invention may be used to detect differences in gene sequences among resistant, susceptible, or allelic variants in individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for genes of the invention using positional cloning or other gene discovery techniques. Once the genes have been crudely localized by genetic linkage to a particular genomic region, e.g., ataxia-telangiectasia to 11q22-23, any sequences mapping to that area may represent associated or regulatory genes for further investigation (see, e.g., Gatti et al., 1988, *Nature* 336:577-580). Other examples of particular genomic regions include, but not limited to, leukocyte receptor cluster to 19q13.3-13.4 The nucleotide sequence of the subject invention may also be used to detect differences in the chromosomal location due to translocation, inversion, etc., among normal, or affected individuals.

The genes identified from individuals are amplified by PCR and sequenced by methods well known in the art. These nucleic acid sequences are then used in the assays described in the examples and materials and methods to correlate the sequence of the genes identified, with, for example, the percentage of individuals suffering from Alzheimer's disease as compared to normal individuals. Identification of more gene sequences and their amino acid sequences allows for a correlation between the expression of proteolytic markers in cells of the nervous system, including the brain, and individuals predisposed to a neural disease or defect.

In yet another aspect, variants of the nucleic acid molecules as identified in immune cells from individuals of different haplotypes and/or suffering from or susceptible to neural defects can be used to detect allelic variations of immune related molecules in neural cells. An "allele" or "variant" is an alternative form of a gene. Of particular utility in the invention are variants of the genes encoding any potential immune related molecule in the nervous system identified by the methods of this invention. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

To further identify variant nucleic acid molecules which can detect, for example, early stage Alzheimer's, nucleic acid molecules can be grouped into sets depending on the homology, for example. The members of a set of nucleic acid molecules are compared. Preferably, the set of nucleic acid molecules is a set of alternative transcript forms of nucleic acid. Preferably, the members of the set of alternative transcript forms of nucleic acids include at least one member which is associated, or whose encoded protein is associated, with a disease state or biological condition. For example, a set of proteolytic marker molecules from brain cells and neural cells from normal and a diseased individual are compared. At least one of the members of the set of nucleic acid molecule alternative transcript forms can be associated with for example, Alzheimer's or any other neural defect, as described above. Thus, comparison of the members of the set of nucleic acid molecules results in the identification of at least one alternative transcript form of nucleic acid molecule which is associated, or whose encoded protein is associated, with a disease state or biological condition. In a preferred embodiment of the invention, the members of the set of nucleic acid molecules are from a common gene. In another embodiment of the invention, the members of the set of nucleic acid molecules are from a plurality of genes. In another embodiment of the invention, the members of the set of nucleic acid molecules are from different taxonomic species. Nucleotide sequences of a plurality of nucleic acids from different taxonomic species can be identified by performing a sequence similarity search, an ortholog search, or both, such searches being known to persons of ordinary skill in the art.

Sequence similarity searches can be performed manually or by using several available computer programs known to those skilled in the art. Preferably, Blast and Smith-Waterman algorithms, which are available and known to those skilled in the art, and the like can be used. Blast is NCBI's sequence similarity search tool designed to support analysis of nucleotide and protein sequence databases. Blast can be accessed through the world wide web of the Internet. The GCG Package provides a local version of Blast that can be used either with public domain databases or with any locally available searchable database. GCG Package v9.0 is a commercially available software package that contains over 100 interrelated software programs that enables analysis of sequences by editing, mapping, comparing and aligning them. Other programs included in the GCG Package include, for example, programs which facilitate RNA secondary structure predictions, nucleic acid fragment assembly, and evolutionary analysis. In addition, the most prominent genetic databases (GenBank, EMBL, PIR, and SWISS-PROT) are distributed along with the GCG Package and are fully accessible with the database searching and manipulation programs. GCG can be accessed through the Internet. Fetch is a tool available in GCG that can get annotated GenBank records based on accession numbers and is similar to Entrez. Another sequence similarity search can be performed with GeneWorld and GeneThesaurus from Pangea. GeneWorld 2.5 is an automated, flexible, high-throughput application for analysis of polynucleotide and protein sequences. GeneWorld allows for automatic analysis and annotations of sequences. Like GCG, GeneWorld incorporates several tools for homology searching, gene finding, multiple sequence alignment, secondary structure prediction, and motif identification. GENE THESAURUS1.0™ is a sequence and annotation data subscription service providing information from multiple sources, providing a relational data model for public and local data.

Another alternative sequence similarity search can be performed, for example, by BlastParse. BlastParse is a PERL script running on a UNIX platform that automates the strategy described above. BlastParse takes a list of target accession numbers of interest and parses all the GenBank fields into "tab-delimited" text that can then be saved in a "relational database" format for easier search and analysis, which provides flexibility. The end result is a series of completely parsed GenBank records that can be easily sorted, filtered, and queried against, as well as an annotations-relational database.

Preferably, the plurality of nucleic acids from different taxonomic species which have homology to the target nucleic acid, as described above in the sequence similarity search, are further delineated so as to find orthologs of the target nucleic acid therein. An ortholog is a term defined in gene classification to refer to two genes in widely divergent organisms that have sequence similarity, and perform similar functions within the context of the organism. In contrast, paralogs are genes within a species that occur due to gene duplication, but have evolved new functions, and are also referred to as isotypes. Optionally, paralog searches can also be performed. By performing an ortholog search, an exhaustive list of homologous sequences from as diverse organisms as possible is obtained. Subsequently, these sequences are analyzed to select the best representative sequence that fits the criteria for being an ortholog. An ortholog search can be performed by programs available to those skilled in the art including, for example, Compare. Preferably, an ortholog search is performed with access to complete and parsed GenBank annotations for each of the sequences. Currently, the records obtained from GenBank are "flat-files", and are not ideally suited for automated analysis. Preferably, the ortholog search is performed using a Q-Compare program. Preferred steps of the Q-Compare protocol are described in the flowchart set forth in U.S. Pat. No. 6,221,587, incorporated herein by reference.

Preferably, interspecies sequence comparison is performed using Compare, which is available and known to those skilled in the art. Compare is a GCG tool that allows pair-wise comparisons of sequences using a window/stringency criterion. Compare produces an output file comprising points where matches of specified quality are found. These can be plotted with another GCG tool, DotPlot.

The polynucleotides of this invention can be isolated using the technique described in the experimental section or replicated using PCR. The PCR technology is the subject matter of U.S. Pat. Nos. 4,683,195, 4,800,159, 4,754,065, and 4,683,202 and described in PCR: The Polymerase Chain Reaction (Mullis et al. eds, Birkhauser Press, Boston (1994)) or MacPherson et al. (1991) and (1994), supra, and references cited therein. Alternatively, one of skill in the art can use the sequences provided herein and a commercial DNA synthesizer to replicate the DNA. Accordingly, this invention also provides a process for obtaining the polynucleotides of this invention by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the polynucleotide into a suitable replication vector and insert the vector into a suitable host cell (procaryotic or eucaryotic) for replication and amplification. The DNA so amplified can be isolated from the cell by methods well known to those of skill in the art. A process for obtaining polynucleotides by this method is further provided herein as well as the polynucleotides so obtained.

In an embodiment of the invention the presence of the one or more proteolytic marker nucleic acid molecules, isolated from a cell, is correlated to neuronal cell sample of a normal subject and one suffering from or susceptible to a neural disorder. The sample is preferably obtained from a mammal suspected of having a nerve or brain cell disorder. Preferably, a nucleic acid molecule that is indicative of a proteolytic marker molecule and detected in a neural cell comprises a sequence having at least about 50% sequence identity to any one of SEQ ID NO's: 1-149, more preferably a nucleic acid molecule that is indicative of a proteolytic marker molecule and detected in a neural cell comprises a sequence having at least about 70% sequence identity to any one of SEQ ID NO's: 1-149, more preferably a nucleic acid molecule that is indicative of a proteolytic marker molecule and detected in a neural cell comprises a sequence having at least about 80% sequence identity to any one of SEQ ID NO's: 1-149, more preferably a nucleic acid molecule that is indicative of a proteolytic marker molecule and detected in a neural cell comprises a sequence having at least about 90%, 95%, 96%, 97%, 95%, 99% or 99.9% sequence identity to any one of SEQ ID NO's: 1-149.

Percent identity and similarity between two sequences (nucleic acid or polypeptide) can be determined using a mathematical algorithm (see, e.g., *Computational Molecular Biology*, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

To determine the percent identity of two amino acid sequences or of two nucleic acid sequences, the sequences are aligned for optimal comparison purposes (e.g., gaps are introduced in one or both of a first and a second amino acid or nucleic acid sequence for optimal alignment and non-homologous sequences can be disregarded for comparison purposes). The percent identity between the two sequences is a function of the number of identical positions shared by the sequences, taking into account the number of gaps, and the length of each gap which need to be introduced for optimal alignment of the two sequences. The amino acid residues or nucleotides at corresponding amino acid positions or nucleotide positions, respectively, are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

A "comparison window" refers to a segment of any one of the number of contiguous positions selected from the group consisting of from about 25 to about 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art.

For example, the percent identity between two amino acid sequences can be determined using the Needleman and Wunsch algorithm (*J. Mol. Biol.* (48): 444-453, 1970) which is part of the GAP program in the GCG software package (available at http://www.gcg.com), by the local homology algorithm of Smith & Waterman (*Adv. Appl. Math.* 2: 482, 1981), by the search for similarity methods of Pearson & Lipman (*Proc. Natl. Acad. Sci. USA* 85: 2444, 1988) and Altschul, et al. (*Nucleic Acids Res.* 25(17): 3389-3402, 1997), by computerized implementations of these algorithms (GAP, BESTFIT, FASTA, and BLAST in the Wisconsin Genetics Software Package (available from, Genetics Computer Group, 575 Science Dr., Madison, Wis.), or by manual alignment and visual inspection (see, e.g., Ausubel et al., supra). Gap parameters can be modified to suit a user's needs. For example, when employing the GCG software package, a NWSgapdna.CMP matrix and a gap weight of 40, 50, 60, 70, or 80 and a length weight of 1, 2, 3, 4, 5, or 6 can be used. Exemplary gap weights using a Blossom 62 matrix or a PAM250 matrix, are 16, 14, 12, 10, 8, 6, or 4, while exemplary length weights are 1, 2, 3, 4, 5, or 6. The GCG software package can be used to determine percent identity between nucleic acid sequences. The percent identity between two amino acid or nucleotide sequences also can be determined using the algorithm of E. Myers and W. Miller (CABIOS 4: 11-17, 1989) which has been incorporated into the ALIGN program (version 2.0), using a PAM120 weight residue table, a gap length penalty of 12 and a gap penalty of 4.

The nucleic acid and protein sequences of the present invention can further be used as query sequences to perform a search against sequence databases to, for example, identify other family members or related sequences. Such searches can be performed using the NBLAST and XBLAST programs (version 2.0) of Altschul, et al. (*J. Mol. Biol.* 215: 403-10, 1990). BLAST nucleotide searches can be performed with the NBLAST program, with exemplary scores=100, and wordlengths=12 to obtain nucleotide sequences homologous to or with sufficient percent identity to the nucleic acid molecules of the invention. BLAST protein searches can be performed with the XBLAST program, with exemplary scores=50 and word lengths=3 to obtain amino acid sequences sufficiently homologous to or with sufficient % identity to the proteins of the invention. To obtain gapped alignments for comparison purposes, gapped BLAST can be used as described in Altschul et al. (*Nucleic Acids Res.* 25(17): 3389-3402, 1997). When using BLAST and gapped BLAST programs, the default parameters of the respective programs (e.g., XBLAST and NBLAST) can be used.

The invention also comprises polypeptides, in neural cells, corresponding to a nucleic acid molecule product which comprises conservative substitutions that are phenotypically silent. Such substitutions are those that substitute a given amino acid in a polypeptide by another amino acid of like characteristics. Guidance concerning amino acid changes which are likely to be phenotypically silent may be found in Bowie et al., *Science* 247: 1306-1310, 1990, for example. Conservative substitution tables providing functionally similar amino acids are well known in the art (see, e.g., Henikoff and Henikoff, *Proc. Natl. Acad. Sci.* USA 89: 10915-10919, 1992) and in the table below.

| Conservative Amino Acid Substitutions | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

As used herein, the term "fragment or segment", as applied to a nucleic acid sequence, gene or polypeptide, will ordinarily be at least about 5 contiguous nucleic acid bases (for nucleic acid sequence or gene) or amino acids (for polypeptides), typically at least about 10 contiguous nucleic acid bases or amino acids, more typically at least about 20 contiguous nucleic acid bases or amino acids, usually at least about 30 contiguous nucleic acid bases or amino acids, preferably at least about 40 contiguous nucleic acid bases or amino acids, more preferably at least about 50 contiguous nucleic acid bases or amino acids, and even more preferably at least about 60 to 80 or more contiguous nucleic acid bases or amino acids in length. "Overlapping fragments" as used herein, refer to contiguous nucleic acid or peptide fragments which begin at the amino terminal end of a nucleic acid or protein and end at the carboxy terminal end of the nucleic acid or protein. Each nucleic acid or peptide fragment has at least about one contiguous nucleic acid or amino acid position in common with the next nucleic acid or peptide fragment, more preferably at least about three contiguous nucleic acid bases or amino acid positions in common, most preferably at least about ten contiguous nucleic acid bases or amino acid positions in common.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides. Additional preferred embodiments will include lengths in excess of those numbers, e.g., 63, 72, 87, 96, 105, 117, etc. Said fragments may have termini at any pairs of locations, but especially at boundaries between structural domains, e.g., membrane spanning portions.

Homologous nucleic acid sequences, when compared, exhibit significant sequence identity or similarity. The standards for homology in nucleic acids are either measures for homology generally used in the art by sequence comparison or based upon hybridization conditions. The hybridization conditions are described in greater detail below.

As used herein, "substantial homology" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a fragment derived from, for example, neural or brain cells. Typically, selective hybridization will occur when there is at least about 55% homology over a stretch of at least about 14 nucleotides, preferably at least about 65%, more preferably at least about 75%, and most preferably at least about 90%. See, Kanehisa (1984) *Nucl. Acids Res.* 12:203-213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides. The endpoints of the segments may be at many different pair combinations. Chromosomal synteny may be used to further distinguish between homologous genes when there is sufficient evolutionary conservation between the genomes that are being compared, e.g. between mammalian species. A "syntenic homolog" has both sequence identity to the reference gene, and has the corresponding chromosomal location in relation to closely linked genes. Syntenic homologs have a high probability of sharing spatial and temporal localization of gene expression, and of encoding proteins that fill equivalent biological roles.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349-370.

Diagnosis of Neural Injury

In another aspect, the invention provides methods for aiding a human neural injury and/or neural disorder diagnosis using one or more markers. For example, proteolytic enzyme biomarkers with a specific activity of about 1 μg to about 500 μg per 1 mg of substrate protein per being proteolyzed in injured or stressed organs (in vivo) within minutes to days after or in vitro using purified protease-substrate protein/protein mixture ratio of 1/10,000 to 1/20 at a time point within minutes to hours, for proteins identified in Table 1, peptides, fragments or derivatives thereof and/or those identified by SEQ ID NO's.: 1-149. These markers can be used singularly or in combination with other proteolytic enzyme markers or a combination of proteolytic enzyme biomarkers and neural peptides. The markers are differentially present in samples of a human patient, for example a TBI patient, and a normal subject in whom neural injury is undetectable. For example, some of the markers are expressed at an elevated level and/or are present at a higher frequency in human patients with neural injury and/or neuronal disorders than in normal subjects. Therefore, detection of one or more of these markers in a person would provide useful information regarding the probability that the person may have neural injury and/or neuronal disorder.

Nervous system diseases, neuronal disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

Accordingly, embodiments of the invention include methods for aiding human neural injury and/or neuronal disorders, wherein the method comprises: (a) detecting at least one proteolytic enzyme biomarker in a sample, and (b) correlating the detection of the marker or markers with a probable diagnosis of human neural injury and/or neuronal disorder or organ injury such as the heart. The correlation may take into account the amount of the marker or markers in the sample compared to a control amount of the marker or markers (up or down regulation of the marker or markers) (e.g., in normal subjects in whom human neural injury is undetectable). The correlation may take into account the presence or absence of the markers in a test sample and the frequency of detection of the same markers in a control. The correlation may take into account both of such factors to facilitate determination of whether a subject has neural injury, the degree of severity of the neural injury, and subcellular location of the injury, or not.

Any suitable samples can be obtained from a subject to detect markers. Preferably, a sample is a cerebrospinal fluid sample from the subject. If desired, the sample can be prepared as described above to enhance detectability of the markers. For example, to increase the detectability of markers, a blood serum sample from the subject can be preferably fractionated by, e.g., Cibacron blue agarose chromatography and single stranded DNA affinity chromatography, anion exchange chromatography fragments and derivatives thereof. Sample preparations, such as pre-fractionation protocols, is optional and may not be necessary to enhance detectability of markers depending on the methods of detection used. For example, sample preparation may be unnecessary if antibodies that specifically bind markers are used to detect the presence of markers in a sample.

Any suitable method can be used to detect a marker or markers in a sample. For example, fluorogenic assays or gas phase ion spectrometry can be used as described above. Using these methods, one or more markers can be detected. Preferably, a sample is tested for the presence of a plurality of markers. Detecting the presence of a plurality of markers, rather than a single marker alone, would provide more information for the diagnostician. Specifically, the detection of a plurality of markers in a sample would increase the percentage of true positive and true negative diagnoses and would decrease the percentage of false positive or false negative diagnoses.

The detection of the marker or markers is then correlated with a probable diagnosis of neural injury and/or neuronal disorders. In some embodiments, the detection of the mere presence or absence of a marker, without quantifying the amount of marker, is useful and can be correlated with a probable diagnosis of neural injury and/or neuronal disorders.

In other embodiments, the detection of markers can involve quantifying the markers to correlate the detection of markers with a probable diagnosis of neural injury, degree of severity of neural injury, diagnosis of neural disorders fragments and derivatives thereof. Thus, if the amount of the markers detected in a subject being tested is higher compared to a control amount, then the subject being tested has a higher probability of having such injuries and/or neural disorders.

Similarly, in another embodiment, the detection of markers can further involve quantifying the markers to correlate the detection of markers with a probable diagnosis of neural injury, degree of severity of neural injury, diagnosis of neural disorders, wherein the markers are present in lower quantities in CSF or blood serum samples from patients than in blood serum samples of normal subjects. Thus, if the amount of the markers detected in a subject being tested is lower compared to a control amount, then the subject being tested has a higher probability of having neural injury, organ injury and/or neural disorder.

When the markers are quantified, it can be compared to a control. A control can be, e.g., the average or median amount of marker present in comparable samples of normal subjects in whom neural injury and/or neural disorders, is undetectable. The control amount is measured under the same or substantially similar experimental conditions as in measuring the test amount. For example, if a test sample is obtained from a subject's cerebrospinal fluid and/or blood serum sample and a marker is detected using a particular probe, then a control amount of the marker is preferably determined from a serum sample of a patient using the same probe. It is preferred that the control amount of marker is determined based upon a significant number of samples from normal subjects who do not have neural injury and/or neuronal disorders so that it reflects variations of the marker amounts in that population.

Data generated by mass spectrometry can then be analyzed by a computer software. The software can comprise code that converts signal from the mass spectrometer into computer readable form. The software also can include code that applies an algorithm to the analysis of the signal to determine whether the signal represents a "peak" in the signal corresponding to a marker of this invention, or other useful markers. The software also can include code that executes an algorithm that compares signal from a test sample to a typical signal characteristic of "normal" and human neural injury and determines the closeness of fit between the two signals. The software also can include code indicating which the test sample is closest to, thereby providing a probable diagnosis.

In a preferred embodiment, the biomarkers are detected in a wide range of species, such as for example, mammals, bird, fish, reptiles. For example, synaptotagmin-1 is found in many species and is highly conserved. Below is an example of synaptotagmin-1 taxonomic data.

Taxonomy Report

| | | | |
|---|---|---|---|
| *Bilateria* | 200 hits | 23 orgs | [root; cellular organisms; *Eukaryota; Fungi/Metazoa* group; *Metazoa; Eumetazoa*] |
| *Coelomata* | 195 hits | 22 orgs | |
| *Chordata* | 170 hits | 18 orgs | [*Deuterostomia*] |
| *Gnathostomata* | 163 hits | 14 orgs | [*Craniata*; *Vertebrata*] |
| *Euteleostomi* | 163 hits | 13 orgs | [*Teleostomi*] |
| *Tetrapoda* | 142 hits | 11 orgs | [*Sarcopterygii*] |
| *Amniota* | 141 hits | 10 orgs | |
| *Estherio* | 134 hits | 3 orgs | [*Mammalia*; *Theria*] |
| *Laurasiatheria* | 24 hits | 2 orgs | |
| *Bos taurus* | 11 hits | 1 orgs | [*Cetartiodactyla*; *Ruminantia*; *Pecora*; *Bovidae*; *Bovinae*; *Bos*] |
| *Canis familiaris* | 13 hits | 1 orgs | [*Carnivora*; *Fissopedia*; *Canidae*; *Canis]* |
| *Euarchontoglires* | 110 hits | 7 orgs | |
| *Catarrhini* | 33 hits | 4 orgs | [Primates; *Simiiformes]* |
| *Hominidae* | 36 hits | 3 orgs | [*Hominoidea*] |
| *Pongo pygmeus* | 4 hits | 1 orgs | [*Pongo*] |
| *Homo*/*Pan*/Gorilla group | 30 hits | 2 orgs | |
| *Homo sapiens* | 20 hits | 1 orgs | [*Homo*] |
| *Pan troglodytes* | 10 hits | 1 orgs | [*Pan]* |
| *Macaca fascicularis* | 7 hits | 1 orgs | [*Cercopithecoidea*; *Cercopithecidae*; *Cercopithecinae*; *Macaca*] |
| *Murinae* | 71 hits | 3 orgs | [*Glirea*; *Rodentia*; *Sciurognathi*; *Muridae*] |
| *Rattus* | 43 hits | 2 orgs | |
| *Rattus rattus* | 31 hits | 1 orgs | |
| *Rattus norvegicus* | 40 hits | 1 orgs | |
| *Mus musculus* | 26 hits | 1 orgs | [*Mus*] |
| *Gallus gallus* | 7 hits | 1 orgs | [*Sauropsida*; *Sauria*; *Archosauria*; *Aves*; *Neognathae*; *Galliforme*; *Phasianidae*; *Phasianinae*; *Gaullus*] |
| *Xenopus laevis* | 1 hits | 1 orgs | [*Amphibia*; *Batrachia*; *Anura*; *Mesobatrachia*; *Pipoidea*; *Pipidae*; *Xenopodinae*; *Xenopus*; *Xenopus*] |

-continued

| Taxonomy Report | | | |
|---|---|---|---|
| *Clupeocephala* | 23 hits | 2 orgs | [*Actinopterygii*; *Actinopteri*; *Neopterygii*; *Teleostei*; *Elopocephala*] |
| *Danio rerio* | 11 hits | 1 orgs | [*Otocephala*; *Ostariophysi*; *Otophysi*; *Cypriniphysi*; *Cypriniformes*; *Cyprinoidea*; *Cyprinidae*; *Rasborinae*; *Danio*] |
| *Tetraodon nigroviridis* | 12 hits | 1 orgs | [*Euteleostei*; *Neognathi*; *Neoteleostei*; *Eurypterygii*; *Ctenosquamata*; *Acanthomorpha*; *Euacanthomorpha*; *Holacanthopt*] |
| *Discopyge ommata* | 4 hits | 1 orgs | [*Chondrichthyes*; *Elasmobranchii*; *Neoselachii*; *Sgualea*; *Hypnosqualea*; *Pristorajea*; *Batoidea*; *Torpediniformes*] |
| *Halocynthia roretzi* | 1 hits | 1 orgs | [*Urochordata*; *Ascidiacea*; *Stolidobranchia*; *Pyuridae*; *Halocynthia*] |
| *Protostomia* | 18 hits | 7 orgs | |
| *Mollusca* | 3 hits | 3 orgs | |
| *Gastropoda* | 3 hits | 2 orgs | |
| *Lymnaea stagnalis* | 1 hits | 1 orgs | [*Pulmonata*; *Basommatophora*; *Lymnaeoidea*; *Lymnaeidae*; *Lymnaea*] |
| *Aplysia californica* | 2 hits | 1 orgs | [*Orthogastropoda*; *Apogastropoda*; *Heterobranchia*; *Euthyneura*; *Opisthobranchia*; *Anaspidea*; *Aplysioidea*; *Aplysiidae*] |
| *Loligo pealei* | 2 hits | 1 orgs | [*Cephalopoda*; *Coleoidea*; *Neocoleoidea*; *Decapodiformes*; *Loliginidae*; *Loligo*] |
| *Endopterygota* | 13 hits | 4 orgs | [*Panarthropoda*; *Arthropoda*; *Mandibulata*; *Pancrustacea*; *Hexapoda*; *Insecta*; *Dicondylia*; *Pterygota*] |
| *Apis mellifera* | 2 hits | 1 orgs | [*Hymenoptera*; *Aculeata*; *Apoidea*; *Apidae*; *Apinae*; *Apini*; *Apis*] |
| *Manduca sexta* | 2 hits | 1 orgs | [*Amphiesmenoptera*; *Lepidoptera*; *Glossata*; *Neolepidoptera*; *Heteroneura*; *Ditrysia*; *Obtectomera*; *Bombycoidea*; *Sphin*] |
| *Sophophora* | 3 hits | 2 orgs | [*Diptera*; *Brachycera*; *Muscomorpha*; *Schizophora*; *Acalyptratae*; *Ephydroidea*; *Drosophilidae*; *Droso*] |
| *Drosophila melanogaster* | 2 hits | 1 orgs | [*melanogaster* group; *melanogaster* subgroup] |
| *Drosophila pseudoobscura* | 1 hits | 1 orgs | [*obscura* group; *pseudoobscura* subgroup] |
| *Dugesia japonica* | 1 hits | 1 orgs | [*Acoelomata*; *Platyhelminthes*; *Turbellaria*; *Seriata*; *Tricladida*; *Paludicola*; *Dugesiidae*; *Dugesia*] |
| *Caenorhabditis* | 11 hits | 2 orgs | [*Pseudocoelomata*; *Nematoda*; *Chromadorea*; *Rhabditida*; *Rhabditoidea*; *Rhabditidae*; *Peloderinae*] |
| *Caenorhabditis elegans* | 7 hits | 1 orgs | |
| *Caenorhabditis briggsae* | 4 hits | 1 orgs | |

Production of Antibodies to Detect Cleavage Products

Cleavage products due to the enzymatic activity of the proteolytic enzyme biomarkers of their substrates can also be detected. Cleavage products obtained from samples in patients suffering from varying neural injuries, degrees of severity of injury, neuronal disorders fragments and derivatives thereof, can be prepared as described above. Furthermore, cleavage products can be subjected to enzymatic digestion to obtain fragments or peptides of the biomarkers for the production of antibodies to different antigenic epitopes that can be present in a peptide versus the whole protein. Antigenic epitopes are useful, for example, to raise antibodies, including monoclonal antibodies, that specifically bind the epitope. Antigenic epitopes can be used as the target molecules in immunoassays. (See, for instance, Wilson et al., *Cell* 37:767-778 (1984); Sutcliffe et al., *Science* 219:660-666 (1983)).

In a preferred embodiment, the antibodies specifically bind biomarkers identified by SEQ ID NO's.: 1-148. Epitopes, identified by SEQ ID NO's.: 1-149, can be as short as at least about 3 amino acids in length. Antibodies directed to SEQ ID NO's.: 1-149 can also include epitopes that are directed to the N- and C-terminal regions of biomarkers identified by SEQ ID NO's.: 1-149. Full length proteins and/or longer fragments than those identified by SEQ ID NO's.: 1-149 disclosed in Table 1, including accession numbers, for production of antibodies to longer fragments. The antibodies can be directed to longer N- and/or C-Terminal fragments as identified by SEQ ID NO's.: 1-149 and/or epitopes spanning the identified cleavage sites (see table 2) and can be as short as three amino acids up to 500 amino acids long. See for example Table 1 for identity of full length proteins. Examples include, but not limited to: achromopeptidase, aminopeptidase, angiotensin Converting Enzyme, bromelain, calpain, calpain I, calpain II, carboxypeptidase A, carboxypeptidase B, carboxypeptidase G, carboxypeptidase P, carboxypeptidase W, carboxypeptidase Y, caspase, caspase 1, caspase 2, caspase 3, caspase 4, caspase 5, caspase 6, caspase 7, caspase 8, caspase 9, caspase 10, caspase 13, cathepsin B, cathepsin C, cathepsin D, cathepsin G, cathepsin H, cathepsin L, chymopapain, chymase, chymotrypsin, α-clostripain, collagenase, complement C1r, complement C1s, complement Factor D, complement factor I, cucumisin, dipeptidyl peptidase IV, elastase, leukocyte, elastase, pancreatic, endoproteinase Arg-C, endoproteinase Asp-N, endoproteinase Glu-C, endoproteinase Lys-C, enterokinase, Factor Xa, ficin, furin, granzyme A, granzyme B, HIV Protease, Igase, kallikrein tissue, kinase, leucine aminopeptidases, microsomal, matrix metalloprotease, methionine aminopeptidase, neutrase, papain, pepsin, plasmin, prolidase, pronase E, prostate specific antigen, protease, protease S, proteinase, proteinase 3, proteinase A, proteinase K, protein C, pyroglutamate aminopeptidase, thrombin, tissue plasminogen activator, troponins, trypsin, tryptase, urokinase; and, at least one or more peptides identified by SEQ ID NO's.: I-149.

Cleavage products can be used, for example, to induce antibodies according to methods well known in the art. (See, for instance, Sutcliffe et al., supra; Wilson et al., supra; Chow et al., *Proc. Natl. Acad. Sci.* USA 82:910-914; and Bittle et al., *J. Gen. Virol.* 66:2347-2354 (1985). Cleaved neural polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.,* 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Nucleic acids cleavage product epitopes can also be recombined with a gene of interest as an epitope tag (e.g., the hemaglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, *Proc. Natl. Acad. Sci. USA* 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

The antibodies of the present invention may be generated by any suitable method known in the art. The antibodies of the present invention can comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988), which is hereby incorporated herein by reference in its entirety). For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides as may be described herein.

Typically, the immunizing agent and/or adjuvant will be injected in the animal by multiple subcutaneous or intraperitoneal injections, though they may also be given intramuscularly, and/or through IV. The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivatizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention can also comprise monoclonal antibodies. Monoclonal antibodies may be prepared using hybridoma methods, such as those described by Kohler and Milstein, *Nature,* 256:495 (1975) and U.S. Pat. No. 4,376,110, by Harlow, et al., Antibodies: A Laboratory Manual, (Cold spring Harbor Laboratory Press, 2nd ed. (1988), by Hammerling, et al., Monoclonal Antibodies and T-Cell Hybridomas (Elsevier, N.Y., (1981)), or other methods known to the artisan. Other examples of methods which may be employed for producing monoclonal antibodies includes, but are not limited to, the human B-cell hybridoma technique (Kosbor et al., 1983, *Immunology Today* 4:72; Cole et al., 1983, *Proc. Natl. Acad. Sci.* USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include neural polypeptides, fragments or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. As inferred throughout the specification, human myeloma and mouse-human heteromyeloma cell lines also have been described for the production of human monoclonal antibodies (Kozbor, *J. Immunol.,* 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the neural polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoadsorbant assay (ELISA). Such techniques are known in the art and within the skill of the artisan. The binding affinity of the monoclonal antibody can, for example, be determined by the Scatchard analysis of Munson and Pollart, *Anal. Biochem.,* 107:220 (1980).

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hybridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hybridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells.

Methods for producing and screening for specific antibodies using hybridoma technology are routine and well known in the art. In a non-limiting example, mice can be immunized with a biomarker polypeptide or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention.

Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention. The antibodies detecting cleavage products, peptides and derivatives thereof, can be used in immunoassays and other methods to identify new cleavage products and for use in the diagnosis of neural injury, degree of severity of injury and/or neurological disorders.

Other methods can also be used for the large scale production of cleavage product specific antibodies. For example, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187 9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

The antibodies of the present invention have various utilities. For example, such antibodies may be used in diagnostic assays to detect the presence or quantification of the polypeptides of the invention in a sample. Such a diagnostic assay can comprise at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., *Anal Biochem.,* 278(2):123-131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp. 147-158). The antibodies used in the diagnostic assays can be labeled with a detectable moiety. The detectable moiety should be capable of producing, either directly or indirectly, a detectable signal. For example, the detectable moiety may be a radioisotope, such as $^{2}H$, $^{14}C$, $^{32}P$, or $^{125}I$, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., *Nature,* 144:945 (1962); David et al., *Biochem.,* 13:1014 (1974); Pain et al., *J. Immunol. Methods,* 40:219 (1981); and Nygren, *J. Histochem. and Cytochem.,* 30:407 (1982).

Kits

In yet another aspect, the invention provides kits for aiding a diagnosis of neural injury, degree of severity of injury, subcellular localization and/or neuronal disorders, wherein the kits can be used to detect the markers of the present invention. For example, the kits can be used to detect any one or more of the markers described herein, which markers are differentially present in samples of a patient and normal subjects. The kits of the invention have many applications. For example, the kits can be used to differentiate if a subject has axonal injury versus, for example, dendritic, or has a negative diagnosis, thus aiding neuronal injury diagnosis. In another example, the kits can be used to identify compounds that modulate expression of one or more of the markers in in vitro or in vivo animal models to determine the effects of treatment.

In one embodiment, a kit comprises (a) a composition or panel of biomarkers; (b) a protein substrate; and (c) a detection reagent. Such kits can be prepared from the materials described above, and the previous discussion regarding the materials (e.g., antibodies, detection reagents, immobilized supports, etc.) is fully applicable to this section and will not be repeated. Optionally, the kit may further comprise pre-fractionation spin columns. In some embodiments, the kit may further comprise instructions for suitable operation parameters in the form of a label or a separate insert.

In a preferred embodiment, the composition or panel of biomarkers includes at least one biomarker selected from any one biomarker identified by SEQ ID NO's.: 1-149. Preferably, the panel of biomarkers includes at least two biomarkers selected from SEQ ID NO's.: 1-149 up to 145 biomarkers selected from SEQ ID NO's.: 1-149.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Optionally, the kit may further comprise a standard or control information so that the test sample can be compared with the control information standard to determine if the test amount of a marker detected in a sample is a diagnostic amount consistent with a diagnosis of neural injury, degree of severity of the injury, subcellular localization, neuronal disorder and/or effect of treatment on the patient.

In another embodiment, a kit comprises: (a) a substrate comprising an adsorbent thereon, wherein the adsorbent is suitable for binding a marker, (b) any one biomarker up to one hundred and forty five biomarkers selected from biomarkers identified by SEQ ID NO's.: 1-149, and (c) instructions to detect the marker or markers by contacting a sample with the adsorbent and detecting the marker or markers retained by the adsorbent. In some embodiments, the kit may comprise an eluant (as an alternative or in combination with instructions) or instructions for making an eluant, wherein the combination of the adsorbent and the eluant allows detection of the markers using gas phase ion spectrometry. Such kits can be prepared from the materials described above, and the previous discussion of these materials (e.g., probe substrates, adsorbents, washing solutions, etc.) is fully applicable to this section and will not be repeated.

In another embodiment, the kit may comprise a first substrate comprising an adsorbent thereon (e.g., a particle functionalized with an adsorbent) and a second substrate onto which the first substrate can be positioned to form a probe which is removably insertable into a gas phase ion spectrometer. In other embodiments, the kit may comprise a single substrate which is in the form of a removably insertable probe with adsorbents on the substrate. In yet another embodiment, the kit may further comprise a pre-fractionation spin column (e.g., Cibacron blue agarose column, anti-HSA agarose column, size exclusion column, Q-anion exchange spin column, single stranded DNA column, lectin column, etc.).

Optionally, the kit can further comprise instructions for suitable operational parameters in the form of a label or a separate insert. For example, the kit may have standard instructions informing a consumer how to wash the probe after a sample is contacted on the probe. In another example, the kit may have instructions for pre-fractionating a sample to reduce complexity of proteins in the sample. In another example, the kit may have instructions for automating the fractionation or other processes.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is “prior art” to their invention.

EXAMPLES

Materials and Methods

In Vivo Model of Brain Injury Model.

A controlled cortical impact (CCI) device is used to model TBI in rats and generate brain tissue and CSF samples. Adult male (280-300 g) Sprague-Dawley rats (Harlan: Indianapolis, Ind.) are anesthetized with 4% isoflurane in a carrier gas of 1:1 $O_2/N_2O$ (4 min.) followed by maintenance anesthesia of 2.5% isoflurane in the same carrier gas. Core body temperature is monitored continuously by a rectal thermistor probe and maintained at 37±1° C. by placing an adjustable temperature controlled heating pad beneath the rats. Animals are mounted in a stereotactic frame in a prone position and secured by ear and incisor bars. A midline cranial incision is made, the soft tissues reflected, and a unilateral (ipsilateral to site of impact) craniotomy (7 mm diameter) is performed adjacent to the central suture, midway between bregma and lambda. The dura mater is kept intact over the cortex. Brain trauma is produced by impacting the right cortex (ipsilateral cortex) with a 5 mm diameter aluminum impactor tip (housed in a pneumatic cylinder) at a velocity of 3.5 m/s with a 1.6 mm compression and 150 ms dwell time (compression duration). These injuries are associated with different magnitudes of local cortical contusion and more diffuse axonal damage. Velocity is controlled by adjusting the pressure (compressed $N_2$) supplied to the pneumatic cylinder. Velocity and dwell time are measured by a linear velocity displacement transducer (LUCAS SHAEVITZ™ model 500 HR; Detroit, Mich.) that produces an analogue signal that is recorded by a storage-trace oscilloscope (BK Precision, model 2522B; Placentia, Calif.). Sham-injured control animals undergo identical surgical procedures but do not receive an impact injury. Appropriate pre- and post-injury management is maintained to insure compliance with guidelines set forth by the University of Florida Institutional Animal Care and Use Committee and the National Institutes of Health guidelines detailed in the Guide for the Care and Use of Laboratory Animals. Different brain tissue regions, CSF, and serum samples are collected at a maximum of 7 tie points (6, 12, and 24 hours, and 2, 3, 7, and 14 days) after CCI, as described below.

Similarly, multi-organ injury can be induced by sepsis in rats using methods well-known in the art.

Brain Tissue Collection and Preparation

At the appropriate time-points (6, 12, 24, 48 and 72 h, 5 and 7 days) after injury, animals are anesthetized and immediately killed by decapitation. Organ tissue is immediately removed, rinsed with ice cold PBS and halved. Different regions (if desired) are rapidly dissected, rinsed in ice cold PBS, snap-frozen in liquid nitrogen, and frozen at −80° C. until used. For Western blot analysis, the brain samples are pulverized with a small mortar-pestle set over dry ice to a fine powder. The pulverized brain tissue powder is then lysed for 90 min at 4° C. with 50 mM Tris (pH 7.4), 5 mM EDTA, 1% (v/v) Triton X-100, 1 mM DTT, 1× protease inhibitor cocktail (Roche Biochemicals). The brain lysates are then centrifuged at 8000 g for 5 min at 4° C. to clear and remove insoluble debris, snap-frozen and stored at −85° C. until used.

SDS-Polyacrylamide Gel Electrophoresis and Electrotransfer.

Protein concentrations of tissue lysates and CSF are determined by bicinchoninic acid microprotein assays (Pierce Inc., Rockford, Ill., USA) with albumin standards. Protein balanced samples are prepared for sodium dodecyl sulfate-polyacrylamide gel electrophoresis (SDS-PAGE) in two-fold loading buffer containing 0.25 M Tris (pH 6.8), 0.2 M DTT, 8% SDS, 0.02% bromophenol blue, and 20% glycerol in distilled $H_2O$. Twenty micrograms (20 μg) of protein per lane will be routinely resolved by SDS-PAGE on 6.5% Tris/glycine gels for 2 h at 200 V. Following electrophoresis, separated proteins will be laterally transferred to polyvinylidene fluoride (PVDF) membranes in a transfer buffer containing 0.500 M glycine and 0.025 M Tris-HCl (pH 8.3) 10% methanol at a constant voltage of 20 V for 2 h at 4° C. in a semi-dry transfer unit (Bio-Rad).

Sandwich ELISA.

Anti-Biomarker specific rabbit polyclonal antibody and monoclonal antibodies are produced in the laboratory. To determine reactivity and specificity of the antibodies a tissue panel is probed by Western blot. An indirect ELISA is used with the recombinant biomarker protein attached to the ELISA plate to determine the optimal concentrations of the antibodies used in the assay. This assay determines a robust concentration of anti-biomarker to use in the assay. 96-well microplate wells are coated with 50 ng/well and the rabbit and mouse anti-biomarker antibodies are diluted serially starting with a 1:250 dilution down to 1:10,000 to determine the optimum concentration to use for the assay. A secondary anti-rabbit (or mouse)-horseradish peroxidase (HRP) labeled detection antibody and Ultra-TMB are used as detection substrate to evaluate the results.

Once the concentration of antibody for maximum signal is determined, maximum detection limit of the indirect ELISA for each antibody is determined. 96-well microplates are coated with a concentration from 50 ng/well serially diluted to <1 pg/well. For detection antibodies are diluted to the concentration determined above. This provides a sensitivity range for the Biomarker ELISA assays and determines which antibody to chose for capture and detection antibody.

Optimization and enhancement of signal in the sandwich ELISA: The detection antibody is directly labeled with HRP to avoid any cross reactivity and to be able to enhance the signal with the amplification system, which is very sensitive. This format is used in detecting all the biomarkers. The wells of the 96-well plate are coated with saturating concentrations of purified antibody (~250 ng/well), the concentration of biomarker antigen ranges from 50 ng to <1 pg/well and the detection antibody is at the concentration determined above. Initially the complex is detected with a HRP-labeled secondary antibody to confirm the SW ELISA format, and the detection system is replaced by the HRP-labeled detection antibody.

Standard curves of biomarkers and samples from control and injured animals are used. This also determines parallelism between the serum samples and the standard curve. Serum samples are spiked with a serial dilution of each biomarker, similar to the standard curve. Parallel results are equal to 80-100% recovery. If any high concentrations of serum have interfering substances, the minimum dilution required is determined to remove the interference. The assay is used to evaluate biomarker levels in serum from injured animals having injuries of different magnitudes followed over time.

Immunoblotting Analysis

After electrotransfer, blotting membranes are blocked for 1 h at ambient temperature in 5% non-fat milk in TBS and 0.05% Tween-2 (TBST), then incubated in primary monoclonal or polyclonal antibody in TBST with 5% milk (see list below, at 1/1000 to 1/3,000 dilution as recommended by the manufacturer) at 4° C. overnight, followed by four washes with TBST and a 2 hour incubation at ambient temperature with either a secondary antibody linked to horseradish peroxidase (enhanced chemiluminescence, (ELC) method) or biotinylated secondary antibody (Amersham) followed by a 30 min incubation with strepavidin-conjugated alkaline phosphatase (calorimetric method). ECL reagents (Amersham) are used to visualize the immunolabeling on x-ray film. Alternatively, colorimetric development is performed with a one-step BCIP-reagent (Sigma). Molecular weight of intact proteins and their potential breakdown products (BDP) are assessed by running along side rainbow colored molecular weight standards (Amersham). Semi-quantitative evaluation of protein and BDP's levels are performed via computer-assisted densitometric scanning (Epson XL3500 high resolution flatbed scanner) and image analysis with Image J software (NIH).

In vivo cleavage sites identification: To identify the major in vivo cleavage sites of each proteolysis-prone axonal and myelin structural protein, brain tissue is pooled from injured rats at a time point that optimally produced the major BDP. To obtain the maximal yield, tissue sampling combines ipsilateral cortex, subcortical white matter and corpus callosum. The pooled brain lysate using Triton X-100 is prepared as described under: Brain tissue collection and preparation (see above). The lysate (5 mg protein) is subjected to strong anion exchange chromatography (1.0 mm diameter, 10 cm long) using the BioRad Dualflow Biological system. The bound proteins are eluted with a NaCl gradient 20-500 mM) and 30-50 fractions collected. Fractions containing the specific proteins and fragments of interest are determined by subjecting 20 microliter of each fraction to SDS-PAGE Western blot analysis. In this manner, both the intact protein substrate and its major BDP(s) will be isolated. These proteins are then further separated by SDS-PAGE and electrotransfer to PVDF members. The now separated BDP and intact protein bands are visualized by Coomassie blue staining (80% Methanol, 5% acetic acid and 0.05% Coomassie brilliant blue R250 for 1 min. The BDP band is cut out and subjected to N-terminal microsequencing or trypsinization and mass spectrometry analysis to identify its new N-terminal. By matching the sequence generated from proteomic analysis with the full-length protein sequences in the rat proteome database with bioinformatic tools such as MASCOT, the major cleavage site of the protein substrate can be identified. Using this method, cleavage sites from proteins of interest have been identified (see Table 1 and Table 2).

In Vitro Protease Digestion and Cleavage Site Identification

In vitro protease digestion of purified tissue proteins (10-50 μg) with purified proteases (0.1-2.5 μg human calpain-1 and porcine calpain-2, (Calbiochem)), recombinant human caspase-3 caspase-6 and 7 (Chemicon), bovine cathepsin B (Sigma) and human MMP-2 and MMP-9 (Chemicon) was performed with a substrate to protease ratio of 1/200 to 1/40 for 2 hours to overnight in a buffer containing 50 mM HEPES (pH 7.4) with the exception of cathepsin B (with which we use 100 mM MES, pH 5.5). 10 mM dithiothreitol was also added for cysteine proteases (calpains, caspases and cathepsin B) but not MMP's. In addition, 1 mM EDTA was added for caspases while 2 mM excess $CaCl_2$ is added. The protease reaction is stopped by the addition of a protease inhibitor cocktail (Roche). The digested brain lysate is subjected to immunoprecipitation and cleavage site identification as described above. The in vitro cleavage pattern of a specific axonal or myelin protein of interest a is compared side-by side with the in vivo TBI-induced cleavage pattern by Western blot analysis (10 μg).

Preparation of Novel Fragment-Specific Antibodies and ELISA Development and Usage (a) Generation of Fragment-Specific Polyclonal Antibodies Once the new N-terminal of a BDP can be identified, it is possible to raise fragment-specific antibodies using our established and unique technique.

TBDP-26kDa

| | |
|---|---|
| ARVAGVS$_{121}$^K$_{122}$DRTGN | SEQ ID NO: 145 |
| ARVAGVS$_{-COOH}$; | SEQ ID NO: 146 |
| $_{NH2-}$KDRTGNDE | SEQ ID NO: 147 |

Using tau protein as an example, tau has a unique cleavage site (ARVAGVS$_{121}$^K$_{122}$DRTGN) (SEQ ID NO: 145), synthetic peptide NH2-Cys-C$_6$-ARVAGVS$_{_COOH}$ (SEQ ID NO: 146) and ($_{NH2}$-KDRTGNDE-C$_6$ Cys-OH) (SEQ ID NO: 147) based on the new C-terminal or N-terminal of the two Tau-BDPs-26 kDa are custom-made (California Peptide, Napa, Calif.). A $C_6$ linker and a C-terminal cysteine [C] will be introduced for the subsequent coupling of the peptide to Keyhole Limpet hemocyanin (KLH) protein using a sulfo-link crosslinking reagent (Pierce). Following coupling efficiency determinations, peptides are dialyzed, concentrated and 2 mg of conjugated protein will be used for multiple antigen injections into 2 rabbits. After 3 months, serum samples from the rabbits are collected and subjected to affinity purification using $NH_2$-Cys-C$_6$-ARVAGVS$_{_COOH}$ (SEQ ID NO: 146) or ($_{NH2}$-KDRTGNDE-C$_6$-Cys-OH) (SEQ ID NO: 147) coupled to sulfo-linked resins (Pierce). The affinity-purified antibody is dialyzed against TBS (20 mM Tris-HCl, pH 7.4, 150 mM NaCl), concentrated and stored in 50% glycerol at −20° C. Confirmation of the specificity of antibodies for Tau-BDPs-26 kDa employs Western blot comparisons to BDPs assessed with a monoclonal antibody to total αII-spectrin following challenge of rats with mild and moderate TBI, as well as cell or brain lysate digested by different proteases (such as calpain or caspases), a technique we previously employed. Similarly, monoclonal antibodies can also be generated.

(b) Fragment-Specific ELISA's Development and Usage

To illustrate the method of making fragment-specific enzyme-linked immunoassay (ELISA), Tau-BDP-26 kDa is used as an example: First Western blotting is used to confirm the immunoreactivity of commercial monoclonal antibodies that recognize rat tau and its BDPs (Cedarlane, clone Tau-1) and polyclonal anti-Tau-BDP-26 kDa antibodies. 10 μg/ml of the polyclonal anti-Tau-BDP-26 kDa antibody is used as capture antibody to coat 96-well ELISA microplate wells in 0.1M carbonate-bicarbonate Buffer pH 9.8 overnight. After rinsing each well with 200 μL PBS with 0.05% Tween 20 three times, non-specific sites are blocked with blocking buffer (0.1% BSA, 0.05% Tween 20 in PBS) for 1 hour at room temperature. Brain tissue lysate (1-25 μg) or CSF samples (2.5-10 μl) from control and TBI animals are diluted with blocking buffer to 100 μl and added to each well. The plate is incubated on shaker at 150, rpm, 26° C. for 30 minutes to 2 h. After rinsing each well with 200 μl PBS with 0.05% Tween 20 three times, the wells are probed with detecting commercial monoclonal antibodies that recognize rat tau and its BDPs fragment-specific antibody at 1 μg/ml with blocking buffer (100 μl) and incubated at 150 rpm, 26° C. for 30-60 minutes. The washing steps are repeated and the plate probed with HRP-coupled secondary antibody (1/20,000) (Pierce), washed again before developing with 100 μl of TMB substrate solution (Ultra-sensitive ABC peroxidase Reagent, Pierce) (Pierce product number 34028) with incubation at 150 rpm, 26° C. for 5-30 minutes. After the addition of 50-μl stop solution (1N $H_2SO_4$) to each well (5 min), the plate is read at $OD_{450}$ nm with a spectrophotometer. This sandwich ELISA format selectively detects Tau-BDP-26 kDa but not the intact Tau or other BDP's present in biological samples.

Example 1

Figures 3A, 3B:
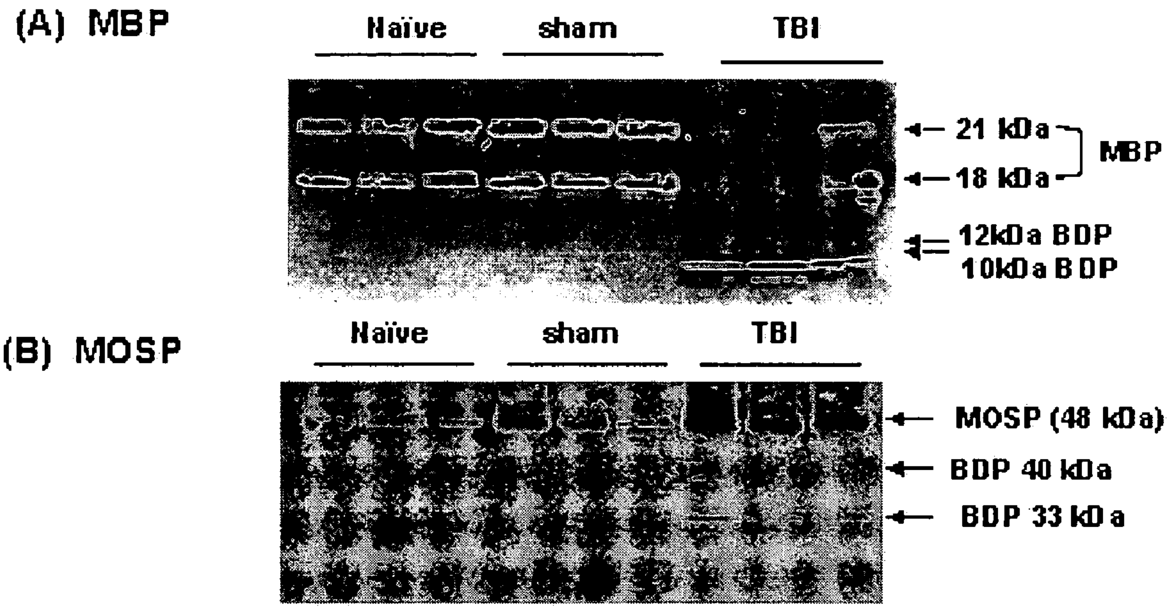
FIGS. 3A and 3B are gels showing examples of Myelin proteins (MBP, FIG. 3A; MOSP, FIG. 3B) being cleaved 24 hours after traumatic brain injury.
Figures 4A, 4B, 4C:
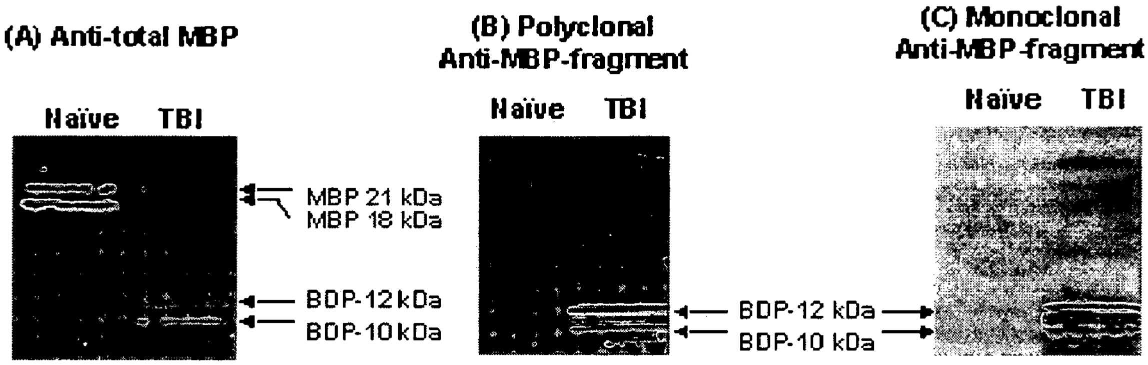
FIGS. 4A-4C are gels showing examples of production of polyclonal and monoclonal antibodies that specifically detects a unique new N-terminal of a tissue protein fragment (MBP-BDP). Naïve and TBI ipsilateral cortex samples (48 hr after injury) were analyzed on immunoblots probed with anti-total MBP antibody (FIG. 4A), anti-MBP fragment-specific rabbit polyclonal (FIG. 4B): or mouse monoclonal (FIG. 4C) antibodies.

Detection of Neural Proteins Subjected to Proteolytic Attack 48 h after Traumatic Brain Injury (TBI) in Rats TBI was induced in rodents as described above. 48 h following TBI or sham operation or naïve rats, samples of CSF were collected and analyzed for presence of five novel neural protein markers (MBP and MOSP) (FIG. 3) were identified to be vulnerable to endogenous proteolytic attack, producing major breakdown products (BDPs) in the ipsilateral hippocampus. Ipsilateral cortical samples were also analyzed and they showed very similar patterns of proteolysis. Based on the unique cleavage site in MBP (DENPVVHFF$_{114}$K$_{115}$NIVTPP) SEQ ID NO: 184), we have produced polyclonal and monoclonal that specifically detects the new N-terminal (NH2-KNIVTPP) (SEQ ID NO: 149) of MBP-BDP of 12 kDa and 10 kDa (FIG. 4). These unique BDP's when accumulated in biofluids such as CSF and blood are excellent diagnostic markers for organ-specific (brain, spinal cord or peripheral nerve) injury or stress and can be detected by techniques using fragment-specific antibody tools such as those described in FIG. 4 by Western blots or ELISA.

Example 2

Detection of Myelin Proteins Subjected to Proteolytic Attack 48 h after Traumatic Brain Injury (TBI) in Rats TBI was induced in rodents as described above. 48 h following TBI or sham operation of on naïve rats, samples of CSF were collected and analyzed for presence of two novel myelin sheath protein markers; (MBP and MOSP) (FIG. 3) were identified to be vulnerable to endogenous proteolytic attack, producing major breakdown products (BDPs) in the ipsilateral hippocampus. Ipsilateral cortical samples were also analyzed and they showed very similar patterns of proteolysis. Based on the unique cleavage site in MBP (DENPVVHFF$_{114}$^K$_{115}$NIVTPP), (SEQ ID NO: 148) we have produced polyclonal and monoclonal antibodies that specifically detect the new N-terminal (NH2-KNIVTPP), SEQ ID NO: 149) of MBP-BDP of 12 kDa and 10 kDa (FIG. 4). These unique BDP's when accumulated in biofluids such as CSF and blood are excellent diagnostic markers for organ-specific (brain, spinal cord or peripheral nerve) injury or stress and can be detected by techniques using fragment-specific antibody tools such as those described in FIG. 4 by Western blots or ELISA.

Example 3

Figure 5:
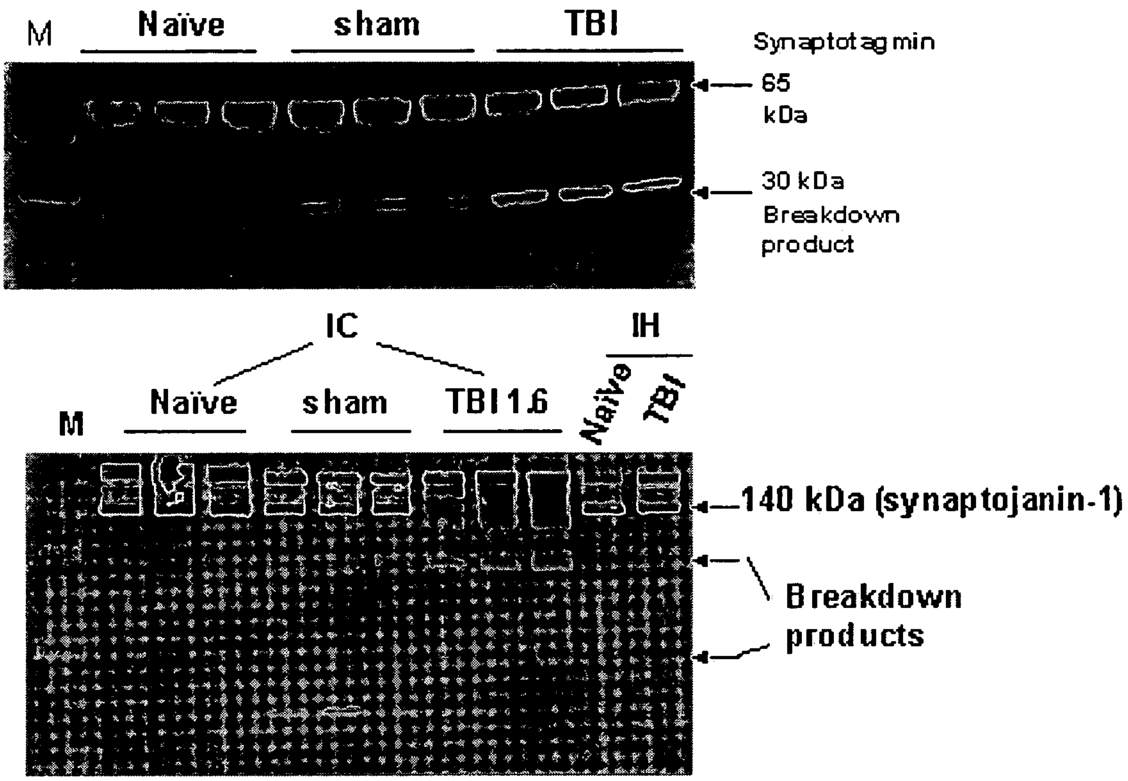
FIG. 5 shows gels of examples of Synaptic proteins (Synaptotagmin and Synaptojanin-1) being degraded in rat cortex and/or hippocampus 48 hr after TBI.

Detection of Synaptic Proteins (Synaptotagmin and Synaptojanin-1) are being Degraded in Rat Cortex and/or Hippocampus 48 hr after TBI in Rats TBI was induced in rodents as described above. 48 h following TBI or sham operation on naïve rats, samples of CSF were collected and analyzed for presence of five novel synaptic protein markers; Synaptotagmin (top), and Synaptojanin-1 (bottom) (FIG. 5) were identified to be vulnerable to endogenous proteolytic attack, producing major breakdown products (BDPs) in the ipsilateral hippocampus. Ipsilateral cortical samples were also analyzed and they showed very similar patterns of proteolysis. These unique BDP's when accumulated in biofluids such as CSF and blood, can be detected by immunological techniques such as Western blots or ELISA and thus are excellent diagnostic marker for organ-specific (brain or spinal cord or peripheral nerve) injury or stress (FIG. 1).

Example 4

Figure 6:
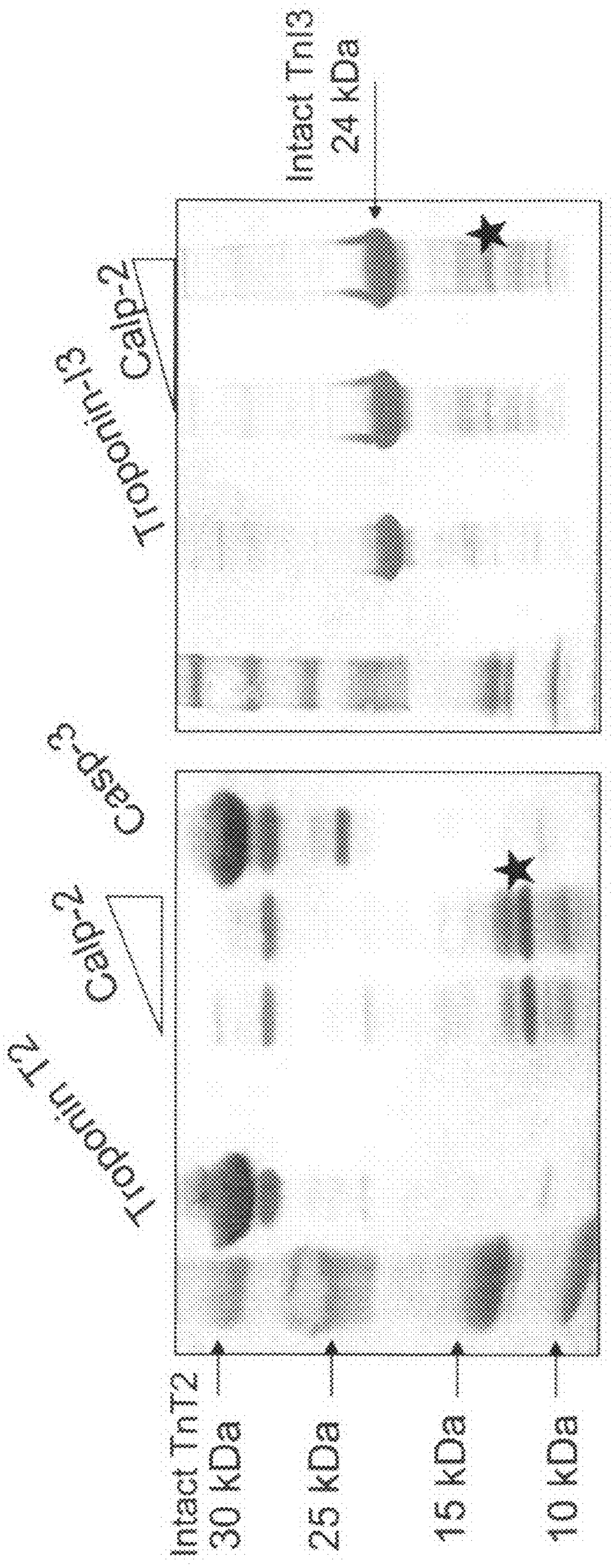
FIG. 6 shows gels of the results obtained when human cardiac Troponin-T2 and Troponin-I3 cleaved by calpain-2 and caspase-3 proteases, producing unique breakdown products (designated by a star).
Figure 7:
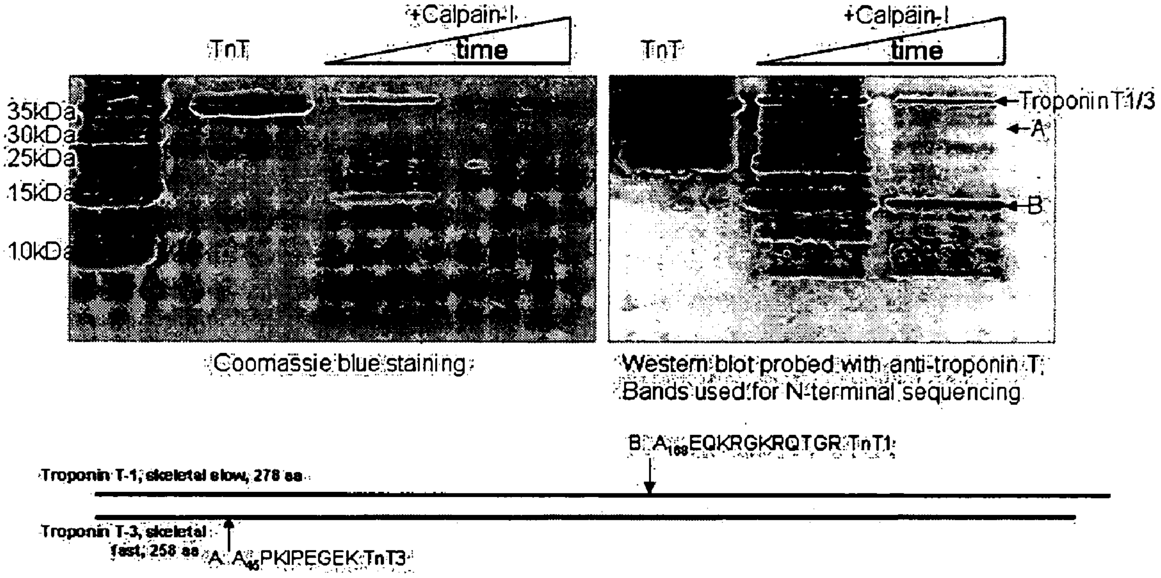
FIG. 7 shows gels of the results obtained when human muscle Troponin-T13 was digested by calpain-1 protease, producing unique breakdown products. The Coomassie stained PVDF membrane was used to excise bands for N-terminal sequencing. Western blot shows identification of most of the bands as specific TnT BDPs. The map below indicates the newly identified cleavage sites, one in TnT1 and one in TnT2.

Detection of Major Cardiac Troponin-T2 and Troponin-I32 were Cleaved by Calpain-2 and Caspase-3 Proteases, Producing Unique Breakdown Products Cardiac stress, heart failure or cardiac ischemia induce overactivation of proteases such as calpain and caspase-3. Purified human cardiac isoforms of troponin T2 and troponin-I3 are subjected to in vitro incubation with calpain and/or caspase-3. We found that both troponins are vulnerable to proteolytic attack (FIG. 6) producing major breakdown products (BDPs) in the process. We expect that the same BDP's will be produced in cardiac injury or stressing animals and in humans. These unique BDP's when accumulated in biofluids such as blood, can be readily detected by immunological techniques such as Western blots or ELISA and thus are excellent diagnostic markers for organ-specific (heart) injury or stress (FIG. 1).

Example

Detection of Unobvious and Unique Cleavage Sites of Major Organ or Tissue Proteins in Stressed or Injured Animals or During In Vitro Protease Incubation Using the methods described above and similar to outlined in example 1-3, at least 43 unobvious and unique cleavage sites of major organ or tissue proteins (Table 2; SEQ ID NO's.: 1-149) have been identified. The exact cleavage sites enable the synthesis of peptides that mimic the new C-terminal or new N-terminal epitope and these can then be used to generate fragment-specific antibodies or other capture or detecting agents. These unique BDP's when accumulated in biofluids such as blood, can be readily detected by the methods described herein, e.g. immunological techniques such as Western blots or ELISA and thus are excellent diagnostic markers for organ-specific (heart) injury or stress (FIG. 1).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 2

Examples of unobvious and unique tissue protein cleavage sites produce by protease attack

| Protein | Molecular weight Protein | Acc. # | Species | BDP | Molecular weight BDP | Cleavage site identified | Example of new C-and N-terminal epitopes for fragment-specific antibodies |
|---|---|---|---|---|---|---|---|
| alphaII-spectrin | 260 kDa | hypothetical | Dog | SBDP150-Short | 150 kDa | WRSLQQLAEERSEVY$_{1173}$* G$_{1174}$MMPRD DTDSKTASP SEQ ID NO.: 1 | WRSLQQLAEERSEVY$_{-COOH}$; SEQ ID NO: 49 $_{NH2-}$GMMPRDDTDSKTASP SEQ ID NO: 50 |
| Fast skeletal muscle Tropo-nin-T3 | 33 kDa | NP_006748 | Human | TnT3BDP | 22 kDa | AEEDAEEEKPRPKLT$_{44}$* A$_{45}$PKIPEGEKVDFDDIQ SEQ ID NO: 2 | AEEDAEEEKPRPKLT$_{COOH}$; SEQ ID NO: 51 $_{NH2}$APKIPEGEKVDFDDIQ SEQ ID NO: 52 |
| Fast sketal muscle Troponin I-2 (1) | 22 kDa | NP_003273 | Human | TnI2BDP | <10 kDa | PPLRRVRMSADAMLK$_{124}$* A$_{125}$LLGSKHKVCMDLRAN SEQ ID NO: 3 | PPLRRVRMSADAMLK$_{COOH}$ SEQ ID NO: 53 $_{NH2}$ALLGSKHKVCMDLRAN SEQ ID NO: 54 |
| Fast sketal muscle Troponin I-2 (2) | 22 kDa | NP_003273 | Human | TnI2BDP | <10 kDa | GSKHKVCMDLRANLK$_{142}$* Q$_{143}$VKKEDTEKERDLRDV SEQ ID NO: 4 | GSKHKVCMDLRANLK$_{COOH}$ SEQ ID NO: 55 $_{NH2}$QVKKEDTEKERDLRDV SEQ ID NO: 56 |

TABLE 2-continued

Examples of unobvious and unique tissue protein cleavage sites produce by protease attack

| Protein | Molecular weight Protein | Acc. # | Species | BDP | Molecular weight BDP | Cleavage site identified | Example of new C-and N-terminal epitopes for fragment-specific antibodies |
|---|---|---|---|---|---|---|---|
| Fast sketal muscle Troponin I-2 (3) | 22 kDa | NP_003273 | Human | TnI2BDP | <10 kDa | EEEKYDMEVRVQKTS$_{90}$*<br>K$_{91}$ELEDMNQKLFDLRGK<br>SEQ ID NO: 5 | EEEKYDMEVRVQKTS$_{COOH}$<br>SEQ ID NO: 57<br>$_{NH2}$KELEDMNQKLFDLRGK<br>SEQ ID NO: 58 |
| Slow skeletal muscle Tro-ponin-T1 | 33 kDa | NP_003274 | Human | TnT1BDP | 12 kDa | VLSNMGAHFGGYLVK$_{167}$*<br>A$_{168}$EQKRGKRQT<br>SEQ ID NO: 6 | VLSNMGAHFGGYLVK$_{COOH}$<br>SEQ ID NO: 59<br>$_{NH2}$AEQKRGKRQTGREMKV<br>SEQ ID NO: 60 |
| Slow/Fast skeletal muscle Troponin I1 and I2 | 22 kDa | NP_006748 | Human | TnT3BDP | <10 kDa | TREIKDLKLKVMDLR$_{115}$*<br>G$_{116}$KFKRPPLRRVRVSA<br>SEQ ID NO: 7 | TREIKDLKLKVMDLR$_{COOH}$<br>SEQ ID NO: 61<br>$_{NH2}$GKFKRPPLRRVRVSA<br>SEQ ID NO: 62 |
| Fast skeletal muscle Tro-ponin-I1 | 22 kDa | NP_003273 | Human | TrI1BDP | | KELEDMNQKLFDLRG$_{106}$↓<br>K$_{107}$FKRPPLRRVRMSAD<br>SEQ ID NO: 8 | KELEDMNQKLFDLLRG$_{COOH}$;<br>SEQ ID NO: 63<br>$_{NH2-}$KFKRPPLRRVRMSAD<br>SEQ ID NO: 64 |
| Fast skeletal muscle Tro-ponin-T3 | 33 kDa | NP_006748 | Human | TnT3BDP | | PKLTAPKIPEGEKVD$_{55}$↓<br>F$_{56}$DDIQKKRQNKDLME<br>SEQ ID NO: 9 | PKLTAPKIPEGEKVD$_{-COOH}$;<br>SEQ ID NO: 65<br>$_{NH2-}$F DDIQKKRQNKDLME<br>SEQ ID NO: 66 |
| MAP-2A/B/C/D | 300 kDa | CAA37535 | Rat | | 150, 90 kDa | ADRETAEEVSARIVQVVT$_{99}$*<br>A$_{100}$EAVAVLKGEQE<br>SEQ ID NO: 10 | ADRETAEEVSARIVQVVT<br>$_{-COOH}$; SEQ ID NO: 67<br>$_{NH2-}$A EAVAVLKGEQE<br>SEQ ID NO: 68 |
| MBP | 18-21 kDa | CAA10805 | Rat | M-BDP-10-12 kDa | | KSQRTQDENPWHFF$_{114}$^<br>K$_{115}$NIVTPPRTPPPSQG<br>SEQ ID NO: 11 | KSQRTQDENPWHFF-COOH;<br>SEQ ID NO: 69<br>$_{NH2-}$K115<br>NIVTPPRTPPPSQG$_{-COOH}$<br>SEQ ID NO: 70 |
| NF-L | 68 kDa | AAH39237 | Human | NFL-BDP | 30 kDa | KSRFTVLTESAAKNTD$_{297}$^<br>A$_{298}$VRAAKDEVSESRRL<br>SEQ ID NO: 12 | KSRFTVTESAAKNTD$_{COOH}$;<br>SEQ ID NO: 71<br>$_{NH2-}$AVRAAKDEVSESRRL<br>SEQ ID NO: 72 |
| NF-L | 68 kDa | AAH39237 | Human | NFL-BDP | 31 kDa | NAEEWFKSRFTVLTE$_{290}$*<br>S$_{291}$AAKNTDAVRAAKDE<br>SEQ ID NO: 13 | NAEEWFKSRFTVLTE$_{COOH}$;<br>SEQ ID NO: 73<br>$_{NH2-}$SAAKNTDAVRAAKDE<br>SEQ ID NO: 74 |
| NF-M | 150 kDa | NP_005373 | Human | NFM-BDP | 80 kDa | QAEEWFKCRYAKLTE$_{300}$^<br>A$_{301}$AEQNKEAIRSAKEE<br>SEQ ID NO: 14 | QAEEWFKCRYAKLTE-COOH;<br>SEQ ID NO: 75<br>NH2-A AEQNKEAIRSAKEE;<br>SEQ ID NO: 76 |
| NF-M | 150 kDa | NP_005373 | Human | NFL-BDP- | 32 kDa | ALKEIRSQLESHSDQ$_{283}$*<br>N$_{284}$MHQAEEWFKCRYAK<br>SEQ ID NO: 15 | ALKEIRSQLESHSDQ-COOH<br>SEQ ID NO: 77<br>$_{NH2-}$NMHQAEEWFKCRYAK<br>SEQ ID NO: 78 |
| Prion Protein | 28 kDa | AAX42952 | human | PrBDP | | AAGALVGGLGGYMLG$_{131}$*<br>S$_{132}$AMSRPIIHFGSDYE<br>SEQ ID NO: 16 | AAGALVGGLGGYMLG-$_{COOH}$<br>SEQ ID NO: 79<br>$_{NH2}$ SAMSRPIIHFGSDYE<br>SEQ ID NO: 80 |
| Slow skeletal muscle Tro-ponin-I2 | 22 kDa | NP_003273 | Human | TrI2BDP | | REIKDLKLKVMDLRG$_{107}$↓<br>K$_{108}$FKRPPLRRVRVSAD<br>SEQ ID NO: 17 | REIKDLKLKVMDLRG$_{-COOH}$;<br>SEQ ID NO: 81<br>$_{NH2-}$KFKRPPLRRVRVSAD<br>SEQ ID NO: 82 |
| Slow skeletal muscle Tro-ponin-T1 | 33 kDa | NP_003274 | Human | TnT1BDP | | PPLIPPKIPEGERVD$_{50}$↓<br>F$_{51}$DDIHRKRMEKDLLE<br>SEQ ID NO: 18 | PPLIPPKIPEGERVD$_{-COOH}$;<br>SEQ ID NO: 83<br>$_{NH2-}$FDDIHRKRMEKDLLE<br>SEQ ID NO: 84 |
| Tau 441-isoform | 50 kDa | NP_058908 | Rat | TBDP | 26 kDa | QAAGHVTQARVAGVS$_{121}$^<br>K$_{122}$DRTGNDEKKAKGADG<br>SEQ ID NO: 19 | QAAGHVTQARVAGVS$_{-COOH}$;<br>SEQ ID NO: 85<br>$_{NH2-}$KDRTGNDEKKAKGADG<br>SEQ ID NO: 86 |

TABLE 2-continued

Examples of unobvious and unique tissue protein cleavage sites produce by protease attack

| Protein | Molecular weight Protein | Acc. # | Species | BDP | Molecular weight BDP | Cleavage site identified | Example of new C-and N-terminal epitopes for fragment-specific antibodies |
|---|---|---|---|---|---|---|---|
| Tau 441-isoform | 50 kDa | AAC04279 | Human | TBP | 23 kDa | EDEAAGHVTQARMVS$_{130}$*<br>K$_{131}$SKDGTGSDDKKAKG<br>SEQ ID NO: 20 | EDEAAGHVTQARMVS$_{-COOH}$;<br>SEQ ID NO: 87<br>$_{NH2-}$KSKDGTGSDDKKAKG<br>SEQ ID NO: 88 |
| Tau 441-isoform | 50 kDa | AAC04279 | Human | TBP | | AKGADGKTKIATPRG$_{157}$*<br>A$_{158}$APPGQKGQANATRIP<br>SEQ ID NO: 21 | AKGADGKTKIATPRG$_{-COOH}$;<br>SEQ ID NO: 89<br>$_{NH2-}$APPGQKGQANATRIP<br>SEQ ID NO: 90 |
| Tau 441-isoform | 50 kDa | AAC04279 | Human | TBP | | GGGNKKIETHKLTFR$_{380}$*<br>E$_{381}$NAKAKTDHGAEIVH<br>SEQ ID NO: 22 | GGGNKKIETHKLTFR$_{-COOH}$;<br>SEQ ID NO: 91<br>$_{NH2-}$ENAKAKTDHGAEIVH<br>SEQ ID NO: 92 |
| Acti-vated Cal-pain-1 | 80 kDa | AAV41878 | Human | BDP | 76 kDa | GVSAQVQKQRARELG$_{27}$*<br>L$_{28}$GRHENAIKYLGQDY<br>SEQ ID NO: 23 | GVSAQVQKQRARELG$_{-COOH}$;<br>SEQ ID NO: 93<br>$_{NH2-}$LGRHENAIKYLGQDY<br>SEQ ID NO: 94 |
| Acti-vated Cal-pain-2 | 80 kDa | CIHUH2 | Human | BDP | 41 kDa | RGSTAGGCRNYPNTF$_{381}$*<br>W$_{382}$MNPQYLIKLEEEEE<br>SEQ ID NO: 24 | RGSTAGGCRNYPNTF$_{-COOH}$;<br>SEQ ID NO: 95<br>$_{NH2-}$WMNPQYLIKLEEEEE<br>SEQ ID NO: 96 |
| alphaII-spectrin | 260 kDa | Q13813 | Mouse | SBDP150-short | 150 kDa | LMAEEVQAVQQQEVY$_{1176}$*<br>G$_{1177}$AMPRDETDSLTASP<br>SEQ ID NO: 25 | LMAEEVQAVQQQEVY$_{-COOH}$;<br>SEQ ID NO: 97<br>$_{NH2-}$GAMPR DETDSKTASP<br>SEQ ID NO: 98 |
| alphaII-spectrin | 260 kDa | Q13813 | Human | SBDP150-short | 150 kDa | LMAEEVQAVQQQEVY$_{1176}$*<br>G$_{1177}$MMPRDETDSKTASP<br>SEQ ID NO: 26 | LMAEEVQAVQQQEVY$_{-COOH}$;<br>SEQ ID NO: 99<br>$_{NH2-}$GMMPRDETDSKTASP<br>SEQ ID NO: 100 |
| alphaII-spectrin | 260 kDa | Q13813 | Human | SBDP145 (Calpain) | 145 kDa | RSLQQLAEERSQLLG$_{1230}$*<br>S$_{1231}$AHEVQRFHRDADET<br>SEQ ID NO: 27 | RSLQQLAEERSQLLG$_{-COOH}$;<br>SEQ ID NO: 101<br>$_{NH2-}$SAHEVQRFHRDADET<br>SEQ ID NO: 102 |
| alphaII-spectrin | 260 kDa | Q13813 | Human | SBDP149 (Caspase) | 149 kDa | QQQEVYGMMPRDETD$_{1185}$*<br>S$_{1186}$KTASPWKSARLMVH<br>SEQ ID NO: 28 | QQQEVYGMMPRDETD$_{-COOH}$;<br>SEQ ID NO: 103<br>$_{NH2-}$SKTASPWKSARLMVH<br>SEQ ID NO: 104 |
| alphaII-spectrin | 260 kDa | Q13813 | Human | SBDP120 (Caspase) | 120 kDa | REAFLNTEDKGDSLD$_{1478}$*<br>S$_{1479}$VEALIKKHEDFDKA<br>SEQ ID NO: 29 | REAFLNTEDKGDSLD$_{-COOH}$;<br>SEQ ID NO: 105<br>$_{NH2-}$SVEALIKKHEDFDKA<br>SEQ ID NO: 106 |
| BAX | 21 kDa | NP_620119 | Human | | 18 kDa | SSEQIMKTGALLLQG$_{29}$↓<br>F$_{30}$IQDRAGRMGGEAPE<br>SEQ ID NO: 30 | SSEQIMKTGALLLQG$_{-COOH}$;<br>SEQ ID NO: 107<br>$_{NH2-}$FIQDRAGRMGGEAPE<br>SEQ ID NO: 108 |
| betaII-spectrin | 240 kDa | NP_003119 | Human | βIISBDP | 110 kDa | ENQMEVRKKEIEELQ$_{1440}$<br>S$_{1441}$QAQALSQEGKSTED<br>SEQ ID NO: 31 | ENQMEVRKKEIEELQ$_{-COOH}$;<br>SEQ ID NO: 109<br>$_{NH2-}$SQAQALSQEGKSTED<br>SEQ ID NO: 110 |
| betaII-spectrin | 240 kDa* | NP_003119 | Human | βIISBDP | 108 kDa | AQALSQEGKSTDEVD$_{1457}$^<br>S$_{1458}$KRLTVQTKFMELLE<br>SEQ ID NO:32 | AQALSQEGKSTDEVD$_{-COOH}$;<br>SEQ ID NO: 111<br>$_{NH2-}$SKRLTVQTKFMELLE<br>SEQ ID NO: 112 |
| betaII-spectrin | 240 kDa* | NP_003119 | Human | βIISBDP | 24 kDa | LPAEQGSPRMAETVD$_{2146}$*<br>T$_{2147}$SEMVNGATEQRTSS<br>SEQ ID NO: 33 | LPAEQGSPRMAEWD$_{-COOH}$;<br>SEQ ID NO: 113<br>$_{NH2-}$<br>T2147SEMVNGATEQRTSS<br>SEQ ID NO: 114 |
| betaII-spectrin | 240 kDa* | NP_003119 | Human | βIISBDP | 109 kDa | KKEIEELQSQAQALS$_{1448}$*<br>Q$_{1449}$EGKSTDEVDSKRLT<br>SEQ ID NO: 34 | KKEIEELQSQAQALS$_{-COOH}$;<br>SEQ ID NO: 115<br>$_{NH2-}$QEGKSTDEVDSKRLT<br>SEQ ID NO: 116 |
| betaII-spectrin | 240 kDA* | NP_003119 | Human | βIISBDP | 107 kDa | TDEVDSKRLWQTKF$_{1467}$*<br>M$_{1468}$ELLEPLNERKHNLL<br>SEQ ID NO: 35 | TDEVDSKRLTVQTKF$_{-COOH}$;<br>SEQ ID NO: 117<br>$_{NH2-}$MEL LEPL NERKHNLL<br>SEQ ID NO: 118 |
| betaII-spectrin | 240 kDa* | NP_003119 | Human | βIISBDP | 105 kDa | MELLEPLNERKHNLL$_{1482}$*<br>A$_{1483}$SKEIHQFNRDVEDE<br>SEQ ID NO: 36 | MELLEPLNERKHNLL$_{COOH}$;<br>SEQ ID NO: 119<br>$_{NH2-}$ASKEIHQFNRDVEDE<br>SEQ ID NO: 120 |

TABLE 2-continued

Examples of unobvious and unique tissue protein cleavage sites produce by protease attack

| Protein | Molecular weight Protein | Acc. # | Species | BDP | Molecular weight BDP | Cleavage site identified | Example of new C-and N-terminal epitopes for fragment-specific antibodies |
|---|---|---|---|---|---|---|---|
| Calci-neurin A alpha) | 61 kDa | Q08209 | Human | BDP | 45 kDa | ICSDDELGSEEDGFD$_{385}$* $G_{386}$ATAAARKEVIRNKI SEQ ID NO: 37 | ICSDDELGSEEDGFD$_{-COOH}$; SEQ ID NO: 121 $_{NH2-}$GATMARKEVIRNKI SEQ ID NO: 122 |
| CaMPK-IV | 55 kDa | NP_033923 | Mouse | BDP | 33 kDa | VTASTENLVPDYWID$_{30}$* $G_{31}$SNRDPLGDFFEVES SEQ ID NO: 38 | VTASTENLVPDYWID$_{-COOH}$; SEQ ID NO: 123 $_{NH2-}$GSNRDPLGDFFEVES SEQ ID NO: 124 |
| CaMPK-IV | 55 kDa | NP_033923 | Mouse | BDP | 34 kDa | CPSSPCSSVTASTEN$_{23}$* $L_{24}$VPDYWIDGSNRDPL SEQ ID NO: 39 | CPSSPCSSVIASTEN$_{COOH}$; SEQ ID NO: 125 $_{NH2-}$LVPDYWIDGSNRDPL SEQ ID NO: 126 |
| CaMPK-IV | 55 kDa | NP_033923 | Mouse | BDP | 38 kDa | KPENLLYATPAPDAP$_{178}$* $L_{177}$KIADFGLSKIVEHQ SEQ ID NO: 40 | KPENLLYATPAPDAP$_{-COOH}$; SEQ ID NO: 127 $_{NH2-}$LKIADFGLSKIVEHQ SEQ ID NO: 128 |
| CaMPK-IV | 55 kDa | NP_033923 | Mouse | BDP | 40 kDa | SKIVEHQVLMKTVCG$_{201}$* $T_{202}$PGYCAPEILRGCAY SEQ ID NO: 41 | SKIVEHQVLMKTVCG$_{-COOH}$; SEQ ID NO: 129 $_{NH2-}$TPGYCAPEILRGCAY SEQ ID NO: 130 |
| Cardiac Tro-ponin-I3 | 24 kDa | P19429 | Human | BDP | 10 kDa | TEIADLTQKIFDLRG$_{138}$↓ $K_{139}$FKRPTLRRVRISAD SEQ ID NO: 42 | TEIADLTQKIFDLRG$_{-COOH}$; SEQ ID NO: 131 $_{NH2-}$KFKRPTLRRVRISAD SEQ ID NO: 132 |
| Cardiac Tro-ponin-T2 | 35 kDa | NP_000355 | Human | BDP | 24 kDa | MEESKPKPRSFMPNL$_{85}$↓ $V_{86}$PPKIPDGERVDFDD SEQ ID NO: 43 | MEESKPKPRSFMPNL$_{-COOH}$; SEQ ID NO: 133 $_{NH2-}$V86PPKIPDGERVDFDD SEQ ID NO: 134 |
| Cardiac Tro-ponin-T2 | 35 kDa | NP_000355 | Human | BDP | 13 kDa | PNLVPPKIPDGERVD$_{97}$↓ $F_{198}$DDIHRKRMEKDLNE SEQ ID NO: 44 | PNLVPPKIPDGERVD$_{-COOH}$; SEQ ID NO: 135 $_{NH2-}$F98DDIHRKRMEKDLNE SEQ ID NO: 136 |
| NF-M | 145 kDa | AY421963 | Bovine | NF-M BDP | 112 | KVEDEK$_{467}$* $S_{468}$SEMEEAL SEQ ID NO: 45 | KVEDEK$_{467}$* SEQ ID NO: 137 $S_{468}$SEMEEAL SEQ ID NO: 138 |
| NF-M | 145 kDa | AY421963 | Bovine | NF-M BDP | 110 | KKSPVK$_{516}$* $A_{517}$TAPELK SEQ ID NO: 46 | KKSPVK$_{516}$ SEQ ID NO: 139 $A_{517}$TAPELK SEQ ID NO: 140 |
| Tau 441-isoform | 50 kDa | AAC04279 | Human | TBP | 38 kDa | HLSNVSSTGSIDMVD$_{333}$* $S_{334}$PQLATLADEVSASL SEQ ID NO: 47 | HLSNVSSTGSIDMVD$_{-COOH}$; SEQ ID NO: 141 $_{NH2-}$SPQLATLADEVSASL SEQ ID NO: 142 |
| Tau 441-isoform | 50 kDa | AAC04279 | Human | TBP | 40 kDa | MEDHAGTYGLGDRKD$_{26}$* $Q_{27}$GGYTMHQDGEGDTD SEQ ID NO: 48 | MEDHAGTYGLGDRKD$_{-COOH}$; SEQ ID NO: 143 $_{NH2-}$QGGYTMHQDGEGDTD SEQ ID NO: 144 |

The foregoing description of the invention is merely illustrative thereof, and it is understood that variations and modifications can be effected without departing from the spirit of scope of the invention as set forth in the following claims.

What is claimed is:

1. A method of determining the presence of neural injury in a subject, comprising detecting at least one or more proteolytic breakdown products of microtubule-associated protein (MAP), wherein the MAP protein is MAP-1, MAP-2A, MAP-2B, MAP-2C, MAP-2D, MAP-3 or MAP-4 in a tissue or fluid sample in contact with injured neural tissue wherein a detectable, amount of the at least one or more breakdown products of MAP is indicative of neural injury in said subject when said amount is greater than in normal subjects without neural injury.

2. The method of claim 1, wherein the MAP protein is MAP-2A, MAP-2B, MAP-2C, or MAP-2D.

3. The method of claim 1, wherein the breakdown product is a cleavage product of SEQ ID NO:10.

4. The method of claim 3, wherein the cleavage product is between position 99 and 100 of SEQ ID NO: 10.

5. The method of claim 1, wherein the neural injury is traumatic brain injury (TBI).

6. The method of claim 1, wherein the fluid sample is cerebrospinal fluid (CSF) or blood.

7. The method of claim 1, wherein the tissue sample is cortical tissue from the hippocampus.

8. The method of claim 1, wherein the breakdown products of MAP are detected using an immunoassay.

9. The method of claim 1, wherein the breakdown products of MAP are detected using a biochip array.

10. The method of claim 9, wherein the biochip array is a protein chip array.

11. The method of claim 9, wherein the biochip array is a nucleic acid array.

12. The method of claim 1, wherein the breakdown products of MAP are immobilized on the biochip array.

13. The method of claim 12, wherein the immobilized breakdown products are subjected to laser ionization to detect the molecular weight of the markers.

14. The method of claim 13, wherein ille molecular weight of the one or more breakdown products is analyzed against a threshold intensity that is normalized against total ion current.

15. The method of claim 14, wherein logarithmic transformation is used for reducing peak intensity ranges to limit the number or breakdown products detected.

* * * * *

UNITED STATES PATENT AND TRADEMARK OFFICE

CERTIFICATE OF CORRECTION

PATENT NO. : 7,456,027 B2
APPLICATION NO. : 11/106932
DATED : November 25, 2008
INVENTOR(S) : Ka-Wang Kevin Wang et al.

It is certified that error appears in the above-identified patent and that said Letters Patent is hereby corrected as shown below:

Column 16,
Lines 12-13, "caused by rapture rupture or obstruction" should read --caused by rupture or obstruction--.

Column 18,
Line 59, "symptom which is approaches a" should read --symptom which approaches a--.

Column 20,
Line 49, "brain, liver kidney" should read --brain, liver, kidney--.
Lines 50-51, "fluids such blood, CSF" should read --fluids such as blood, CSF--.

Column 22,
Line 29, "assumed to be enzyme's" should read --assumed to be the enzyme's--.
Line 47, "biomarkers fragments or" should read --biomarkers, fragments or--.

Column 25,
Line 17, "detection" should read --detection.--.

Column 26,
Line 9, "gunshots wounds" should read --gunshot wounds--.

Column 29,
Lines 60-61, "a high PH is are likely" should read --a high PH is likely--.

Column 34,
Lines 57, "Biology Antibodies" should read --Biology: Antibodies--.

Column 35,
Line 62, "Certain code can" should read --Certain codes can--.

Column 59,
Line 8, "calorimetric" should read --colorimetric--.

UNITED STATES PATENT AND TRADEMARK OFFICE

CERTIFICATE OF CORRECTION

PATENT NO. : 7,456,027 B2 
APPLICATION NO. : 11/106932
DATED : November 25, 2008
INVENTOR(S) : Ka-Wang Kevin Wang et al.

It is certified that error appears in the above-identified patent and that said Letters Patent is hereby corrected as shown below:

Column 61,
Line 51, "antibody to chose" should read --antibody to choose--.

Column 62,
Line 21, "(calorimetric method)." should read --(colorimetric method).--.

Figures 2A, 2B, 2C, 2D, 2E:
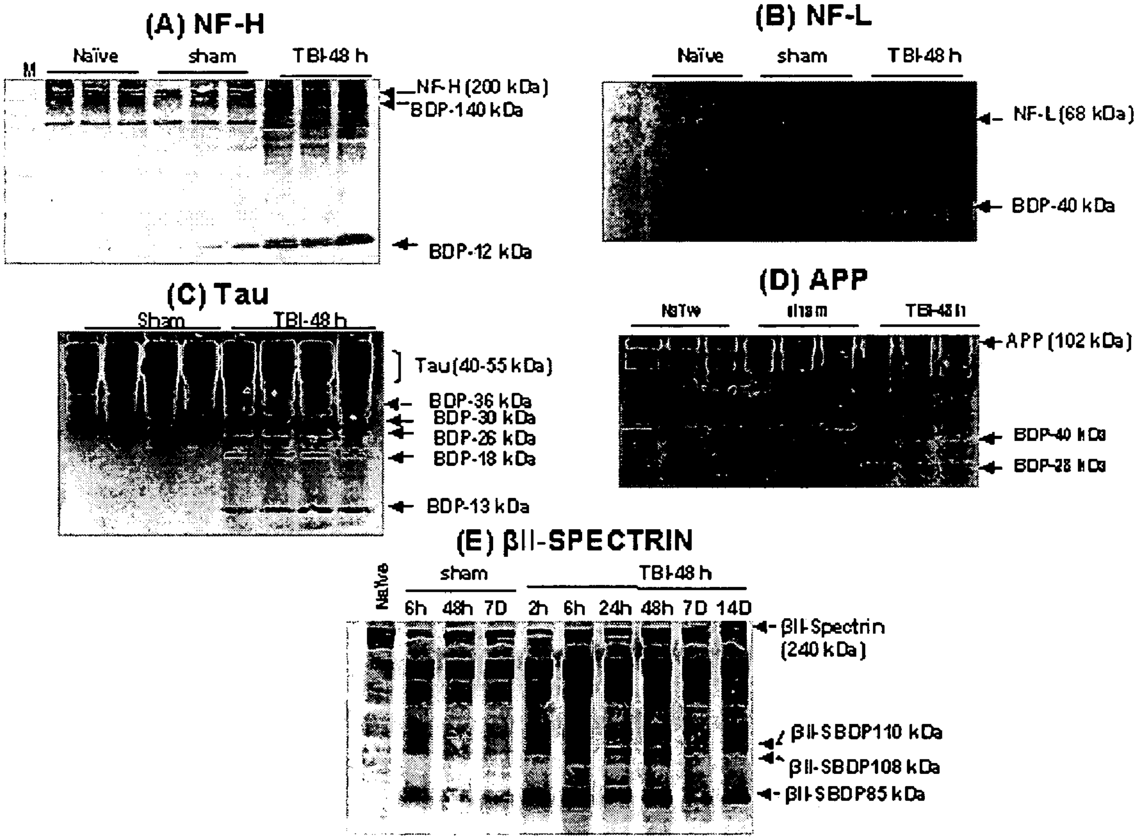
FIGS. 2A-2E are gels showing examples of neural proteins subjected to proteolytic attack 48 h after traumatic brain injury in rat hippocampus. These proteins include NF-H (FIG. 2A), NF-L (FIG. 2B), Tau (FIG. 2C), APP (FIG. 2D) and βII-spectrin (FIG. 2E). Major breakdown products (BDPs) with their relative molecular weight are indicated. Ipsilateral cortical samples were also analyzed and they showed very similar patterns of proteolysis.

Column 64,
Lines 30-48, "TBI was induced in rodents as described above. 48 h following TBI or sham operation or naive rats, samples of CSF were collected and analyzed for presence of five novel neural protein markers (MBP and MOSP) (FIG. 3) were identified to be vulnerable to endogenous proteolytic attack, producing major breakdown products (BDPs) in the ipsilateral hippocampus. Ipsilateral cortical samples were also analyzed and they showed very similar patterns of proteolysis. Based on the unique cleavage site in MBP (DENPVVHFF $_{114}K_{115}$NIVTPP) SEQ ID NO: 184), we have produced polyclonal and monoclonal that specifically detects the new N-terminal (NH2-KNIVTPP) (SEQ ID NO: 149) of MBP-BDP of 12 kDa and 10 kDa (FIG. 4). These unique BDP's when accumulated in biofluids such as CSF and blood are excellent diagnostic markers for organ-specific (brain, spinal cord or peripheral nerve) injury or stress and can be detected by techniques using fragment-specific antibody tools such as those described in FIG. 4 by Western blots or ELISA."

should read --TBI was induced in rodents as described above. 48 h following TBI or sham operation on naive rats, samples of CSF were collected and analyzed for presence of five novel neural protein markers; (NF-H (A), NF-L (B), Tau (C), APP (D) and βII-spectrin (E) (Figure 2) were identified to be vulnerable to endogenous proteolytic attack, producing major breakdown products (BDPs) in the ipsilateral hippocampus. Ipsilateral cortical samples were also analyzed and they showed very similar patterns of proteolysis. These unique BDP's when accumulated in biofluids such as CSF and blood, can be readily detected by immunological techniques such as Western blots or ELISA and thus are excellent diagnostic markers for organ-specific (brain or spinal cord or peripheral nerve) injury or stress (Figure 1).--.

Column 66,
Line 13, "Example" should read --Example 5--.

UNITED STATES PATENT AND TRADEMARK OFFICE

CERTIFICATE OF CORRECTION

PATENT NO. : 7,456,027 B2
APPLICATION NO. : 11/106932
DATED : November 25, 2008
INVENTOR(S) : Ka-Wang Kevin Wang et al.

It is certified that error appears in the above-identified patent and that said Letters Patent is hereby corrected as shown below:

Column 68,
Table 2, Row "Slow Skeletal Muscle Troponin-T1", Column "Cleavage site identified",
"VLSNMGAHFGGYLVK$_{167}$*A$_{168}$EQKRGKRQT" should read
--VLSNMGAHFGGYLVK$_{167}$*A$_{168}$EQKRGKRQTGREMKV--.

Table 2, Row "MBP", Column "Cleavage site identified",
"KSQRTQDENPWHFF$_{114}$^K$_{115}$NIVTPPRTPPPSQG" should read
--KSQRTQDENPVVHFF$_{114}$^K$_{115}$NIVTPPRTPPPSQG--.

Table 2, Row "MBP", Column "Example of new C- and N-terminal epitopes for fragment-specific antibodies",
"KSQRTQDENPWHFF-COOH" should read
--KSQRTQDENPVVHFF-COOH--.

Column 118,
Line 29, "wherein ille molecular" should read --wherein the molecular--.

Signed and Sealed this

Fourteenth Day of April, 2009

JOHN DOLL
*Acting Director of the United States Patent and Trademark Office*

SEQUENCE LISTING

<160> NUMBER OF SEQ ID NOS: 147

<210> SEQ ID NO 1
<211> LENGTH: 30
<212> TYPE: PRT
<213> ORGANISM: Canis familiaris

<400> SEQUENCE: 1

-continued

```
Trp Arg Ser Leu Gln Gln Leu Ala Glu Glu Arg Ser Glu Val Tyr Gly
1               5                   10                  15

Met Met Pro Arg Asp Asp Thr Asp Ser Lys Thr Ala Ser Pro
            20                  25                  30


<210> SEQ ID NO 2
<211> LENGTH: 31
<212> TYPE: PRT
<213> ORGANISM: Homo sapiens

<400> SEQUENCE: 2

Ala Glu Glu Asp Ala Glu Glu Glu Lys Pro Arg Pro Lys Leu Thr Ala
1               5                   10                  15

Pro Lys Ile Pro Glu Gly Glu Lys Val Asp Phe Asp Asp Ile Gln
            20                  25                  30


<210> SEQ ID NO 3
<211> LENGTH: 31
<212> TYPE: PRT
<213> ORGANISM: Homo sapiens

<400> SEQUENCE: 3

Pro Pro Leu Arg Arg Val Arg Met Ser Ala Asp Ala Met Leu Lys Ala
1               5                   10                  15

Leu Leu Gly Ser Lys His Lys Val Cys Met Asp Leu Arg Ala Asn
            20                  25                  30


<210> SEQ ID NO 4
<211> LENGTH: 31
<212> TYPE: PRT
<213> ORGANISM: Homo sapiens

<400> SEQUENCE: 4

Gly Ser Lys His Lys Val Cys Met Asp Leu Arg Ala Asn Leu Lys Gln
1               5                   10                  15

Val Lys Lys Glu Asp Thr Glu Lys Glu Arg Asp Leu Arg Asp Val
            20                  25                  30


<210> SEQ ID NO 5
<211> LENGTH: 31
<212> TYPE: PRT
<213> ORGANISM: Homo sapiens

<400> SEQUENCE: 5

Glu Glu Glu Lys Tyr Asp Met Glu Val Arg Val Gln Lys Thr Ser Lys
1               5                   10                  15

Glu Leu Glu Asp Met Asn Gln Lys Leu Phe Asp Leu Arg Gly Lys
            20                  25                  30


<210> SEQ ID NO 6
<211> LENGTH: 31
<212> TYPE: PRT
<213> ORGANISM: Homo sapiens

<400> SEQUENCE: 6

Val Leu Ser Asn Met Gly Ala His Phe Gly Gly Tyr Leu Val Lys Ala
1               5                   10                  15

Glu Gln Lys Arg Gly Lys Arg Gln Thr Gly Arg Glu Met Lys Val
            20                  25                  30


<210> SEQ ID NO 7
<211> LENGTH: 30
```

-continued

<212> TYPE: PRT
<213> ORGANISM: Homo sapiens

<400> SEQUENCE: 7

Thr Arg Glu Ile Lys Asp Leu Lys Leu Lys Val Met Asp Leu Arg Gly
1 5 10 15

Lys Phe Lys Arg Pro Pro Leu Arg Arg Val Arg Val Ser Ala
20 25 30

<210> SEQ ID NO 8
<211> LENGTH: 30
<212> TYPE: PRT
<213> ORGANISM: Homo sapiens

<400> SEQUENCE: 8

Lys Glu Leu Glu Asp Met Asn Gln Lys Leu Phe Asp Leu Arg Gly Lys
1 5 10 15

Phe Lys Arg Pro Pro Leu Arg Arg Val Arg Met Ser Ala Asp
20 25 30

<210> SEQ ID NO 9
<211> LENGTH: 30
<212> TYPE: PRT
<213> ORGANISM: Homo sapiens

<400> SEQUENCE: 9

Pro Lys Leu Thr Ala Pro Lys Ile Pro Glu Gly Glu Lys Val Asp Phe
1 5 10 15

Asp Asp Ile Gln Lys Lys Arg Gln Asn Lys Asp Leu Met Glu
20 25 30

<210> SEQ ID NO 10
<211> LENGTH: 30
<212> TYPE: PRT
<213> ORGANISM: Rattus rattus

<400> SEQUENCE: 10

Ala Asp Arg Glu Thr Ala Glu Glu Val Ser Ala Arg Ile Val Gln Val
1 5 10 15

Val Thr Ala Glu Ala Val Ala Val Leu Lys Gly Glu Gln Glu
20 25 30

<210> SEQ ID NO 11
<211> LENGTH: 30
<212> TYPE: PRT
<213> ORGANISM: Rattus rattus

<400> SEQUENCE: 11

Lys Ser Gln Arg Thr Gln Asp Glu Asn Pro Val Val His Phe Phe Lys
1 5 10 15

Asn Ile Val Thr Pro Pro Arg Thr Pro Pro Pro Ser Gln Gly
20 25 30

<210> SEQ ID NO 12
<211> LENGTH: 31
<212> TYPE: PRT
<213> ORGANISM: Homo sapiens

<400> SEQUENCE: 12

Lys Ser Arg Phe Thr Val Leu Thr Glu Ser Ala Ala Lys Asn Thr Asp
1 5 10 15

Ala Val Arg Ala Ala Lys Asp Glu Val Ser Glu Ser Arg Arg Leu

-continued 20 25 30

<210> SEQ ID NO 13
<211> LENGTH: 30
<212> TYPE: PRT
<213> ORGANISM: Homo sapiens

<400> SEQUENCE: 13

Asn Ala Glu Glu Trp Phe Lys Ser Arg Phe Thr Val Leu Thr Glu Ser
1 5 10 15

Ala Ala Lys Asn Thr Asp Ala Val Arg Ala Ala Lys Asp Glu
20 25 30

<210> SEQ ID NO 14
<211> LENGTH: 30
<212> TYPE: PRT
<213> ORGANISM: Homo sapiens

<400> SEQUENCE: 14

Gln Ala Glu Glu Trp Phe Lys Cys Arg Tyr Ala Lys Leu Thr Glu Ala
1 5 10 15

Ala Glu Gln Asn Lys Glu Ala Ile Arg Ser Ala Lys Glu Glu
20 25 30

<210> SEQ ID NO 15
<211> LENGTH: 30
<212> TYPE: PRT
<213> ORGANISM: Homo sapiens

<400> SEQUENCE: 15

Ala Leu Lys Glu Ile Arg Ser Gln Leu Glu Ser His Ser Asp Gln Asn
1 5 10 15

Met His Gln Ala Glu Glu Trp Phe Lys Cys Arg Tyr Ala Lys
20 25 30

<210> SEQ ID NO 16
<211> LENGTH: 30
<212> TYPE: PRT
<213> ORGANISM: Homo sapiens

<400> SEQUENCE: 16

Ala Ala Gly Ala Leu Val Gly Gly Leu Gly Gly Tyr Met Leu Gly Ser
1 5 10 15

Ala Met Ser Arg Pro Ile Ile His Phe Gly Ser Asp Tyr Glu
20 25 30

<210> SEQ ID NO 17
<211> LENGTH: 30
<212> TYPE: PRT
<213> ORGANISM: Homo sapiens

<400> SEQUENCE: 17

Arg Glu Ile Lys Asp Leu Lys Leu Lys Val Met Asp Leu Arg Gly Lys
1 5 10 15

Phe Lys Arg Pro Pro Leu Arg Arg Val Arg Val Ser Ala Asp
20 25 30

<210> SEQ ID NO 18
<211> LENGTH: 30
<212> TYPE: PRT
<213> ORGANISM: Homo sapiens

<400> SEQUENCE: 18

-continued

```
Pro Pro Leu Ile Pro Pro Lys Ile Pro Glu Gly Glu Arg Val Asp Phe
1               5                   10                  15

Asp Asp Ile His Arg Lys Arg Met Glu Lys Asp Leu Leu Glu
            20                  25                  30


<210> SEQ ID NO 19
<211> LENGTH: 31
<212> TYPE: PRT
<213> ORGANISM: Rattus rattus

<400> SEQUENCE: 19

Gln Ala Ala Gly His Val Thr Gln Ala Arg Val Ala Gly Val Ser Lys
1               5                   10                  15

Asp Arg Thr Gly Asn Asp Glu Lys Lys Ala Lys Gly Ala Asp Gly
            20                  25                  30


<210> SEQ ID NO 20
<211> LENGTH: 30
<212> TYPE: PRT
<213> ORGANISM: Homo sapiens

<400> SEQUENCE: 20

Glu Asp Glu Ala Ala Gly His Val Thr Gln Ala Arg Met Val Ser Lys
1               5                   10                  15

Ser Lys Asp Gly Thr Gly Ser Asp Asp Lys Lys Ala Lys Gly
            20                  25                  30


<210> SEQ ID NO 21
<211> LENGTH: 31
<212> TYPE: PRT
<213> ORGANISM: Homo sapiens

<400> SEQUENCE: 21

Ala Lys Gly Ala Asp Gly Lys Thr Lys Ile Ala Thr Pro Arg Gly Ala
1               5                   10                  15

Ala Pro Pro Gly Gln Lys Gly Gln Ala Asn Ala Thr Arg Ile Pro
            20                  25                  30


<210> SEQ ID NO 22
<211> LENGTH: 30
<212> TYPE: PRT
<213> ORGANISM: Homo sapiens

<400> SEQUENCE: 22

Gly Gly Gly Asn Lys Lys Ile Glu Thr His Lys Leu Thr Phe Arg Glu
1               5                   10                  15

Asn Ala Lys Ala Lys Thr Asp His Gly Ala Glu Ile Val His
            20                  25                  30


<210> SEQ ID NO 23
<211> LENGTH: 30
<212> TYPE: PRT
<213> ORGANISM: Homo sapiens

<400> SEQUENCE: 23

Gly Val Ser Ala Gln Val Gln Lys Gln Arg Ala Arg Glu Leu Gly Leu
1               5                   10                  15

Gly Arg His Glu Asn Ala Ile Lys Tyr Leu Gly Gln Asp Tyr
            20                  25                  30


<210> SEQ ID NO 24
```

-continued

<211> LENGTH: 30
<212> TYPE: PRT
<213> ORGANISM: Homo sapiens

<400> SEQUENCE: 24

```
Arg Gly Ser Thr Ala Gly Gly Cys Arg Asn Tyr Pro Asn Thr Phe Trp
1               5                   10                  15

Met Asn Pro Gln Tyr Leu Ile Lys Leu Glu Glu Glu Glu Glu
            20                  25                  30
```

<210> SEQ ID NO 25
<211> LENGTH: 30
<212> TYPE: PRT
<213> ORGANISM: Mus musculus

<400> SEQUENCE: 25

```
Leu Met Ala Glu Glu Val Gln Ala Val Gln Gln Gln Glu Val Tyr Gly
1               5                   10                  15

Ala Met Pro Arg Asp Glu Thr Asp Ser Lys Thr Ala Ser Pro
            20                  25                  30
```

<210> SEQ ID NO 26
<211> LENGTH: 30
<212> TYPE: PRT
<213> ORGANISM: Homo sapiens

<400> SEQUENCE: 26

```
Leu Met Ala Glu Glu Val Gln Ala Val Gln Gln Gln Glu Val Tyr Gly
1               5                   10                  15

Met Met Pro Arg Asp Glu Thr Asp Ser Lys Thr Ala Ser Pro
            20                  25                  30
```

<210> SEQ ID NO 27
<211> LENGTH: 30
<212> TYPE: PRT
<213> ORGANISM: Homo sapiens

<400> SEQUENCE: 27

```
Arg Ser Leu Gln Gln Leu Ala Glu Glu Arg Ser Gln Leu Leu Gly Ser
1               5                   10                  15

Ala His Glu Val Gln Arg Phe His Arg Asp Ala Asp Glu Thr
            20                  25                  30
```

<210> SEQ ID NO 28
<211> LENGTH: 30
<212> TYPE: PRT
<213> ORGANISM: Homo sapiens

<400> SEQUENCE: 28

```
Gln Gln Gln Glu Val Tyr Gly Met Met Pro Arg Asp Glu Thr Asp Ser
1               5                   10                  15

Lys Thr Ala Ser Pro Trp Lys Ser Ala Arg Leu Met Val His
            20                  25                  30
```

<210> SEQ ID NO 29
<211> LENGTH: 30
<212> TYPE: PRT
<213> ORGANISM: Homo sapiens

<400> SEQUENCE: 29

```
Arg Glu Ala Phe Leu Asn Thr Glu Asp Lys Gly Asp Ser Leu Asp Ser
1               5                   10                  15
```

-continued

Val Glu Ala Leu Ile Lys Lys His Glu Asp Phe Asp Lys Ala
20 25 30

<210> SEQ ID NO 30
<211> LENGTH: 30
<212> TYPE: PRT
<213> ORGANISM: Homo sapiens

<400> SEQUENCE: 30

Ser Ser Glu Gln Ile Met Lys Thr Gly Ala Leu Leu Leu Gln Gly Phe
1 5 10 15

Ile Gln Asp Arg Ala Gly Arg Met Gly Gly Glu Ala Pro Glu
20 25 30

<210> SEQ ID NO 31
<211> LENGTH: 30
<212> TYPE: PRT
<213> ORGANISM: Homo sapiens

<400> SEQUENCE: 31

Glu Asn Gln Met Glu Val Arg Lys Lys Glu Ile Glu Glu Leu Gln Ser
1 5 10 15

Gln Ala Gln Ala Leu Ser Gln Glu Gly Lys Ser Thr Glu Asp
20 25 30

<210> SEQ ID NO 32
<211> LENGTH: 30
<212> TYPE: PRT
<213> ORGANISM: Homo sapiens

<400> SEQUENCE: 32

Ala Gln Ala Leu Ser Gln Glu Gly Lys Ser Thr Asp Glu Val Asp Ser
1 5 10 15

Lys Arg Leu Thr Val Gln Thr Lys Phe Met Glu Leu Leu Glu
20 25 30

<210> SEQ ID NO 33
<211> LENGTH: 30
<212> TYPE: PRT
<213> ORGANISM: Homo sapiens

<400> SEQUENCE: 33

Leu Pro Ala Glu Gln Gly Ser Pro Arg Met Ala Glu Thr Val Asp Thr
1 5 10 15

Ser Glu Met Val Asn Gly Ala Thr Glu Gln Arg Thr Ser Ser
20 25 30

<210> SEQ ID NO 34
<211> LENGTH: 30
<212> TYPE: PRT
<213> ORGANISM: Homo sapiens

<400> SEQUENCE: 34

Lys Lys Glu Ile Glu Glu Leu Gln Ser Gln Ala Gln Ala Leu Ser Gln
1 5 10 15

Glu Gly Lys Ser Thr Asp Glu Val Asp Ser Lys Arg Leu Thr
20 25 30

<210> SEQ ID NO 35
<211> LENGTH: 30
<212> TYPE: PRT
<213> ORGANISM: Homo sapiens -continued

<400> SEQUENCE: 35

```
Thr Asp Glu Val Asp Ser Lys Arg Leu Thr Val Gln Thr Lys Phe Met
1               5                   10                  15

Glu Leu Leu Glu Pro Leu Asn Glu Arg Lys His Asn Leu Leu
            20                  25                  30
```

<210> SEQ ID NO 36
<211> LENGTH: 30
<212> TYPE: PRT
<213> ORGANISM: Homo sapiens

<400> SEQUENCE: 36

```
Met Glu Leu Leu Glu Pro Leu Asn Glu Arg Lys His Asn Leu Leu Ala
1               5                   10                  15

Ser Lys Glu Ile His Gln Phe Asn Arg Asp Val Glu Asp Glu
            20                  25                  30
```

<210> SEQ ID NO 37
<211> LENGTH: 30
<212> TYPE: PRT
<213> ORGANISM: Homo sapiens

<400> SEQUENCE: 37

```
Ile Cys Ser Asp Asp Glu Leu Gly Ser Glu Glu Asp Gly Phe Asp Gly
1               5                   10                  15

Ala Thr Ala Ala Ala Arg Lys Glu Val Ile Arg Asn Lys Ile
            20                  25                  30
```

<210> SEQ ID NO 38
<211> LENGTH: 30
<212> TYPE: PRT
<213> ORGANISM: Mus musculus

<400> SEQUENCE: 38

```
Val Thr Ala Ser Thr Glu Asn Leu Val Pro Asp Tyr Trp Ile Asp Gly
1               5                   10                  15

Ser Asn Arg Asp Pro Leu Gly Asp Phe Phe Glu Val Glu Ser
            20                  25                  30
```

<210> SEQ ID NO 39
<211> LENGTH: 30
<212> TYPE: PRT
<213> ORGANISM: Mus musculus

<400> SEQUENCE: 39

```
Cys Pro Ser Ser Pro Cys Ser Ser Val Thr Ala Ser Thr Glu Asn Leu
1               5                   10                  15

Val Pro Asp Tyr Trp Ile Asp Gly Ser Asn Arg Asp Pro Leu
            20                  25                  30
```

<210> SEQ ID NO 40
<211> LENGTH: 30
<212> TYPE: PRT
<213> ORGANISM: Mus musculus

<400> SEQUENCE: 40

```
Lys Pro Glu Asn Leu Leu Tyr Ala Thr Pro Ala Pro Asp Ala Pro Leu
1               5                   10                  15

Lys Ile Ala Asp Phe Gly Leu Ser Lys Ile Val Glu His Gln
            20                  25                  30
```

-continued

<210> SEQ ID NO 41
<211> LENGTH: 30
<212> TYPE: PRT
<213> ORGANISM: Mus musculus

<400> SEQUENCE: 41

Ser Lys Ile Val Glu His Gln Val Leu Met Lys Thr Val Cys Gly Thr
1               5                   10                  15

Pro Gly Tyr Cys Ala Pro Glu Ile Leu Arg Gly Cys Ala Tyr
            20                  25                  30

<210> SEQ ID NO 42
<211> LENGTH: 30
<212> TYPE: PRT
<213> ORGANISM: Homo sapiens

<400> SEQUENCE: 42

Thr Glu Ile Ala Asp Leu Thr Gln Lys Ile Phe Asp Leu Arg Gly Lys
1               5                   10                  15

Phe Lys Arg Pro Thr Leu Arg Arg Val Arg Ile Ser Ala Asp
            20                  25                  30

<210> SEQ ID NO 43
<211> LENGTH: 30
<212> TYPE: PRT
<213> ORGANISM: Homo sapiens

<400> SEQUENCE: 43

Met Glu Glu Ser Lys Pro Lys Pro Arg Ser Phe Met Pro Asn Leu Val
1               5                   10                  15

Pro Pro Lys Ile Pro Asp Gly Glu Arg Val Asp Phe Asp Asp
            20                  25                  30

<210> SEQ ID NO 44
<211> LENGTH: 30
<212> TYPE: PRT
<213> ORGANISM: Homo sapiens

<400> SEQUENCE: 44

Pro Asn Leu Val Pro Pro Lys Ile Pro Asp Gly Glu Arg Val Asp Phe
1               5                   10                  15

Asp Asp Ile His Arg Lys Arg Met Glu Lys Asp Leu Asn Glu
            20                  25                  30

<210> SEQ ID NO 45
<211> LENGTH: 14
<212> TYPE: PRT
<213> ORGANISM: Bos taurus

<400> SEQUENCE: 45

Lys Val Glu Asp Glu Lys Ser Ser Glu Met Glu Glu Ala Leu
1               5                   10

<210> SEQ ID NO 46
<211> LENGTH: 13
<212> TYPE: PRT
<213> ORGANISM: Bos taurus

<400> SEQUENCE: 46

Lys Lys Ser Pro Val Lys Ala Thr Ala Pro Glu Leu Lys
1               5                   10

<210> SEQ ID NO 47

-continued

```
<211> LENGTH: 30
<212> TYPE: PRT
<213> ORGANISM: Homo sapiens

<400> SEQUENCE: 47

His Leu Ser Asn Val Ser Ser Thr Gly Ser Ile Asp Met Val Asp Ser
1               5                   10                  15

Pro Gln Leu Ala Thr Leu Ala Asp Glu Val Ser Ala Ser Leu
            20                  25                  30


<210> SEQ ID NO 48
<211> LENGTH: 30
<212> TYPE: PRT
<213> ORGANISM: Homo sapiens

<400> SEQUENCE: 48

Met Glu Asp His Ala Gly Thr Tyr Gly Leu Gly Asp Arg Lys Asp Gln
1               5                   10                  15

Gly Gly Tyr Thr Met His Gln Asp Gly Glu Gly Asp Thr Asp
            20                  25                  30


<210> SEQ ID NO 49
<211> LENGTH: 15
<212> TYPE: PRT
<213> ORGANISM: Canis familiaris

<400> SEQUENCE: 49

Trp Arg Ser Leu Gln Gln Leu Ala Glu Glu Arg Ser Glu Val Tyr
1               5                   10                  15


<210> SEQ ID NO 50
<211> LENGTH: 15
<212> TYPE: PRT
<213> ORGANISM: Canis familiaris

<400> SEQUENCE: 50

Gly Met Met Pro Arg Asp Asp Thr Asp Ser Lys Thr Ala Ser Pro
1               5                   10                  15


<210> SEQ ID NO 51
<211> LENGTH: 15
<212> TYPE: PRT
<213> ORGANISM: Homo sapiens

<400> SEQUENCE: 51

Ala Glu Glu Asp Ala Glu Glu Glu Lys Pro Arg Pro Lys Leu Thr
1               5                   10                  15


<210> SEQ ID NO 52
<211> LENGTH: 16
<212> TYPE: PRT
<213> ORGANISM: Homo sapiens

<400> SEQUENCE: 52

Ala Pro Lys Ile Pro Glu Gly Glu Lys Val Asp Phe Asp Asp Ile Gln
1               5                   10                  15


<210> SEQ ID NO 53
<211> LENGTH: 15
<212> TYPE: PRT
<213> ORGANISM: Homo sapiens

<400> SEQUENCE: 53

Pro Pro Leu Arg Arg Val Arg Met Ser Ala Asp Ala Met Leu Lys
```

-continued 1 5 10 15

<210> SEQ ID NO 54
<211> LENGTH: 16
<212> TYPE: PRT
<213> ORGANISM: Homo sapiens

<400> SEQUENCE: 54

Ala Leu Leu Gly Ser Lys His Lys Val Cys Met Asp Leu Arg Ala Asn
1 5 10 15

<210> SEQ ID NO 55
<211> LENGTH: 15
<212> TYPE: PRT
<213> ORGANISM: Homo sapiens

<400> SEQUENCE: 55

Gly Ser Lys His Lys Val Cys Met Asp Leu Arg Ala Asn Leu Lys
1 5 10 15

<210> SEQ ID NO 56
<211> LENGTH: 16
<212> TYPE: PRT
<213> ORGANISM: Homo sapiens

<400> SEQUENCE: 56

Gln Val Lys Lys Glu Asp Thr Glu Lys Glu Arg Asp Leu Arg Asp Val
1 5 10 15

<210> SEQ ID NO 57
<211> LENGTH: 15
<212> TYPE: PRT
<213> ORGANISM: Homo sapiens

<400> SEQUENCE: 57

Glu Glu Glu Lys Tyr Asp Met Glu Val Arg Val Gln Lys Thr Ser
1 5 10 15

<210> SEQ ID NO 58
<211> LENGTH: 16
<212> TYPE: PRT
<213> ORGANISM: Homo sapiens

<400> SEQUENCE: 58

Lys Glu Leu Glu Asp Met Asn Gln Lys Leu Phe Asp Leu Arg Gly Lys
1 5 10 15

<210> SEQ ID NO 59
<211> LENGTH: 15
<212> TYPE: PRT
<213> ORGANISM: Homo sapiens

<400> SEQUENCE: 59

Val Leu Ser Asn Met Gly Ala His Phe Gly Gly Tyr Leu Val Lys
1 5 10 15

<210> SEQ ID NO 60
<211> LENGTH: 16
<212> TYPE: PRT
<213> ORGANISM: Homo sapiens

<400> SEQUENCE: 60

Ala Glu Gln Lys Arg Gly Lys Arg Gln Thr Gly Arg Glu Met Lys Val
1 5 10 15

-continued

<210> SEQ ID NO 61
<211> LENGTH: 15
<212> TYPE: PRT
<213> ORGANISM: Homo sapiens

<400> SEQUENCE: 61

Thr Arg Glu Ile Lys Asp Leu Lys Leu Lys Val Met Asp Leu Arg
1 5 10 15

<210> SEQ ID NO 62
<211> LENGTH: 15
<212> TYPE: PRT
<213> ORGANISM: Homo sapiens

<400> SEQUENCE: 62

Gly Lys Phe Lys Arg Pro Pro Leu Arg Arg Val Arg Val Ser Ala
1 5 10 15

<210> SEQ ID NO 63
<211> LENGTH: 16
<212> TYPE: PRT
<213> ORGANISM: Homo sapiens

<400> SEQUENCE: 63

Lys Glu Leu Glu Asp Met Asn Gln Lys Leu Phe Asp Leu Leu Arg Gly
1 5 10 15

<210> SEQ ID NO 64
<211> LENGTH: 15
<212> TYPE: PRT
<213> ORGANISM: Homo sapiens

<400> SEQUENCE: 64

Lys Phe Lys Arg Pro Pro Leu Arg Arg Val Arg Met Ser Ala Asp
1 5 10 15

<210> SEQ ID NO 65
<211> LENGTH: 15
<212> TYPE: PRT
<213> ORGANISM: Homo sapiens

<400> SEQUENCE: 65

Pro Lys Leu Thr Ala Pro Lys Ile Pro Glu Gly Glu Lys Val Asp
1 5 10 15

<210> SEQ ID NO 66
<211> LENGTH: 15
<212> TYPE: PRT
<213> ORGANISM: Homo sapiens

<400> SEQUENCE: 66

Phe Asp Asp Ile Gln Lys Lys Arg Gln Asn Lys Asp Leu Met Glu
1 5 10 15

<210> SEQ ID NO 67
<211> LENGTH: 15
<212> TYPE: PRT
<213> ORGANISM: Rattus rattus

<400> SEQUENCE: 67

Ala Asp Arg Glu Thr Ala Glu Glu Val Ser Ala Arg Ile Val Gln
1 5 10 15

<210> SEQ ID NO 68

-continued

<211> LENGTH: 15
<212> TYPE: PRT
<213> ORGANISM: Rattus rattus

<400> SEQUENCE: 68

Val Val Thr Ala Glu Ala Val Ala Val Leu Lys Gly Glu Gln Glu
1 5 10 15

<210> SEQ ID NO 69
<211> LENGTH: 15
<212> TYPE: PRT
<213> ORGANISM: Rattus rattus

<400> SEQUENCE: 69

Lys Ser Gln Arg Thr Gln Asp Glu Asn Pro Val Val His Phe Phe
1 5 10 15

<210> SEQ ID NO 70
<211> LENGTH: 15
<212> TYPE: PRT
<213> ORGANISM: Rattus rattus

<400> SEQUENCE: 70

Lys Asn Ile Val Thr Pro Pro Arg Thr Pro Pro Pro Ser Gln Gly
1 5 10 15

<210> SEQ ID NO 71
<211> LENGTH: 15
<212> TYPE: PRT
<213> ORGANISM: Homo sapiens

<400> SEQUENCE: 71

Lys Ser Arg Phe Thr Val Thr Glu Ser Ala Ala Lys Asn Thr Asp
1 5 10 15

<210> SEQ ID NO 72
<211> LENGTH: 15
<212> TYPE: PRT
<213> ORGANISM: Homo sapiens

<400> SEQUENCE: 72

Ala Val Arg Ala Ala Lys Asp Glu Val Ser Glu Ser Arg Arg Leu
1 5 10 15

<210> SEQ ID NO 73
<211> LENGTH: 15
<212> TYPE: PRT
<213> ORGANISM: Homo sapiens

<400> SEQUENCE: 73

Asn Ala Glu Glu Trp Phe Lys Ser Arg Phe Thr Val Leu Thr Glu
1 5 10 15

<210> SEQ ID NO 74
<211> LENGTH: 15
<212> TYPE: PRT
<213> ORGANISM: Homo sapiens

<400> SEQUENCE: 74

Ser Ala Ala Lys Asn Thr Asp Ala Val Arg Ala Ala Lys Asp Glu
1 5 10 15

<210> SEQ ID NO 75
<211> LENGTH: 15
<212> TYPE: PRT

-continued

<213> ORGANISM: Homo sapiens

<400> SEQUENCE: 75

Gln Ala Glu Glu Trp Phe Lys Cys Arg Tyr Ala Lys Leu Thr Glu
1 5 10 15

<210> SEQ ID NO 76
<211> LENGTH: 14
<212> TYPE: PRT
<213> ORGANISM: Homo sapiens

<400> SEQUENCE: 76

Ala Glu Gln Asn Lys Glu Ala Ile Arg Ser Ala Lys Glu Glu
1 5 10

<210> SEQ ID NO 77
<211> LENGTH: 15
<212> TYPE: PRT
<213> ORGANISM: Homo sapiens

<400> SEQUENCE: 77

Ala Leu Lys Glu Ile Arg Ser Gln Leu Glu Ser His Ser Asp Gln
1 5 10 15

<210> SEQ ID NO 78
<211> LENGTH: 15
<212> TYPE: PRT
<213> ORGANISM: Homo sapiens

<400> SEQUENCE: 78

Asn Met His Gln Ala Glu Glu Trp Phe Lys Cys Arg Tyr Ala Lys
1 5 10 15

<210> SEQ ID NO 79
<211> LENGTH: 15
<212> TYPE: PRT
<213> ORGANISM: Homo sapiens

<400> SEQUENCE: 79

Ala Ala Gly Ala Leu Val Gly Gly Leu Gly Gly Tyr Met Leu Gly
1 5 10 15

<210> SEQ ID NO 80
<211> LENGTH: 15
<212> TYPE: PRT
<213> ORGANISM: Homo sapiens

<400> SEQUENCE: 80

Ser Ala Met Ser Arg Pro Ile Ile His Phe Gly Ser Asp Tyr Glu
1 5 10 15

<210> SEQ ID NO 81
<211> LENGTH: 15
<212> TYPE: PRT
<213> ORGANISM: Homo sapiens

<400> SEQUENCE: 81

Arg Glu Ile Lys Asp Leu Lys Leu Lys Val Met Asp Leu Arg Gly
1 5 10 15

<210> SEQ ID NO 82
<211> LENGTH: 15
<212> TYPE: PRT
<213> ORGANISM: Homo sapiens -continued

<400> SEQUENCE: 82

```
Lys Phe Lys Arg Pro Pro Leu Arg Arg Val Arg Val Ser Ala Asp
1               5                   10                  15
```

<210> SEQ ID NO 83
<211> LENGTH: 15
<212> TYPE: PRT
<213> ORGANISM: Homo sapiens

<400> SEQUENCE: 83

```
Pro Pro Leu Ile Pro Pro Lys Ile Pro Glu Gly Glu Arg Val Asp
1               5                   10                  15
```

<210> SEQ ID NO 84
<211> LENGTH: 15
<212> TYPE: PRT
<213> ORGANISM: Homo sapiens

<400> SEQUENCE: 84

```
Phe Asp Asp Ile His Arg Lys Arg Met Glu Lys Asp Leu Leu Glu
1               5                   10                  15
```

<210> SEQ ID NO 85
<211> LENGTH: 15
<212> TYPE: PRT
<213> ORGANISM: Rattus rattus

<400> SEQUENCE: 85

```
Gln Ala Ala Gly His Val Thr Gln Ala Arg Val Ala Gly Val Ser
1               5                   10                  15
```

<210> SEQ ID NO 86
<211> LENGTH: 16
<212> TYPE: PRT
<213> ORGANISM: Rattus rattus

<400> SEQUENCE: 86

```
Lys Asp Arg Thr Gly Asn Asp Glu Lys Lys Ala Lys Gly Ala Asp Gly
1               5                   10                  15
```

<210> SEQ ID NO 87
<211> LENGTH: 15
<212> TYPE: PRT
<213> ORGANISM: Homo sapiens

<400> SEQUENCE: 87

```
Glu Asp Glu Ala Ala Gly His Val Thr Gln Ala Arg Met Val Ser
1               5                   10                  15
```

<210> SEQ ID NO 88
<211> LENGTH: 15
<212> TYPE: PRT
<213> ORGANISM: Homo sapiens

<400> SEQUENCE: 88

```
Lys Ser Lys Asp Gly Thr Gly Ser Asp Asp Lys Lys Ala Lys Gly
1               5                   10                  15
```

<210> SEQ ID NO 89
<211> LENGTH: 15
<212> TYPE: PRT
<213> ORGANISM: Homo sapiens

<400> SEQUENCE: 89

-continued

Ala Lys Gly Ala Asp Gly Lys Thr Lys Ile Ala Thr Pro Arg Gly
1 5 10 15

<210> SEQ ID NO 90
<211> LENGTH: 15
<212> TYPE: PRT
<213> ORGANISM: Homo sapiens

<400> SEQUENCE: 90

Ala Pro Pro Gly Gln Lys Gly Gln Ala Asn Ala Thr Arg Ile Pro
1 5 10 15

<210> SEQ ID NO 91
<211> LENGTH: 15
<212> TYPE: PRT
<213> ORGANISM: Homo sapiens

<400> SEQUENCE: 91

Gly Gly Gly Asn Lys Lys Ile Glu Thr His Lys Leu Thr Phe Arg
1 5 10 15

<210> SEQ ID NO 92
<211> LENGTH: 15
<212> TYPE: PRT
<213> ORGANISM: Homo sapiens

<400> SEQUENCE: 92

Glu Asn Ala Lys Ala Lys Thr Asp His Gly Ala Glu Ile Val His
1 5 10 15

<210> SEQ ID NO 93
<211> LENGTH: 15
<212> TYPE: PRT
<213> ORGANISM: Homo sapiens

<400> SEQUENCE: 93

Gly Val Ser Ala Gln Val Gln Lys Gln Arg Ala Arg Glu Leu Gly
1 5 10 15

<210> SEQ ID NO 94
<211> LENGTH: 15
<212> TYPE: PRT
<213> ORGANISM: Homo sapiens

<400> SEQUENCE: 94

Leu Gly Arg His Glu Asn Ala Ile Lys Tyr Leu Gly Gln Asp Tyr
1 5 10 15

<210> SEQ ID NO 95
<211> LENGTH: 15
<212> TYPE: PRT
<213> ORGANISM: Homo sapiens

<400> SEQUENCE: 95

Arg Gly Ser Thr Ala Gly Gly Cys Arg Asn Tyr Pro Asn Thr Phe
1 5 10 15

<210> SEQ ID NO 96
<211> LENGTH: 15
<212> TYPE: PRT
<213> ORGANISM: Homo sapiens

<400> SEQUENCE: 96

Trp Met Asn Pro Gln Tyr Leu Ile Lys Leu Glu Glu Glu Glu Glu
1 5 10 15

-continued

<210> SEQ ID NO 97
<211> LENGTH: 15
<212> TYPE: PRT
<213> ORGANISM: Mus musculus

<400> SEQUENCE: 97

```
Leu Met Ala Glu Glu Val Gln Ala Val Gln Gln Gln Glu Val Tyr
1               5                   10                  15
```

<210> SEQ ID NO 98
<211> LENGTH: 15
<212> TYPE: PRT
<213> ORGANISM: Mus musculus

<400> SEQUENCE: 98

```
Gly Ala Met Pro Arg Asp Glu Thr Asp Ser Lys Thr Ala Ser Pro
1               5                   10                  15
```

<210> SEQ ID NO 99
<211> LENGTH: 15
<212> TYPE: PRT
<213> ORGANISM: Homo sapiens

<400> SEQUENCE: 99

```
Leu Met Ala Glu Glu Val Gln Ala Val Gln Gln Gln Glu Val Tyr
1               5                   10                  15
```

<210> SEQ ID NO 100
<211> LENGTH: 15
<212> TYPE: PRT
<213> ORGANISM: Homo sapiens

<400> SEQUENCE: 100

```
Gly Met Met Pro Arg Asp Glu Thr Asp Ser Lys Thr Ala Ser Pro
1               5                   10                  15
```

<210> SEQ ID NO 101
<211> LENGTH: 15
<212> TYPE: PRT
<213> ORGANISM: Homo sapiens

<400> SEQUENCE: 101

```
Arg Ser Leu Gln Gln Leu Ala Glu Glu Arg Ser Gln Leu Leu Gly
1               5                   10                  15
```

<210> SEQ ID NO 102
<211> LENGTH: 15
<212> TYPE: PRT
<213> ORGANISM: Homo sapiens

<400> SEQUENCE: 102

```
Ser Ala His Glu Val Gln Arg Phe His Arg Asp Ala Asp Glu Thr
1               5                   10                  15
```

<210> SEQ ID NO 103
<211> LENGTH: 15
<212> TYPE: PRT
<213> ORGANISM: Homo sapiens

<400> SEQUENCE: 103

```
Gln Gln Gln Glu Val Tyr Gly Met Met Pro Arg Asp Glu Thr Asp
1               5                   10                  15
```

-continued

<210> SEQ ID NO 104
<211> LENGTH: 15
<212> TYPE: PRT
<213> ORGANISM: Homo sapiens

<400> SEQUENCE: 104

Ser Lys Thr Ala Ser Pro Trp Lys Ser Ala Arg Leu Met Val His
1 5 10 15

<210> SEQ ID NO 105
<211> LENGTH: 15
<212> TYPE: PRT
<213> ORGANISM: Homo sapiens

<400> SEQUENCE: 105

Arg Glu Ala Phe Leu Asn Thr Glu Asp Lys Gly Asp Ser Leu Asp
1 5 10 15

<210> SEQ ID NO 106
<211> LENGTH: 15
<212> TYPE: PRT
<213> ORGANISM: Homo sapiens

<400> SEQUENCE: 106

Ser Val Glu Ala Leu Ile Lys Lys His Glu Asp Phe Asp Lys Ala
1 5 10 15

<210> SEQ ID NO 107
<211> LENGTH: 15
<212> TYPE: PRT
<213> ORGANISM: Homo sapiens

<400> SEQUENCE: 107

Ser Ser Glu Gln Ile Met Lys Thr Gly Ala Leu Leu Leu Gln Gly
1 5 10 15

<210> SEQ ID NO 108
<211> LENGTH: 15
<212> TYPE: PRT
<213> ORGANISM: Homo sapiens

<400> SEQUENCE: 108

Phe Ile Gln Asp Arg Ala Gly Arg Met Gly Gly Glu Ala Pro Glu
1 5 10 15

<210> SEQ ID NO 109
<211> LENGTH: 15
<212> TYPE: PRT
<213> ORGANISM: Homo sapiens

<400> SEQUENCE: 109

Glu Asn Gln Met Glu Val Arg Lys Lys Glu Ile Glu Glu Leu Gln
1 5 10 15

<210> SEQ ID NO 110
<211> LENGTH: 15
<212> TYPE: PRT
<213> ORGANISM: Homo sapiens

<400> SEQUENCE: 110

Ser Gln Ala Gln Ala Leu Ser Gln Glu Gly Lys Ser Thr Glu Asp
1 5 10 15

<210> SEQ ID NO 111
<211> LENGTH: 15

-continued

<212> TYPE: PRT
<213> ORGANISM: Homo sapiens

<400> SEQUENCE: 111

Ala Gln Ala Leu Ser Gln Glu Gly Lys Ser Thr Asp Glu Val Asp
1 5 10 15

<210> SEQ ID NO 112
<211> LENGTH: 15
<212> TYPE: PRT
<213> ORGANISM: Homo sapiens

<400> SEQUENCE: 112

Ser Lys Arg Leu Thr Val Gln Thr Lys Phe Met Glu Leu Leu Glu
1 5 10 15

<210> SEQ ID NO 113
<211> LENGTH: 15
<212> TYPE: PRT
<213> ORGANISM: Homo sapiens

<400> SEQUENCE: 113

Leu Pro Ala Glu Gln Gly Ser Pro Arg Met Ala Glu Thr Val Asp
1 5 10 15

<210> SEQ ID NO 114
<211> LENGTH: 15
<212> TYPE: PRT
<213> ORGANISM: Homo sapiens

<400> SEQUENCE: 114

Thr Ser Glu Met Val Asn Gly Ala Thr Glu Gln Arg Thr Ser Ser
1 5 10 15

<210> SEQ ID NO 115
<211> LENGTH: 15
<212> TYPE: PRT
<213> ORGANISM: Homo sapiens

<400> SEQUENCE: 115

Lys Lys Glu Ile Glu Glu Leu Gln Ser Gln Ala Gln Ala Leu Ser
1 5 10 15

<210> SEQ ID NO 116
<211> LENGTH: 15
<212> TYPE: PRT
<213> ORGANISM: Homo sapiens

<400> SEQUENCE: 116

Gln Glu Gly Lys Ser Thr Asp Glu Val Asp Ser Lys Arg Leu Thr
1 5 10 15

<210> SEQ ID NO 117
<211> LENGTH: 15
<212> TYPE: PRT
<213> ORGANISM: Homo sapiens

<400> SEQUENCE: 117

Thr Asp Glu Val Asp Ser Lys Arg Leu Thr Val Gln Thr Lys Phe
1 5 10 15

<210> SEQ ID NO 118
<211> LENGTH: 15
<212> TYPE: PRT
<213> ORGANISM: Homo sapiens -continued

<400> SEQUENCE: 118

Met Glu Leu Leu Glu Pro Leu Asn Glu Arg Lys His Asn Leu Leu
1 5 10 15

<210> SEQ ID NO 119
<211> LENGTH: 15
<212> TYPE: PRT
<213> ORGANISM: Homo sapiens

<400> SEQUENCE: 119

Met Glu Leu Leu Glu Pro Leu Asn Glu Arg Lys His Asn Leu Leu
1 5 10 15

<210> SEQ ID NO 120
<211> LENGTH: 15
<212> TYPE: PRT
<213> ORGANISM: Homo sapiens

<400> SEQUENCE: 120

Ala Ser Lys Glu Ile His Gln Phe Asn Arg Asp Val Glu Asp Glu
1 5 10 15

<210> SEQ ID NO 121
<211> LENGTH: 15
<212> TYPE: PRT
<213> ORGANISM: Homo sapiens

<400> SEQUENCE: 121

Ile Cys Ser Asp Asp Glu Leu Gly Ser Glu Glu Asp Gly Phe Asp
1 5 10 15

<210> SEQ ID NO 122
<211> LENGTH: 15
<212> TYPE: PRT
<213> ORGANISM: Homo sapiens

<400> SEQUENCE: 122

Gly Ala Thr Ala Ala Ala Arg Lys Glu Val Ile Arg Asn Lys Ile
1 5 10 15

<210> SEQ ID NO 123
<211> LENGTH: 15
<212> TYPE: PRT
<213> ORGANISM: Mus musculus

<400> SEQUENCE: 123

Val Thr Ala Ser Thr Glu Asn Leu Val Pro Asp Tyr Trp Ile Asp
1 5 10 15

<210> SEQ ID NO 124
<211> LENGTH: 15
<212> TYPE: PRT
<213> ORGANISM: Mus musculus

<400> SEQUENCE: 124

Gly Ser Asn Arg Asp Pro Leu Gly Asp Phe Phe Glu Val Glu Ser
1 5 10 15

<210> SEQ ID NO 125
<211> LENGTH: 15
<212> TYPE: PRT
<213> ORGANISM: Mus musculus

<400> SEQUENCE: 125

-continued

Cys Pro Ser Ser Pro Cys Ser Ser Val Thr Ala Ser Thr Glu Asn
1 5 10 15

<210> SEQ ID NO 126
<211> LENGTH: 15
<212> TYPE: PRT
<213> ORGANISM: Mus musculus

<400> SEQUENCE: 126

Leu Val Pro Asp Tyr Trp Ile Asp Gly Ser Asn Arg Asp Pro Leu
1 5 10 15

<210> SEQ ID NO 127
<211> LENGTH: 15
<212> TYPE: PRT
<213> ORGANISM: Mus musculus

<400> SEQUENCE: 127

Lys Pro Glu Asn Leu Leu Tyr Ala Thr Pro Ala Pro Asp Ala Pro
1 5 10 15

<210> SEQ ID NO 128
<211> LENGTH: 15
<212> TYPE: PRT
<213> ORGANISM: Mus musculus

<400> SEQUENCE: 128

Leu Lys Ile Ala Asp Phe Gly Leu Ser Lys Ile Val Glu His Gln
1 5 10 15

<210> SEQ ID NO 129
<211> LENGTH: 15
<212> TYPE: PRT
<213> ORGANISM: Mus musculus

<400> SEQUENCE: 129

Ser Lys Ile Val Glu His Gln Val Leu Met Lys Thr Val Cys Gly
1 5 10 15

<210> SEQ ID NO 130
<211> LENGTH: 15
<212> TYPE: PRT
<213> ORGANISM: Mus musculus

<400> SEQUENCE: 130

Thr Pro Gly Tyr Cys Ala Pro Glu Ile Leu Arg Gly Cys Ala Tyr
1 5 10 15

<210> SEQ ID NO 131
<211> LENGTH: 15
<212> TYPE: PRT
<213> ORGANISM: Homo sapiens

<400> SEQUENCE: 131

Thr Glu Ile Ala Asp Leu Thr Gln Lys Ile Phe Asp Leu Arg Gly
1 5 10 15

<210> SEQ ID NO 132
<211> LENGTH: 15
<212> TYPE: PRT
<213> ORGANISM: Homo sapiens

<400> SEQUENCE: 132

Lys Phe Lys Arg Pro Thr Leu Arg Arg Val Arg Ile Ser Ala Asp

-continued

```
1               5                   10                  15


<210> SEQ ID NO 133
<211> LENGTH: 15
<212> TYPE: PRT
<213> ORGANISM: Homo sapiens

<400> SEQUENCE: 133

Met Glu Glu Ser Lys Pro Lys Pro Arg Ser Phe Met Pro Asn Leu
1               5                   10                  15


<210> SEQ ID NO 134
<211> LENGTH: 15
<212> TYPE: PRT
<213> ORGANISM: Homo sapiens

<400> SEQUENCE: 134

Val Pro Pro Lys Ile Pro Asp Gly Glu Arg Val Asp Phe Asp Asp
1               5                   10                  15


<210> SEQ ID NO 135
<211> LENGTH: 15
<212> TYPE: PRT
<213> ORGANISM: Homo sapiens

<400> SEQUENCE: 135

Pro Asn Leu Val Pro Pro Lys Ile Pro Asp Gly Glu Arg Val Asp
1               5                   10                  15


<210> SEQ ID NO 136
<211> LENGTH: 15
<212> TYPE: PRT
<213> ORGANISM: Homo sapiens

<400> SEQUENCE: 136

Phe Asp Asp Ile His Arg Lys Arg Met Glu Lys Asp Leu Asn Glu
1               5                   10                  15


<210> SEQ ID NO 137
<211> LENGTH: 6
<212> TYPE: PRT
<213> ORGANISM: Bos taurus

<400> SEQUENCE: 137

Lys Val Glu Asp Glu Lys
1               5


<210> SEQ ID NO 138
<211> LENGTH: 8
<212> TYPE: PRT
<213> ORGANISM: Bos taurus

<400> SEQUENCE: 138

Ser Ser Glu Met Glu Glu Ala Leu
1               5


<210> SEQ ID NO 139
<211> LENGTH: 6
<212> TYPE: PRT
<213> ORGANISM: Bos taurus

<400> SEQUENCE: 139

Lys Lys Ser Pro Val Lys
1               5
```

-continued

<210> SEQ ID NO 140
<211> LENGTH: 7
<212> TYPE: PRT
<213> ORGANISM: Bos taurus

<400> SEQUENCE: 140

Ala Thr Ala Pro Glu Leu Lys
1               5

<210> SEQ ID NO 141
<211> LENGTH: 15
<212> TYPE: PRT
<213> ORGANISM: Homo sapiens

<400> SEQUENCE: 141

His Leu Ser Asn Val Ser Ser Thr Gly Ser Ile Asp Met Val Asp
1               5                   10                  15

<210> SEQ ID NO 142
<211> LENGTH: 15
<212> TYPE: PRT
<213> ORGANISM: Homo sapiens

<400> SEQUENCE: 142

Ser Pro Gln Leu Ala Thr Leu Ala Asp Glu Val Ser Ala Ser Leu
1               5                   10                  15

<210> SEQ ID NO 143
<211> LENGTH: 15
<212> TYPE: PRT
<213> ORGANISM: Homo sapiens

<400> SEQUENCE: 143

Met Glu Asp His Ala Gly Thr Tyr Gly Leu Gly Asp Arg Lys Asp
1               5                   10                  15

<210> SEQ ID NO 144
<211> LENGTH: 15
<212> TYPE: PRT
<213> ORGANISM: Homo sapiens

<400> SEQUENCE: 144

Gln Gly Gly Tyr Thr Met His Gln Asp Gly Glu Gly Asp Thr Asp
1               5                   10                  15

<210> SEQ ID NO 145
<211> LENGTH: 17
<212> TYPE: PRT
<213> ORGANISM: Homo sapiens

<400> SEQUENCE: 145

Ala Arg Val Ala Gly Val Ser Lys Asp Arg Thr Gly Asn Thr Asx Asp
1               5                   10                  15

Pro

<210> SEQ ID NO 146
<211> LENGTH: 7
<212> TYPE: PRT
<213> ORGANISM: Homo sapiens

<400> SEQUENCE: 146

Ala Arg Val Ala Gly Val Ser
1               5

-continued

```
<210> SEQ ID NO 147
<211> LENGTH: 8
<212> TYPE: PRT
<213> ORGANISM: Homo sapiens

<400> SEQUENCE: 147

Lys Asp Arg Thr Gly Asn Asp Glu
1               5
```